(12) United States Patent
Baron et al.

(10) Patent No.: US 12,076,036 B2
(45) Date of Patent: Sep. 3, 2024

(54) THROMBECTOMY SYSTEMS AND DEVICES WITH ASPIRATION, AND METHODS OF USE THEREOF

(71) Applicant: Endovascular Engineering, Inc., Menlo Park, CA (US)

(72) Inventors: Scott J. Baron, Menlo Park, CA (US); Michael Rosenthal, Menlo Park, CA (US); David Snow, San Carlos, CA (US); Brian Domecus, San Carlos, CA (US)

(73) Assignee: Endovascular Engineering, Inc., Menlo Park, CA (US)

( * ) Notice: Subject to any disclaimer, the term of this patent is extended or adjusted under 35 U.S.C. 154(b) by 0 days.

(21) Appl. No.: 18/099,667

(22) Filed: Jan. 20, 2023

(65) Prior Publication Data
US 2024/0245417 A1     Jul. 25, 2024

Related U.S. Application Data

(63) Continuation of application No. 17/682,949, filed on Feb. 28, 2022, now abandoned.
(Continued)

(51) Int. Cl.
*A61B 17/221*     (2006.01)
*A61B 17/22*      (2006.01)
*A61M 1/00*       (2006.01)

(52) U.S. Cl.
CPC ........ *A61B 17/221* (2013.01); *A61M 1/774* (2021.05); *A61B 2017/22079* (2013.01); *A61B 2017/22084* (2013.01); *A61B 2017/2215* (2013.01)

(58) Field of Classification Search
CPC . A61B 17/22; A61B 17/22031; A61B 17/221; A61B 17/320758; A61B 2017/00389; A61B 2017/00831; A61B 2017/22034; A61B 2017/22035; A61B 2017/2204; A61B 2017/22045; A61B 2017/22075; A61B 2017/22079; A61B 2017/2215; A61B 2017/2217;
(Continued)

(56) References Cited

U.S. PATENT DOCUMENTS

| 4,646,736 | A | 3/1987 | Auth |
| 5,011,488 | A | 4/1991 | Ginsburg |

(Continued)

FOREIGN PATENT DOCUMENTS

| AU | 2013266995 A1 | 1/2014 |
| CN | 101711131 A | 5/2010 |

(Continued)

OTHER PUBLICATIONS

CN 105688292 (Year: 2016).*
(Continued)

*Primary Examiner* — Kankindi Rwego
(74) *Attorney, Agent, or Firm* — COOLEY LLP

(57) ABSTRACT

Described herein are systems, devices, and methods for aspiration and mechanical thrombectomy. In some embodiments, a thrombectomy device for removing a thrombus from a vessel can include a handle assembly, a vacuum source, an aspiration catheter with an expandable distal portion, and a flexible shaft configured to rotate within the aspiration catheter.

20 Claims, 25 Drawing Sheets

Related U.S. Application Data

(60) Provisional application No. 63/170,346, filed on Apr. 2, 2021, provisional application No. 63/155,191, filed on Mar. 1, 2021.

(58) Field of Classification Search
CPC ....... A61B 2017/320716; A61B 2017/320733; A61M 25/0043; A61M 25/0067; A61M 25/0068; A61M 25/0069; A61M 25/007; A61M 25/0074; A61M 25/008; A61M 25/0147; A61M 25/0155; A61M 2025/0059; A61M 2025/0063; A61M 2025/0073
USPC .......................................................... 606/127
See application file for complete search history.

(56) References Cited

U.S. PATENT DOCUMENTS

| | | |
|---|---|---|
| 5,108,411 A | 4/1992 | McKenzie |
| 5,135,482 A | 8/1992 | Neracher |
| 5,150,450 A | 9/1992 | Swenson et al. |
| 5,423,799 A | 6/1995 | Shiu |
| 5,584,803 A | 12/1996 | Stevens et al. |
| 5,695,507 A | 12/1997 | Auth et al. |
| 5,876,414 A | 3/1999 | Straub |
| 5,971,996 A | 10/1999 | Tugendreich et al. |
| 6,001,112 A | 12/1999 | Taylor |
| 6,090,118 A | 7/2000 | McGuckin, Jr. |
| 6,113,614 A | 9/2000 | Mears |
| 6,183,450 B1 | 2/2001 | Lois |
| 6,228,046 B1 | 5/2001 | Brisken |
| 6,238,405 B1 | 5/2001 | Findlay, III et al. |
| 6,287,271 B1 | 9/2001 | Dubrul et al. |
| 6,454,775 B1 | 9/2002 | Demarais et al. |
| 6,508,782 B1 | 1/2003 | Evans et al. |
| 6,616,676 B2 | 9/2003 | Bashiri et al. |
| 6,632,236 B2 | 10/2003 | Hogendijk |
| 6,676,637 B1 | 1/2004 | Bonnette et al. |
| 6,767,353 B1 | 7/2004 | Shiber |
| 6,926,725 B2 | 8/2005 | Cooke et al. |
| 6,945,977 B2 | 9/2005 | Demarais et al. |
| 7,037,316 B2 | 5/2006 | McGuckin, Jr. et al. |
| 7,374,560 B2 | 5/2008 | Ressemann et al. |
| 7,399,307 B2 | 7/2008 | Evans et al. |
| 7,507,246 B2 | 3/2009 | McGuckin et al. |
| 7,666,161 B2 | 2/2010 | Nash et al. |
| 7,780,694 B2 | 8/2010 | Palmer et al. |
| 7,833,239 B2 | 11/2010 | Nash |
| 7,942,852 B2 | 5/2011 | Mas et al. |
| 7,947,012 B2 | 5/2011 | Spurchise et al. |
| 7,959,608 B2 | 6/2011 | Nash et al. |
| 7,976,528 B2 | 7/2011 | Nash et al. |
| 8,075,510 B2 | 12/2011 | Aklog et al. |
| 8,092,470 B2 | 1/2012 | Miyamoto et al. |
| 8,613,717 B2 | 12/2013 | Aklog et al. |
| 8,647,355 B2 | 2/2014 | Escudero et al. |
| 8,734,374 B2 | 5/2014 | Aklog et al. |
| 8,764,779 B2 | 7/2014 | Levine et al. |
| 8,784,434 B2 | 7/2014 | Rosenbluth et al. |
| 8,920,402 B2 | 12/2014 | Nash et al. |
| 8,956,386 B2 | 2/2015 | Hauser et al. |
| 9,050,127 B2 | 6/2015 | Bonnette et al. |
| 9,055,964 B2 | 6/2015 | Cartier et al. |
| 9,282,992 B2 | 3/2016 | Levine et al. |
| 9,402,938 B2 | 8/2016 | Aklog et al. |
| 9,463,035 B1 | 10/2016 | Greenhalgh et al. |
| 9,492,192 B2 | 11/2016 | To et al. |
| 9,539,022 B2 | 1/2017 | Bowman |
| 9,655,633 B2 | 5/2017 | Leynov et al. |
| 9,808,277 B2 | 11/2017 | Nash et al. |
| 9,848,881 B2 | 12/2017 | Sutton et al. |
| 9,848,975 B2 | 12/2017 | Hauser |
| 9,943,321 B2 | 4/2018 | Nita |
| 10,016,266 B2 | 7/2018 | Hauser |
| 10,045,790 B2 | 8/2018 | Cox et al. |
| 10,064,645 B2 | 9/2018 | Levine et al. |
| 10,117,671 B2 | 11/2018 | McGuckin, Jr. et al. |
| 10,154,854 B2 | 12/2018 | To et al. |
| 10,183,146 B2 | 1/2019 | Yang et al. |
| 10,183,147 B2 | 1/2019 | Yang et al. |
| 10,188,409 B2 | 1/2019 | Smalling |
| 10,213,582 B2 | 2/2019 | Garrison et al. |
| 10,307,340 B2 | 6/2019 | Bagwell et al. |
| 10,342,571 B2 | 7/2019 | Marchand et al. |
| 10,441,301 B2 | 10/2019 | Vale et al. |
| 10,492,823 B2 | 12/2019 | Jamous et al. |
| 10,568,654 B2 | 2/2020 | Cartier et al. |
| 10,582,939 B2 | 3/2020 | Brady et al. |
| 10,668,258 B1 | 6/2020 | Calhoun et al. |
| 10,682,152 B2 | 6/2020 | Vale et al. |
| 10,695,159 B2 | 6/2020 | Hauser |
| 10,709,471 B2 | 7/2020 | Rosenbluth et al. |
| 10,792,056 B2 | 10/2020 | Vale et al. |
| 10,799,331 B2 | 10/2020 | Hauser |
| 10,835,272 B2 | 11/2020 | Yang et al. |
| 10,835,711 B2 | 11/2020 | Yang et al. |
| 10,912,577 B2 | 2/2021 | Marchand et al. |
| 10,959,750 B2 | 3/2021 | Wallace |
| 10,960,178 B2 | 3/2021 | Savastano et al. |
| 10,993,731 B2 | 5/2021 | Leynov et al. |
| 11,058,848 B2 | 7/2021 | Jalgaonkar et al. |
| 11,096,712 B2 | 8/2021 | Teigen et al. |
| 11,191,556 B2 | 12/2021 | Jalgaonkar et al. |
| 11,197,683 B1 | 12/2021 | Teigen et al. |
| 11,224,458 B2 | 1/2022 | Savastano et al. |
| 11,253,277 B2 | 2/2022 | Buck et al. |
| 11,259,821 B2 | 3/2022 | Buck et al. |
| 11,311,304 B2 | 4/2022 | Kelly et al. |
| 11,357,958 B2 | 6/2022 | Kawwas et al. |
| 11,376,028 B1 | 7/2022 | Saadat et al. |
| 11,395,665 B2 | 7/2022 | Yang et al. |
| 11,464,537 B2 | 10/2022 | Cartier et al. |
| 11,471,175 B2 | 10/2022 | Nguyen et al. |
| 11,471,183 B1 | 10/2022 | Deaton et al. |
| 11,497,514 B2 | 11/2022 | Greenhalgh et al. |
| 11,504,151 B2 | 11/2022 | Deaton et al. |
| 2001/0052345 A1 | 12/2001 | Niazi |
| 2002/0107479 A1 | 8/2002 | Bates et al. |
| 2002/0138088 A1 | 9/2002 | Nash et al. |
| 2003/0139751 A1 | 7/2003 | Evans et al. |
| 2004/0019358 A1 | 1/2004 | Kear |
| 2004/0039371 A1 | 2/2004 | Tockman et al. |
| 2004/0082962 A1 | 4/2004 | Demarais et al. |
| 2004/0181249 A1 | 9/2004 | Torrance et al. |
| 2004/0220519 A1 | 11/2004 | Wulfman et al. |
| 2004/0260333 A1 | 12/2004 | Dubrul et al. |
| 2006/0058838 A1 | 3/2006 | Bose et al. |
| 2007/0208370 A1 | 9/2007 | Hauser et al. |
| 2007/0219484 A1 | 9/2007 | Straub |
| 2007/0239182 A1 | 10/2007 | Glines et al. |
| 2007/0250096 A1 | 10/2007 | Yamane et al. |
| 2008/0046072 A1 | 2/2008 | Laborde et al. |
| 2008/0097499 A1 | 4/2008 | Nash et al. |
| 2008/0289181 A1 | 11/2008 | Kozak et al. |
| 2008/0306498 A1 | 12/2008 | Thatcher et al. |
| 2009/0163846 A1 | 6/2009 | Aklog et al. |
| 2009/0171368 A1 | 7/2009 | Pearce et al. |
| 2010/0174309 A1* | 7/2010 | Fulkerson ............... A61F 2/915 606/200 |
| 2010/0185210 A1 | 7/2010 | Hauser et al. |
| 2011/0009890 A1 | 1/2011 | Palmer et al. |
| 2011/0022075 A1 | 1/2011 | Christiansen et al. |
| 2011/0087147 A1 | 4/2011 | Garrison et al. |
| 2011/0152823 A1 | 6/2011 | Mohiuddin et al. |
| 2011/0282370 A1 | 11/2011 | Levine et al. |
| 2012/0226093 A1 | 9/2012 | Creighton |
| 2014/0088517 A1 | 3/2014 | Calderone |
| 2014/0148830 A1 | 5/2014 | Bowman |
| 2014/0303658 A1 | 10/2014 | Bonnette et al. |
| 2014/0309672 A1 | 10/2014 | Labropoulos et al. |
| 2015/0094748 A1 | 4/2015 | Nash et al. |
| 2015/0112376 A1 | 4/2015 | Molaei et al. |
| 2016/0013589 A1 | 1/2016 | Fu et al. |

(56) References Cited

U.S. PATENT DOCUMENTS

| | | |
|---|---|---|
| 2016/0089227 A1 | 3/2016 | Loh |
| 2016/0135829 A1 | 5/2016 | Holochwost et al. |
| 2016/0166266 A1 | 6/2016 | Nita |
| 2016/0220741 A1 | 8/2016 | Garrison et al. |
| 2017/0027604 A1 | 2/2017 | Wallace |
| 2017/0027611 A1* | 2/2017 | Adams ........... A61B 17/320016 |
| 2017/0105743 A1 | 4/2017 | Vale et al. |
| 2017/0112514 A1 | 4/2017 | Marchand et al. |
| 2017/0215900 A1 | 8/2017 | Lowinger et al. |
| 2017/0238950 A1 | 8/2017 | Yang et al. |
| 2017/0238953 A1 | 8/2017 | Yang et al. |
| 2018/0000510 A1 | 1/2018 | Nash et al. |
| 2018/0104054 A1 | 4/2018 | Chuter et al. |
| 2018/0207397 A1 | 7/2018 | Look et al. |
| 2018/0242989 A1 | 8/2018 | Nita |
| 2018/0256179 A1* | 9/2018 | Hayakawa ........... A61B 17/221 |
| 2018/0263642 A1 | 9/2018 | Nita |
| 2018/0280043 A1 | 10/2018 | Donegan |
| 2019/0008534 A1 | 1/2019 | Garrison et al. |
| 2019/0038300 A1 | 2/2019 | Savastano et al. |
| 2019/0046218 A1 | 2/2019 | Garrison et al. |
| 2019/0175210 A1 | 6/2019 | Wittens |
| 2019/0216476 A1 | 7/2019 | Barry et al. |
| 2019/0336149 A1 | 11/2019 | Yang et al. |
| 2020/0046368 A1 | 2/2020 | Merritt et al. |
| 2020/0187976 A1 | 6/2020 | Cartier et al. |
| 2020/0205845 A1 | 7/2020 | Yang et al. |
| 2020/0281611 A1 | 9/2020 | Kelly et al. |
| 2020/0281612 A1 | 9/2020 | Kelly et al. |
| 2020/0397957 A1 | 12/2020 | Teigen et al. |
| 2021/0045760 A1 | 2/2021 | Ulm, III |
| 2021/0045770 A1 | 2/2021 | Savastano et al. |
| 2021/0069468 A1 | 3/2021 | Keating et al. |
| 2021/0113224 A1 | 4/2021 | Dinh |
| 2021/0128185 A1 | 5/2021 | Nguyen et al. |
| 2021/0153883 A1 | 5/2021 | Casey et al. |
| 2021/0154433 A1 | 5/2021 | Casey et al. |
| 2021/0169510 A1 | 6/2021 | Randall |
| 2021/0196292 A1 | 7/2021 | Vale |
| 2021/0220006 A1 | 7/2021 | Mitchell |
| 2021/0228222 A1 | 7/2021 | Porter |
| 2021/0236150 A1 | 8/2021 | Arad Hadar |
| 2021/0275197 A1 | 9/2021 | Vale et al. |
| 2021/0275201 A1 | 9/2021 | Martin et al. |
| 2021/0316121 A1 | 10/2021 | Buck et al. |
| 2021/0316127 A1 | 10/2021 | Buck et al. |
| 2021/0378694 A1 | 12/2021 | Thress et al. |
| 2021/0393277 A1 | 12/2021 | Vale et al. |
| 2022/0000500 A1 | 1/2022 | Arad Hadar et al. |
| 2022/0143368 A1 | 5/2022 | Pulugurtha et al. |
| 2022/0273323 A1 | 9/2022 | Baron et al. |
| 2022/0338900 A1 | 10/2022 | Savastano et al. |
| 2023/0346416 A1 | 11/2023 | Berrada et al. |

FOREIGN PATENT DOCUMENTS

| | | |
|---|---|---|
| CN | 102006905 A | 4/2011 |
| CN | 102802718 A | 11/2012 |
| CN | 105688292 A * | 6/2016 |
| CN | 108135591 A | 6/2018 |
| EP | 2217158 B1 | 10/2014 |
| EP | 3141201 A1 | 3/2017 |
| JP | 2011505907 A | 3/2011 |
| WO | WO-0045716 A1 | 8/2000 |
| WO | WO-2009073409 A1 | 6/2009 |
| WO | WO-2015109176 A1 | 7/2015 |
| WO | WO-2016143846 A1 | 9/2016 |
| WO | WO-2018019829 A1 | 2/2018 |
| WO | WO-2018215840 A1 | 11/2018 |
| WO | WO-2019115809 A1 | 6/2019 |
| WO | WO-2019199931 A1 | 10/2019 |
| WO | WO-2019212984 A1 | 11/2019 |
| WO | WO-2020023541 A1 | 1/2020 |
| WO | WO-2020036809 A1 | 2/2020 |
| WO | WO-2020099386 A1 | 5/2020 |
| WO | WO-2021150348 A1 | 7/2021 |
| WO | WO-2021178696 A1 | 9/2021 |
| WO | WO-2021263033 A1 | 12/2021 |
| WO | WO-2022047324 A1 | 3/2022 |
| WO | WO-2022187156 A1 | 9/2022 |
| WO | WO-2022246071 A2 | 11/2022 |
| WO | WO-2022261448 A1 | 12/2022 |
| WO | WO-2023278495 A2 | 1/2023 |
| WO | WO-2023035013 A1 | 3/2023 |

OTHER PUBLICATIONS

Chinese Office Action for Chinese Application No. 2018800311609, dated Aug. 8, 2022, 16 pages.
European Office Action for European Application No. 19785481.3, mailed Feb. 27, 2023, 4 pages.
Extended European Search Report for Application No. EP19785481.3 dated Oct. 20, 2021, 6 pages.
Extended European Search Report for European Application No. 18784090.5, mailed Oct. 30, 2020, 6 pages.
International Search Report and Written Opinion for Application No. PCT/US2022/018182, mailed Jul. 21, 2022, 22 pages.
International Search Report and Written Opinion for International Application No. PCT/US2018/026831, mailed Jul. 26, 2018, 14 pages.
International Search Report and Written Opinion for International Application No. PCT/US2019/026737, mailed Jul. 30, 2019, 12 pages.
Karthikeshwar et al. "The Use of Mechanical Thrombectomy Devices in the Management of Acute Peripheral Arterial Occlusive Disease," Journal of Vascular and Interventional Radiology, vol. 12, Issue 4. (Apr. 2001). p. 405-411.
Office Action for Australian Application No. 2018250821, dated Feb. 27, 2023, 4 pages.
Office Action for Japanese Application No. JP20200504292 dated Mar. 1, 2023, 4 pages.
Office Action for Japanese Application No. JP2020504292, mailed on May 11, 2022, 5 pages.
Office Action for U.S. Appl. No. 16/156,519, mailed Aug. 5, 2020, 13 pages.
Office Action for U.S. Appl. No. 17/027,048, mailed Jan. 12, 2021, 22 pages.
Supplemental Extended European Search Report regarding European Application No. 18751745.3, dated Nov. 20, 2020, 11 pages.
Extended European Search Report dated May 8, 2023 in European Application No. 23156405.5, 5 pages.
International Preliminary Report on Patentability for International Application No. PCT/US2022/018182 dated Sep. 14, 2023, 15 pages.
Non-Final Office Action for U.S. Appl. No. 18/241,588 dated Feb. 16, 2024, 23 pages.

* cited by examiner

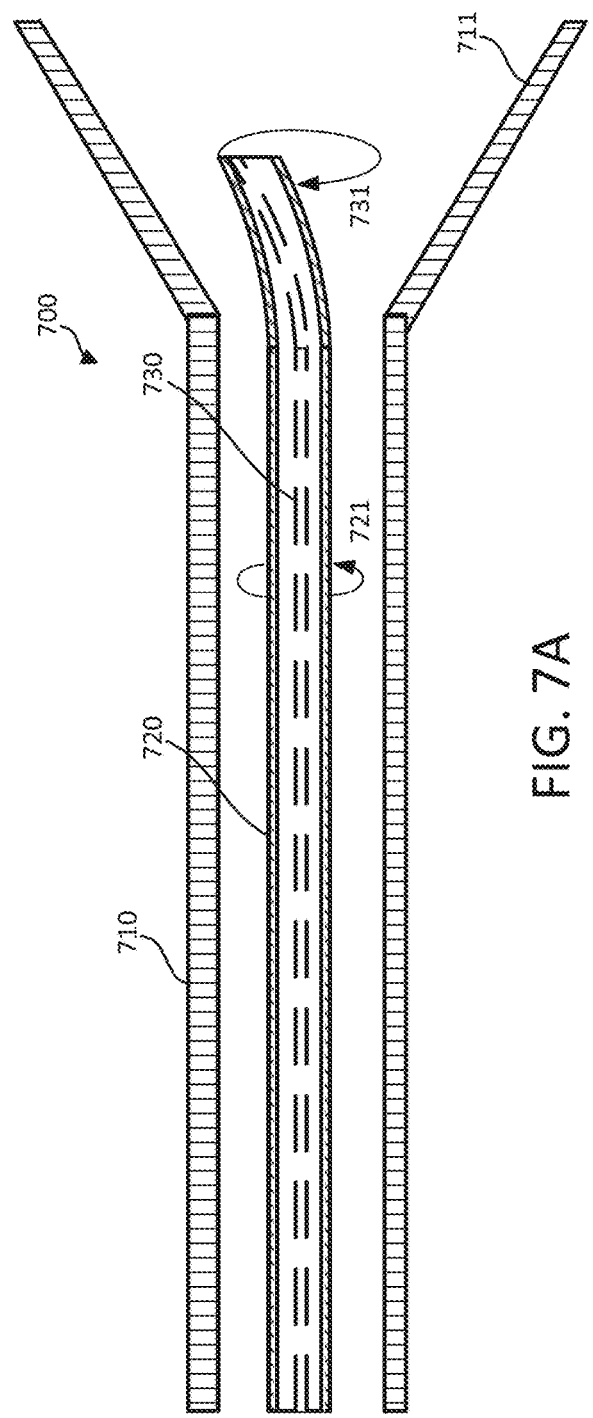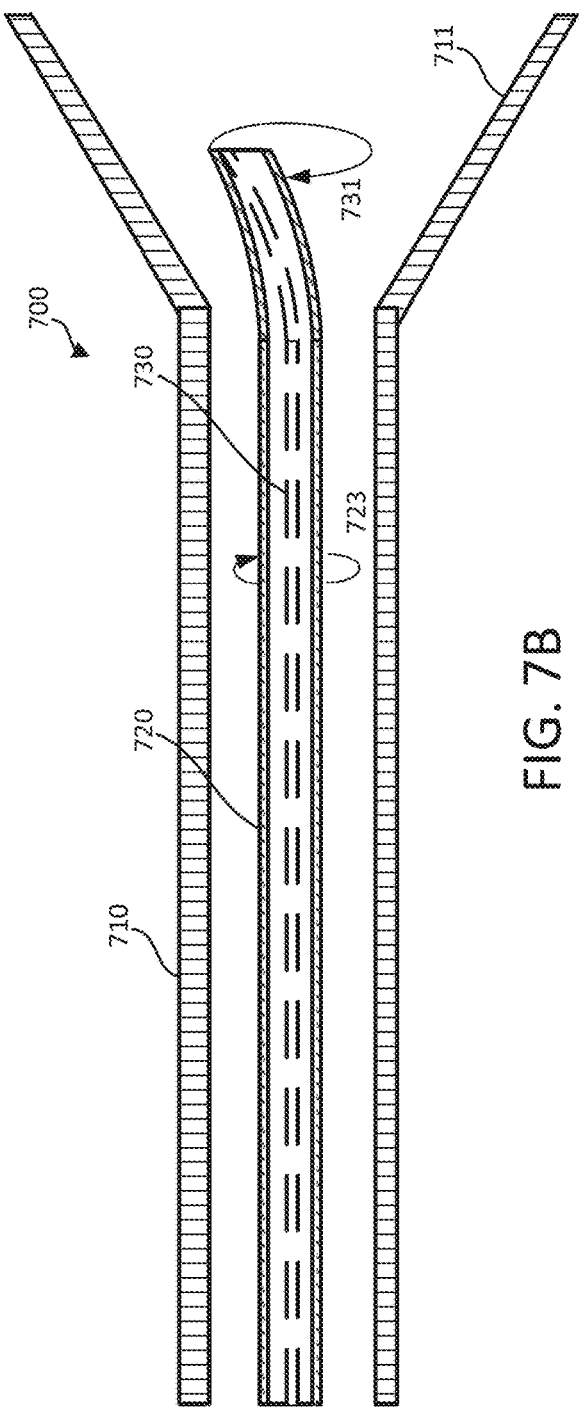

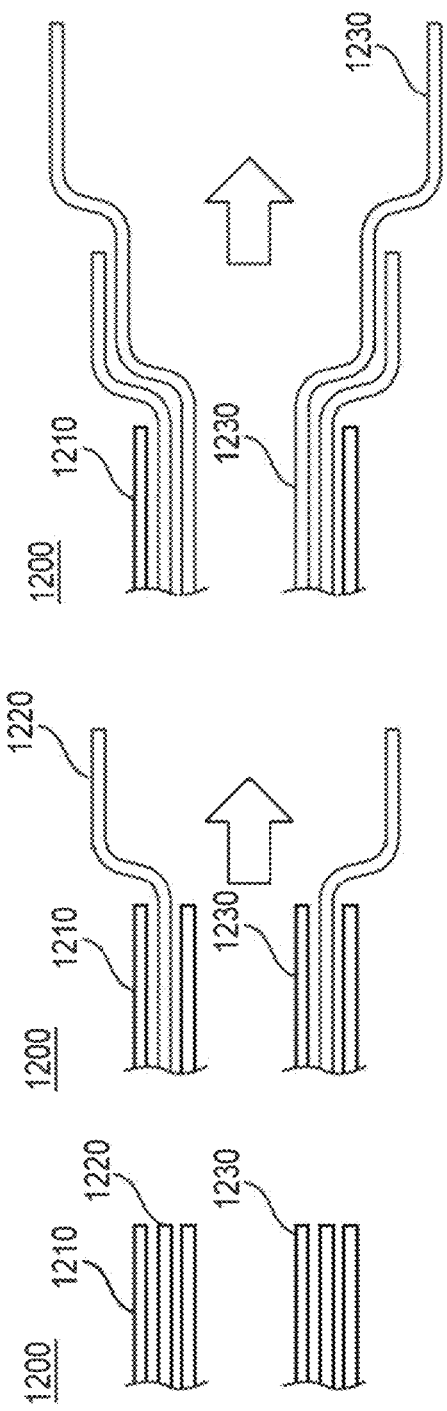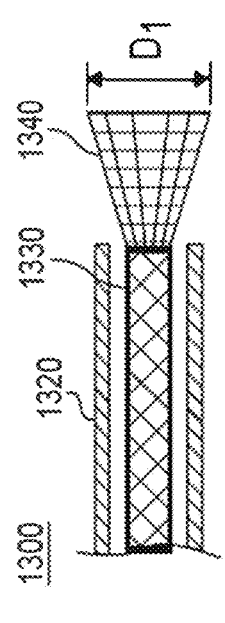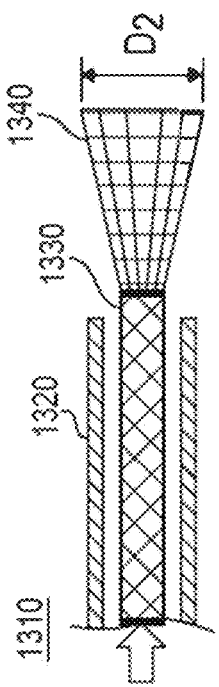

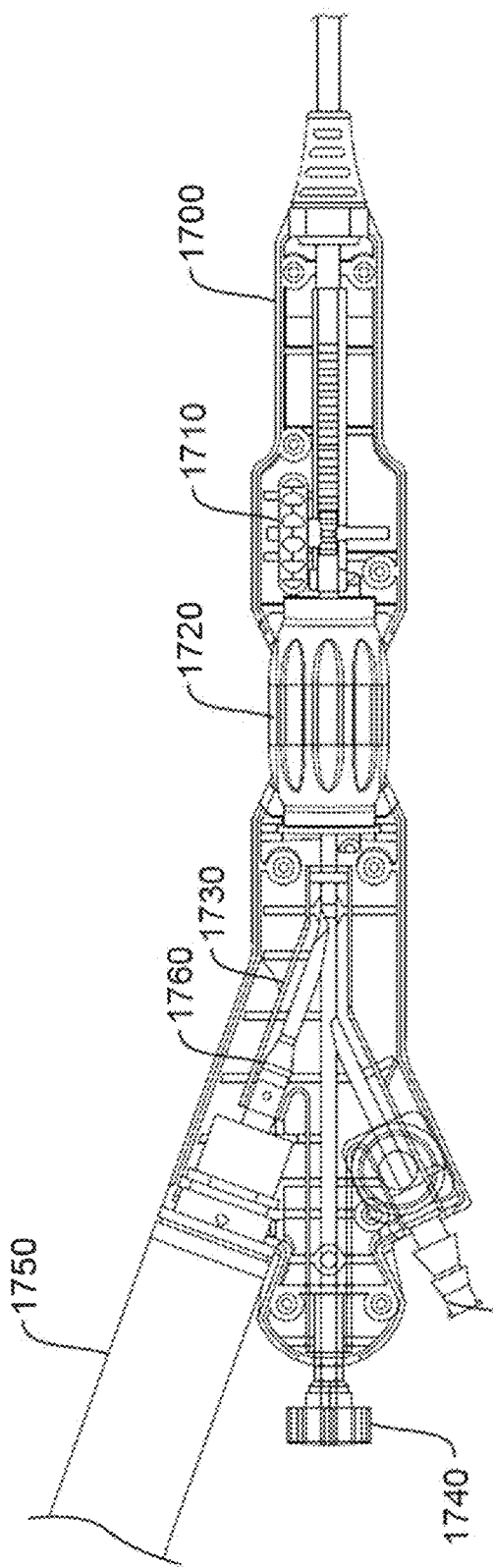
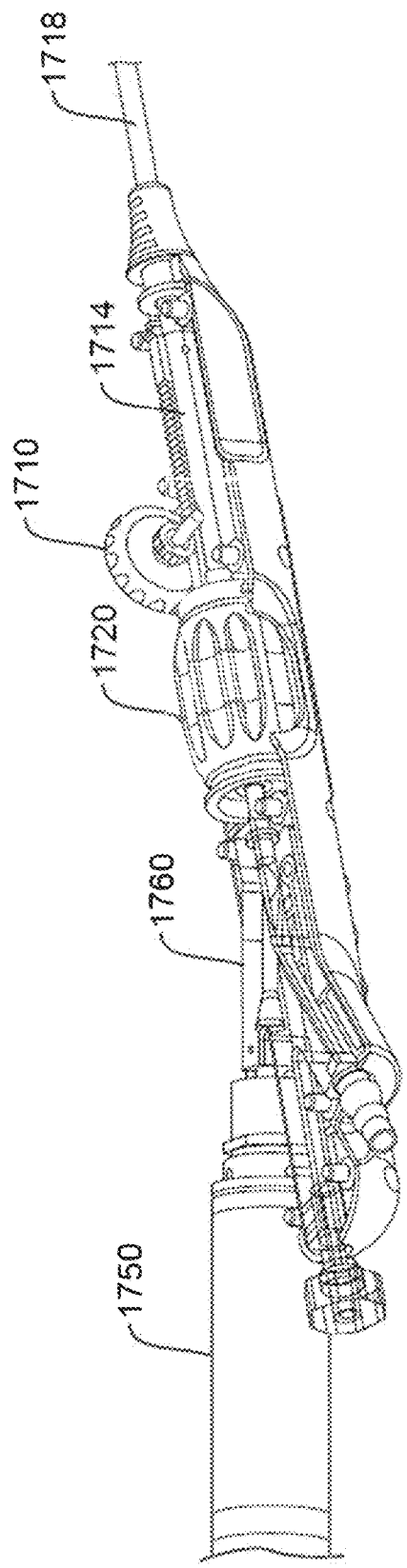
FIG. 17A
FIG. 17B

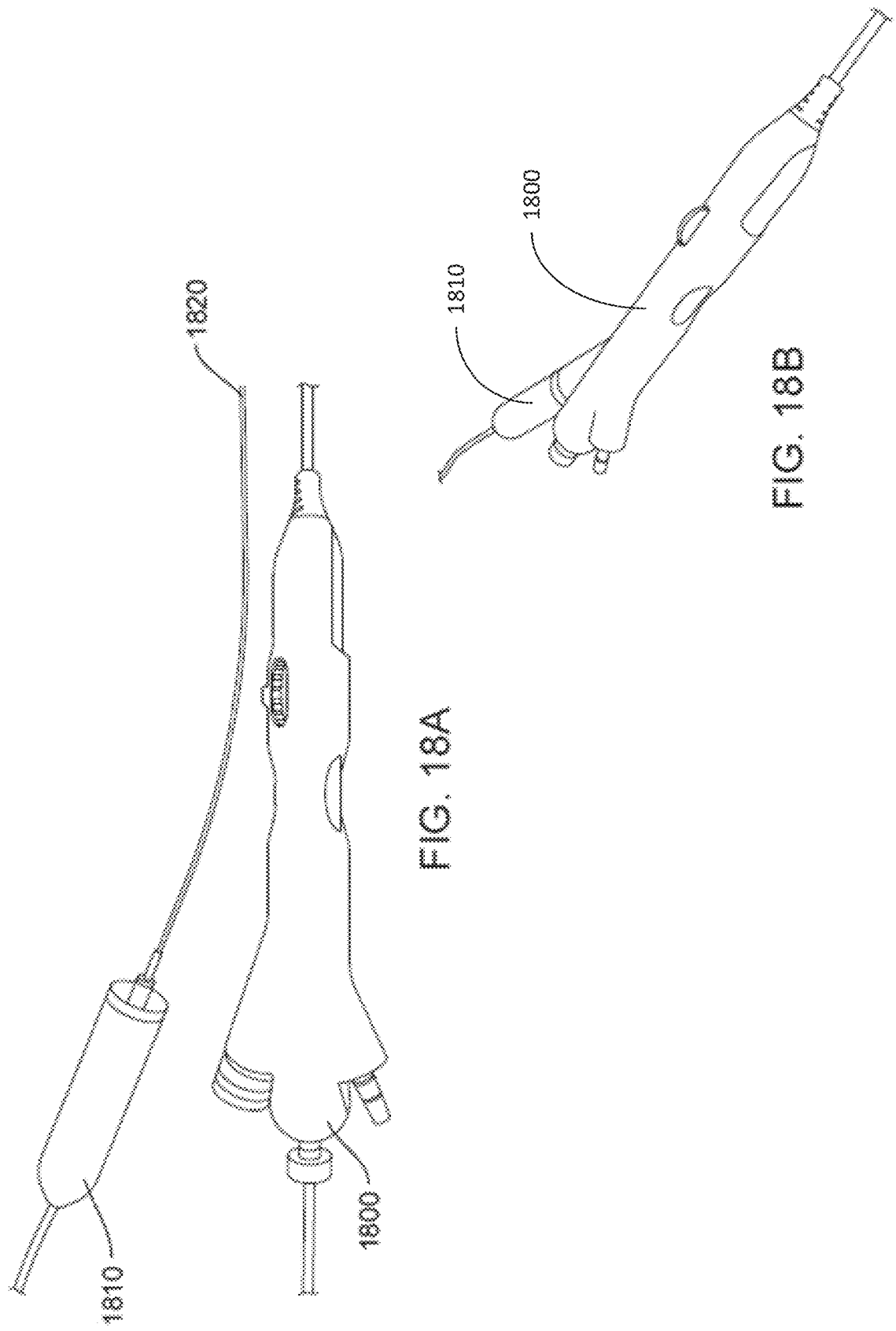

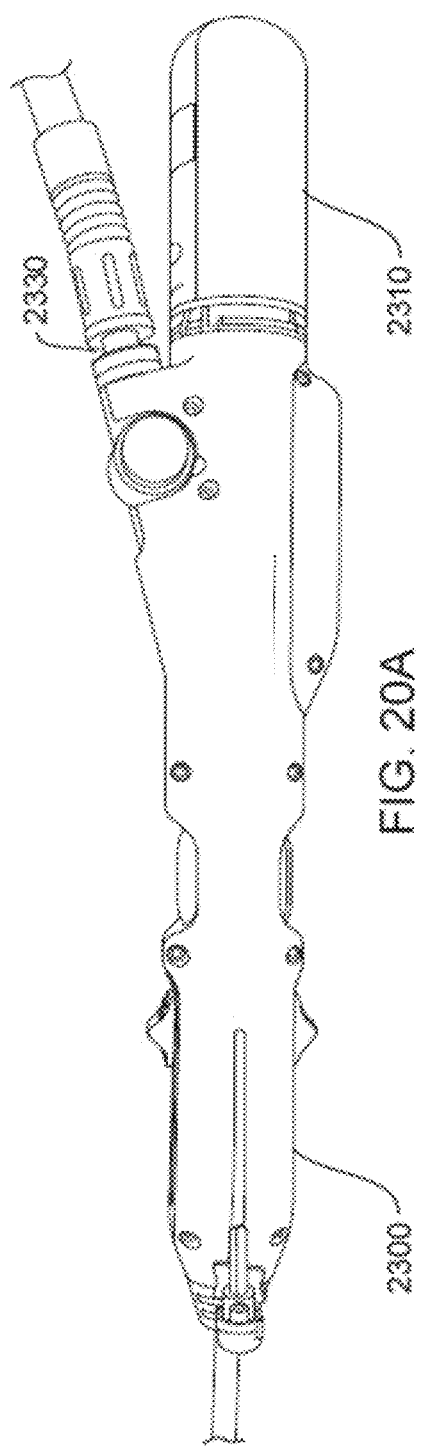
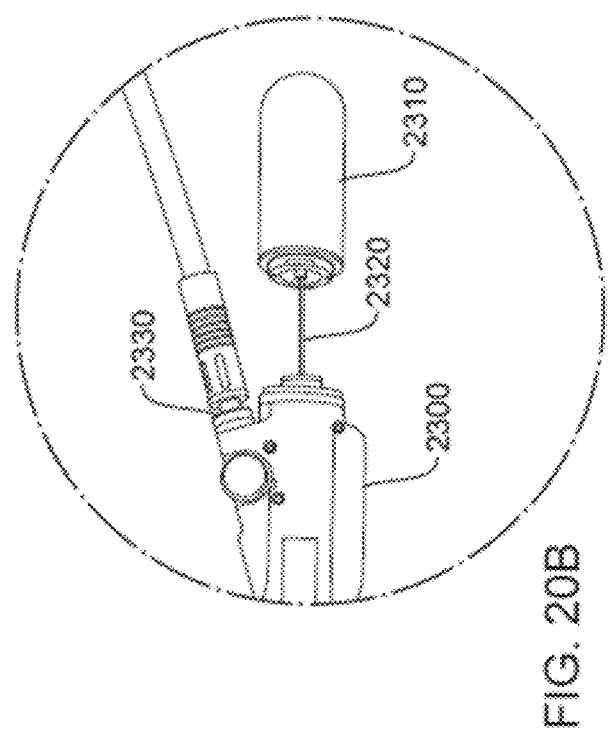
FIG. 20A
FIG. 20B

THROMBECTOMY SYSTEMS AND DEVICES WITH ASPIRATION, AND METHODS OF USE THEREOF

CROSS-REFERENCE TO RELATED APPLICATIONS

This application is a continuation of U.S. patent application Ser. No. 17/682,949, filed Feb. 28, 2022, which claims priority to U.S. Provisional Patent Application No. 63/155,191, filed Mar. 1, 2021, and U.S. Provisional Patent Application No. 63/170,346, filed Apr. 2, 2021.

TECHNICAL FIELD

The embodiments described herein relate generally to thrombectomy systems and devices with aspiration, and methods of use thereof.

BACKGROUND

Thrombosis is the formation of a blood clot inside a blood vessel that may obstruct the flow of blood through the circulatory system. The formation of a thrombus can occur within the heart or any artery or vein in the body, leading to a myriad of medical problems such as myocardial infarction, stroke, pulmonary embolism, and deep venous thrombosis. Rapid thrombectomy is frequently needed in cases of: 1) obstruction of arteries of delicate organs, such as the heart or the brain (e.g., ischemic stroke); 2) large clots interrupting blood flow in major vessels or causing severe symptoms; or 3) when systemic delivery of the drugs is too risky.

Conventional thrombectomy devices for removing clots from an occluded vessel include mechanical thrombectomy devices such as aspiration catheters. Aspiration catheters, however, can be ineffective with respect to large clot burdens, organized (e.g., tough) clots, and clots extending from large to small vessels. Other mechanical thrombectomy devices, including those with distal cutting or macerating mechanisms directly disposed in a vessel lumen, can cause distal embolization of clots and vascular damage. Therefore, it is desirable to have improved systems, devices, and methods for removing material (e.g., blood clots) from patient vasculature.

SUMMARY

Described herein are systems, devices, and methods for treating a thrombosis.

In some embodiments, an apparatus may comprise a sleeve defining a first lumen, and an aspiration catheter defining a second lumen, the aspiration catheter slidably disposed within the first lumen, the aspiration catheter including a proximal end coupleable to a vacuum source configured to apply a vacuum pressure within the second lumen to draw a thrombus into the second lumen, and an expandable tip configured to transition between a retracted configuration in which the expandable tip is constrained within the sleeve and an expanded configuration in which at least a portion of the expandable tip is disposed distal to the sleeve. The expandable tip in the expanded configuration can have a funnel-shaped profile that gradually increases in diameter from a proximal end of the expandable tip to a distal end of the expandable tip. The expandable tip in the expanded configuration can have a pinch strength of between about 0.4 lb and about 3 lb at or near a patient body temperature (e.g., between about 35° C. and about 40° C.) such that the expandable tip in the expanded configuration is configured to withstand collapse from pressure gradients being generated within the expandable tip as the vacuum pressure acts on the thrombus within the expandable tip. The expandable tip in the expanded configuration can be further configured to be retractable into the sleeve in response to a retracting force of between about 0.5 lbs and about 4.0 lbs.

In some embodiments, the pinch strength of the expandable tip in the expanded configuration can be between about 0.4 lb and about 3.0 lb. In some embodiments, the retracting force for retracting the expandable tip into the sleeve can be between about 0.5 lbs and about 2.0 lbs. In some embodiments, the expandable distal tip can include a metallic frame and a coating that is disposed over the metallic frame. In some embodiments, the metallic frame defines a plurality of open cells, and the coating as an inner layer and an outer layer that connect to one another at the plurality of open cells. In some embodiments, each of the plurality of open cells has an area of at least about 0.5 mm$^2$ to enable the inner and outer layers of the coating to connect to one another at each open cell.

In some embodiments, the expandable distal tip can include a metallic frame that defines a plurality of open cells, the plurality of open cells increasing in size from the proximal end to the distal end of the expandable tip. In some embodiments, the metallic frame can further include an atraumatic wave-shaped (e.g., U-shaped, undulating) ring at the distal end of the expandable tip. In some embodiments, open cells of the plurality of open cells disposed at the proximal end of the expandable tip can have a length of at least about 2.0 mm and open cells of the plurality of open cells disposed at the distal end of the expandable tip can have a length of about less than about 5.0 mm when the expandable tip is in the retracted configuration. In some embodiments, open cells of the plurality of open cells disposed at the proximal end of the expandable tip can have a proximal angle of at least about −10° and open cells of the plurality of open cells disposed at the distal end of the expandable tip can have a proximal angle of less than about 40°, when the expandable tip is in the expanded configuration.

In some embodiments, the aspiration catheter defines a plurality of openings disposed near the proximal end of the expandable tip, the plurality of openings configured to increase fluid available to mix with the thrombus to improve flow of the thrombus proximally through the second lumen. In some embodiments, a flexible shaft can have a distal end disposable within the expandable tip of the aspiration catheter, the distal end of the flexible shaft configured to rotate within the expandable tip when the expandable tip is in the expanded configuration to engage and break portions of the thrombus disposed within the expandable tip.

In some embodiments, an apparatus may comprise a sleeve defining a first lumen, and an aspiration catheter defining a second lumen, the aspiration catheter including a proximal end coupleable to a vacuum source configured to apply a vacuum pressure within the second lumen to draw a thrombus from a vessel into the second lumen, an expandable tip disposable within the vessel, the expandable tip configured to transition between a retracted configuration in which the expandable tip is constrained within the sleeve and an expanded configuration in which at least a portion of the expandable tip is disposed distal to the sleeve, the expandable tip in the expanded configuration can have a funnel-shaped profile that gradually increases in diameter from a proximal end of the expandable tip to a distal end of the expandable tip, and an elongate body extending between the proximal end of the aspiration catheter and a proximal end of the expandable tip. The elongate body can have a linear proximal section and a flexible curved section disposed near the expandable tip, the elongate body configured to translate within the first lumen, the elongate body coupled to an actuator configured to selectively control a degree of extension of the memory-set curved section from the distal end of the sleeve to change a degree of curvature of the memory-set curved section and a position of the expandable tip within the vessel.

In some embodiments, the elongate body can be further configured to rotate within the first lumen to change the position of the expandable tip within the vessel. In some embodiments, the memory-set curved section, when at least partially extended from the distal end of the sleeve, is configured to have a radius of curvature between about 10 mm and about 40 mm. In some embodiments, the sleeve can have a curved section. In some embodiments, the elongate body can be further configured to rotate within the first lumen to change a relative orientation of the memory-set curved section with respect to the curved section of the sleeve such that a total angular deviation of the aspiration catheter can be adjusted. In some embodiments, the expandable distal tip can include a metallic frame and a coating that is disposed over the metallic frame. In some embodiments, the expandable distal tip can include a metallic frame that defines a plurality of open cells, the plurality of open cells increasing in size from the proximal end to the distal end of the expandable tip.

In some embodiments, the metallic frame can further include an atraumatic wave-shaped ring at the distal end of the expandable tip. In some embodiments, open cells of the plurality of open cells disposed at the proximal end of the expandable tip can have a length of about 2 mm and open cells of the plurality of open cells disposed at the distal end of the expandable tip can have a length of about 5 mm when the expandable tip is in the retracted configuration. In some embodiments, open cells of the plurality of open cells disposed at the proximal end of the expandable tip can have a proximal angle of about −10° and open cells of the plurality of open cells disposed at the distal end of the expandable tip can have a proximal angle of about 40° when the expandable tip is in the expanded configuration. In some embodiments, a flexible shaft having a distal end disposable within the expandable tip of the aspiration catheter, the distal end of the flexible shaft configured to rotate within the expandable tip when the expandable tip is in the expanded configuration to engage and break portions of the thrombus disposed within the expandable tip.

In some embodiments, a system may comprise an aspiration catheter defining a lumen, the aspiration catheter including a proximal end coupleable to a vacuum source configured to apply a vacuum pressure within the lumen to draw a thrombus from a vessel into the lumen, an expandable tip configured to transition between a retracted configuration in which the expandable tip is constrained within an outer sleeve and an expanded configuration in which at least a portion of the expandable tip is disposed distal to the outer sleeve, the expandable tip in the expanded configuration having a funnel-shaped profile that gradually increases in diameter from a proximal end of the expandable tip to a distal end of the expandable tip, a flexible shaft disposable within the lumen of the aspiration catheter, the flexible shaft configured to extend from the proximal end of the aspiration catheter to the expandable tip such that a distal end of the flexible shaft is disposed in the expandable tip, the distal end of the flexible shaft having a non-linear configuration and being configured to rotate within the expandable tip when the expandable tip is in the expanded configuration to engage and break portions of the thrombus disposed within the expandable tip.

In some embodiments, a handle assembly can be coupled to a proximal end of the aspiration catheter, the handle assembly including a set of actuators for independently rotating the aspiration catheter and/or translating an outer sleeve relative to the aspiration catheter. In some embodiments, a drive system can be coupled to a proximal end of the flexible shaft and configured to rotate the flexible shaft, the drive system being releasably coupleable to the handle assembly.

In some embodiments, an activation element can be configured to activate the vacuum pressure and to activate the drive system to rotate the flexible shaft. In some embodiments, the activation element can be a button, the button configured to (1) activate the vacuum pressure in response to being depressed a first amount and (2) activate the drive system in response to being depressed a second amount greater than the first amount. In some embodiments, the outer sleeve and the aspiration lumen defining an annular space configured to deliver a fluid into an area near the thrombus.

In some embodiments, an apparatus may comprise a handle assembly, a catheter extending distally from the handle assembly and having an expandable distal tip, the catheter disposable within a body lumen near a thrombus, a sleeve disposed over at least a portion of the catheter including the expandable distal tip, a vacuum port coupled to the handle assembly and configured to couple to a vacuum source such that a negative pressure can be applied to a lumen of the catheter, an adjustment mechanism coupled to the handle assembly and configured to move at least one of the catheter or the sleeve relative to each other such that the expandable distal tip can move between a first position within the sleeve and a second position distal to the sleeve. In some embodiments, the expandable distal tip may be configured to have an unexpanded configuration in the first position and an expanded configuration in the second position. The expandable distal tip in the expanded configuration may have a maximum diameter greater than a diameter of the sleeve. The expandable distal tip may be configured to remain in the expanded configuration when negative pressure is being applied to the lumen of the catheter such that the thrombus can be drawn into the expandable distal tip.

In some embodiments, the expandable distal tip may include a plurality of sections, each section from the plurality of sections having a different structure. In some embodiments, the expandable distal tip may be formed from a metallic tubular member, each section from the plurality of sections having a different cut pattern. In some embodiments, each section from the plurality of sections may have a different strength such that a more distal section from the plurality of sections has a greater strength than a more proximal section from the plurality of sections.

In some embodiments, the expandable distal tip may include a bend such that a distal opening of the expandable distal tip is angled relative to a longitudinal axis of the catheter. In some embodiments, the adjustment mechanism may be a first adjustment mechanism, the apparatus further comprising: a second adjustment mechanism configured to rotate the catheter such that the expandable distal tip can rotate to position the distal opening of the expandable distal tip at different lateral positions relative to the longitudinal axis of the catheter. In some embodiments, the second adjustment mechanism may be a wheel or a knob. In some embodiments, the adjustment mechanism may be a slider, a wheel, or a knob.

In some embodiments, the expandable distal tip in the expanded configuration may have a funnel shape. In some embodiments, the expandable distal tip in the expanded configuration may have a plurality of stepped sections, each stepped section from the plurality having a different diameter in which a more distal stepped section has a larger diameter than a more proximal stepped section.

In some embodiments, a system my include the apparatus as described in the embodiments herein, and a shaft assembly, the shaft assembly including: a flexible shaft disposable within the lumen of catheter, the flexible shaft including a distal end configured to be positioned proximal of a distal end of the catheter within the expandable distal tip, the flexible shaft configured to be rotated such that the distal end of the flexible shaft can rotate axially about a longitudinal axis of the flexible shaft and orbitally about a longitudinal axis of the catheter when negative pressure is being applied to the lumen of the catheter to cause the thrombus to break and be drawn proximally within the lumen of the catheter.

In some embodiments, the shaft assembly may further include: a stylet disposable within a lumen of the flexible shaft, the stylet comprising a shaped distal end that has a greater bending stiffness than at least a portion of the flexible shaft such that the shaped distal end, when disposed within the lumen of the flexible shaft, can impart a shape onto the flexible shaft, the shaft and the stylet configured to be rotated such that the distal end of the flexible shaft can rotate axially about the longitudinal axis of the flexible shaft and orbitally about the longitudinal axis of the catheter. In some embodiments, a drive system configured to rotate the shaft.

In some embodiments, a method may comprise navigating a distal end of an aspiration catheter within a vessel to a site including a thrombus, expanding the distal end of the aspiration catheter, navigating a distal end of a flexible shaft through a lumen of the aspiration catheter, positioning the distal end of the flexible shaft proximal to the distal end of the aspiration catheter, applying vacuum pressure to the lumen of the aspiration catheter such that the thrombus is drawn into the expanded distal end of the aspiration catheter, and rotating the flexible shaft using a drive system to reshape the thrombus and draw the thrombus proximally within the lumen of the aspiration catheter.

In some embodiments, expanding the distal end of the aspiration catheter may include moving at least one of a sleeve disposed over the distal end of the catheter or the catheter relative to the other to allow the distal end of the catheter to self-expand. In some embodiments, the method may include navigating a stylet with the flexible shaft through the lumen of the aspiration catheter, the stylet including at least a portion disposable within a lumen of the flexible shaft, and rotating the stylet with the flexible shaft using the drive system.

BRIEF DESCRIPTION OF THE DRAWINGS

FIGS. 7A and 7B are detailed side cross-sectional views of a catheter and shaft assembly of a thrombectomy system, according to embodiments.

FIGS. 12A-12C are cross-sectional side views of a distal end of a catheter assembly of a thrombectomy system, according to embodiments.

FIGS. 13A and 13B are cross-sectional side views of a distal end of a catheter assembly of a thrombectomy system, according to embodiments.

FIG. 17A is a cross-sectional side view of a handle of a thrombectomy system, according to embodiments. FIG. 17B is a cross-sectional perspective view of the handle of the thrombectomy system depicted in FIG. 17A.

FIGS. 18A-18B are images of a handle of a thrombectomy system, according to embodiments.

FIGS. 20A-20B are images of a handle of a thrombectomy system, according to embodiments.

DETAILED DESCRIPTION

Described herein are systems, devices, and methods for removing material (e.g., a blood clot) from a vessel of a subject. Systems, devices, and methods described herein include aspiration catheters with expandable tips and a shaft disposable within the aspiration catheters configured to rotate and facilitate thrombus ingestion and removal. In some embodiments, the rotating shafts described herein can be configured to generate hydrodynamic forces that facilitate proximal movement of a thrombus. The systems and devices described herein may be designed to be compact and flexible for enhanced navigation and steering for acute pulmonary embolisms. For example, the thrombectomy devices described herein may comprise a low profile (e.g., less than about 16 French) configured to navigate through the heart and with the capacity to remove large volume thrombi efficiently with a short procedure time (e.g., up to about 400 ml).

Figure 1:
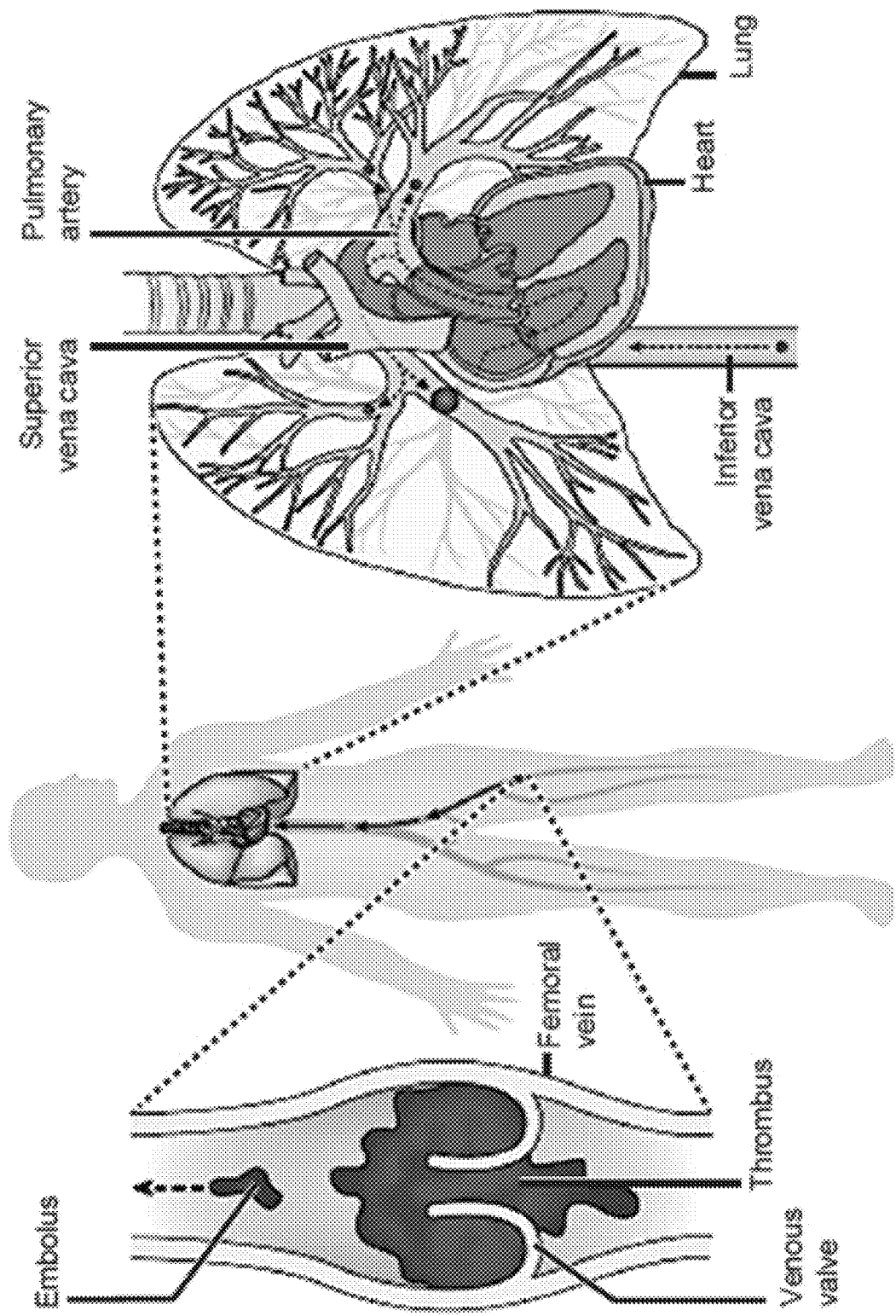
FIG. 1 is a diagram of a pulmonary embolus in patient vasculature, according to embodiments.

In some embodiments, systems, devices, and methods described herein can be used to remove an embolus (e.g., blood clot) such as shown in FIG. 1. In some embodiments, systems, devices, and methods described herein can be used to remove an embolus (e.g., blood clot) within larger body vessels, e.g., for treating pulmonary embolism.

In some embodiments, a thrombectomy system as described herein may include a shaft disposed within a lumen of an aspiration catheter. The shaft may be configured for high-speed rotation that may generate a combination of axial rotation and orbital motion at a tip of the shaft about an inner circumference of the catheter. In some embodiments, the tip of the shaft can be disposed within a larger section (e.g., an expandable tip) of the aspiration catheter. In such embodiments, the tip of the shaft can be configured to engage with and reshape a clot, thereby facilitating its proximal withdrawal from the body. In some embodiments, the tip of the shaft, in response to being rotated, can generate a pressure differential in conjunction with the vacuum produced by the aspiration catheter to withdraw the clot proximally within the catheter lumen. The rotating shaft may form or take on a generally helical shape configured to facilitate clot removal by physically reshaping (e.g., compressing, breaking, twisting, elongating) the clot and/or reducing friction along the inner diameter of the catheter (e.g., by wiping off the clot from the inner diameter of the catheter). The helical shape can generate a combination of motion at a tip of the shaft, including orbital motion about a longitudinal axis of the aspiration catheter and rotational motion about a longitudinal axis of the shaft. The orbital motion of the shaft may reduce or prevent static friction, as well as reshape a clot to enable ingestion. The orbital motion can also further apply hydrodynamic and direct mechanical forces on the clot at lower relative speeds. Suitable examples of such aspiration catheter systems are described in International Application Serial No. PCT/US2019/026737, filed on Apr. 10, 2019, and titled "HYDRODYNAMIC VORTEX ASPIRATION CATHETER," and U.S. Application Ser. No. 63/155,191, filed on Mar. 1, 2021, and titled "SYSTEMS, DEVICES, AND METHODS FOR REMOVING THROMBOEMBOLIC MATERIAL WITH COAXIAL INDEPENDENT ROTATIONAL ELEMENTS," the disclosure of each which is hereby incorporated by reference in its entirety.

Systems, devices, and methods described herein can be used to generate combined orbital and rotational motion of a shaft within an aspiration catheter at any desired speed. In some embodiments, systems, devices, and methods can be well suited for removing occluding material (e.g., blood clots) from one or more vessels of the pulmonary arteries. For example, the systems and devices described herein enable thrombus removal through aspiration through a large diameter vessel. For example, pulmonary veins may vary significantly in diameter (e.g., between about 4 mm and about 24 mm) and may change diameters abruptly. Clot burden and composition may also be variable and access routes may not be standardized.

In some embodiments, high speed rotation of the shaft about its longitudinal axis is used to induce the helical shape of the shaft and generate the orbital and rotational motion of the shaft. But such method of generating the orbital and rotational motion of the shaft can have certain shortcomings. For example, the generation of the orbital motion can be dependent on the speed of the axial rotation, the torque load on the shaft from friction with the occluding material (e.g., clot) and with an inner surface of the aspiration catheter, the stiffness of the shaft, among other factors. Moreover, in practice, significantly high speeds are needed to ensure that the shaft takes on an orbital motion, especially when traversing more tortuous anatomy. Such high speeds can increase the risk of torsional failure of the catheter and loss of vacuum seal, as well as increased vibration, noise, and heat generation.

As such, in some embodiments, a thrombectomy system can include a shaped shaft, such as, for example, a shaft with a bent, curved, or other non-linear portion. The non-linear portion of the shaft can be disposed near or at a distal end of the shaft, such that when the shaft is rotated, the non-linear portion can facilitate orbital and rotational motion of the shaft. In some embodiments, the non-linear portion of the shaft can be positioned within an enlarged distal end of an aspiration catheter (e.g., an expandable tip, such as, for example, a funnel-shaped tip) such that the end of the shaft can engage with and reshape a thrombus captured within the enlarged distal end of the aspiration catheter.

Alternatively, in some embodiments, a system can include an aspiration catheter, a shaft, and a shaped stylet or second shaft disposed within and/or about the shaft. The shaped stylet can be configured to cause the shaft to take on a non-linear shape, e.g., have a bent, curved, or other non-linear portion. The shaft can be coupled to a first driving mechanism that controls a rotational motion of the shaft about its longitudinal axis. The stylet (e.g., a second shaft disposed within the shaft) can be coupled to a second driving mechanism that controls an orbital motion of the shaft about a longitudinal axis of the aspiration catheter. Alternatively, in some embodiments, the stylet and the shaft can be coupled to the same driving mechanism but using different coupling elements (e.g., different gears that set different gear ratios), which allow the rotational motion to be different from the orbital motion. The stylet can be shaped to impart a shape on the shaft that induces orbital motion of the shaft when the stylet is rotated. In some embodiments, the system can be configured to generate orbital motion of the shaft within the catheter independently of axial rotation of the shaft. For example, a speed and/or direction of orbital motion and can be controlled independently of a speed and/or direction of axial rotation. Systems, devices, and methods described herein can facilitate clot removal at lower axial rotational speeds, e.g., because the shaft does not need to be rotated at high speeds to induce orbital motion. With such systems, devices, and methods, orbital motion can also be substantially independent of torque load and friction.

In some embodiments, a stylet as described herein can be disposed within a lumen of a rotating shaft. The stylet can be configured to rotate within the shaft lumen to generate orbital motion of the shaft within the catheter lumen. The shaft may be configured to rotate simultaneously with stylet rotation to generate combined orbital and rotational motion of the shaft (e.g., along a distal portion of the shaft). The motion of the shaft can cause the shaft to mechanically interact with the portion of an occluding material (e.g., blood clot) suctioned into the catheter to reshape the occluding material. For example, the shaft can take on both rotational and orbital motion (e.g., including a corkscrew-like shape), which can cause occluding material drawn into a lumen of the aspiration catheter to separate from an inner wall of the catheter and prevent build-up of static friction between the occluding material and catheter. With the stylet driving the orbital motion of the shaft, the axial rotational speeds of the shaft can be reduced. Such can enable the use of a less complex drive system and increase reliability of the system.

In some embodiments, the aspiration catheter, shaft, and/or stylet can be movable (e.g., translatable) along a longitudinal axis of the system relative to one another. In some embodiments, one or more locking mechanisms (e.g., stops, clamps, etc.) may be configured to restrict translation of one or more of the shaft or stylet relative to the catheter. In some embodiments, the shaft and/or stylet may have a fixed or predetermined length such that the shaft and/or stylet can be inserted up to a predetermined depth into the aspiration catheter (e.g., advanced to a predetermined position relative to the aspiration catheter).

In some embodiments, an aspiration catheter may include a distal tip configured to transition from a first configuration (e.g., retracted or compressed configuration) in which the distal tip has a first diameter to a second configuration (e.g., expanded configuration) in which the distal tip has a second diameter that is larger than the first diameter. In such embodiments, the larger expanded end of the aspiration catheter can be configured to draw at least a portion of clot or thrombus within a vessel into the tip of the aspiration catheter. A shaft disposed within the aspiration catheter can then be used to engage with and reshape the clot or thrombus to facilitate proximal movement of the clot or thrombus. Such embodiments can be particularly suitable for use in pulmonary embolism applications, which involve larger diameter vessels and therefore removal of larger clots and thrombi. The larger distal end of the aspiration catheter can be configured to capture the larger clots and thrombi, while a rotating shaft within the aspiration catheter can be configured to reshape the clots and thrombi such that they can be aspirated out via the lumen of the aspiration catheter.

In some embodiments, an aspiration catheter may include a bent, curved, or other non-linear portion that imparts an angle to a tip of the aspiration catheter. For example, the aspiration catheter can include a curve disposed adjacent to or near a larger distal end of the aspiration catheter (e.g., an expandable distal tip, such as, for example, a funnel-shaped tip), and the amount of curvature can dictate a direction that the distal end of the aspiration catheter opens toward. Such curvature or other non-linearity of the aspiration catheter can facilitate navigation of the aspiration catheter and/or seeking of a clot. In some embodiments, the degree of curvature or non-linearity of the aspiration catheter can be controlled using an outer sleeve. The outer sleeve can have greater strength than the aspiration catheter and, when placed over the aspiration catheter, can cause the aspiration catheter to be linear or substantially linear. The sleeve can be withdrawn to incrementally expose the curve or non-linear portion of the aspiration catheter to enable the catheter to take on different degrees of curvature. In such instances, the catheter can be configured to have a variable curved tip for purposes of navigation and/or seeking of a clot. In some embodiments, the aspiration catheter with the curved or non-linear portion can be configured to rotate about its longitudinal axis to direct a distal opening of the aspiration catheter toward different sides of a vessel, e.g., facilitating capture of different portions of a larger clot.

Further details of thrombectomy systems, including aspiration catheters with larger diameter tips and rotating shafts, are described below with reference to the figures.

I. System

Figure 2A:
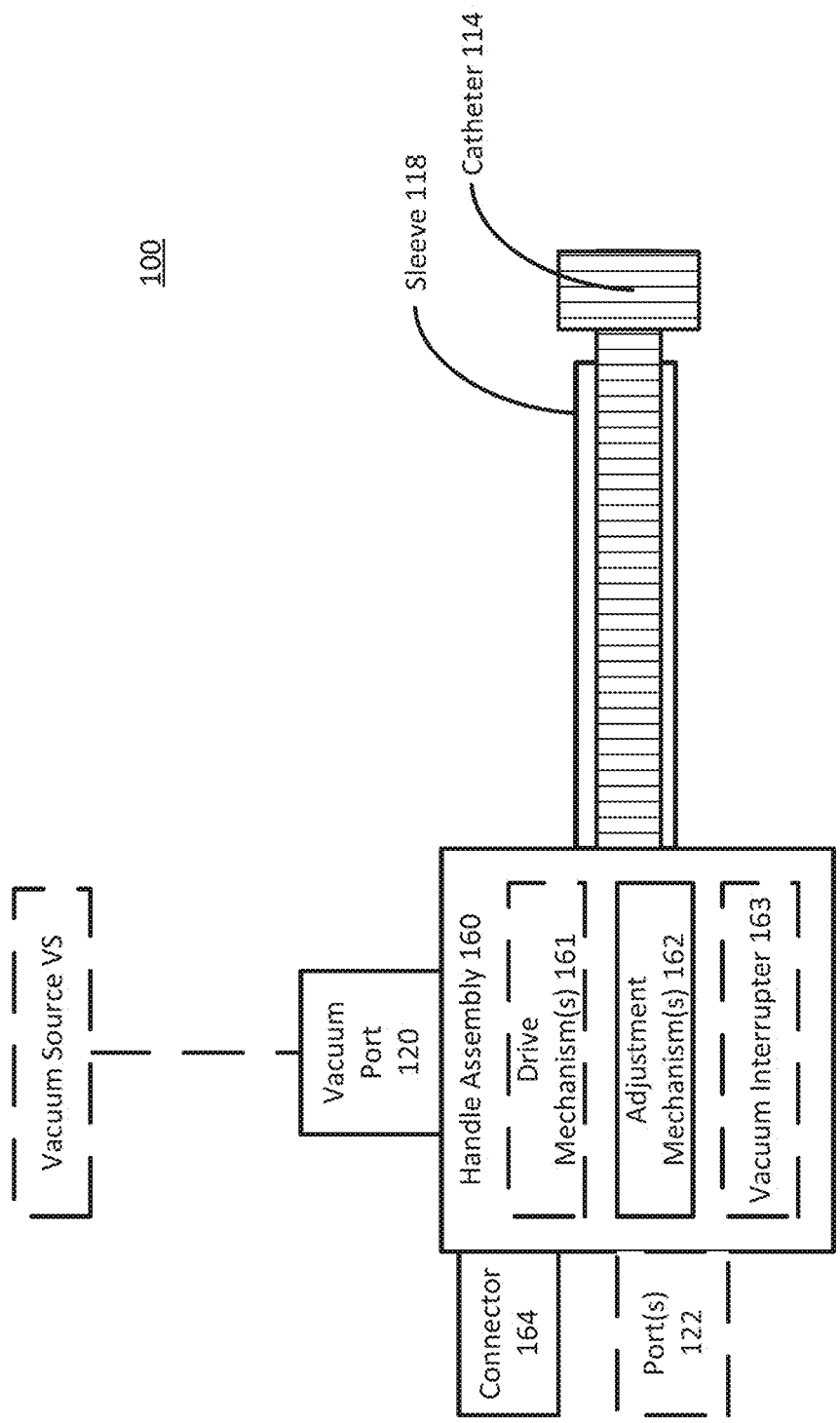
FIGS. 2A and 2B are schematic diagrams of a catheter assembly of a thrombectomy system, according to embodiments.
Figure 2B:
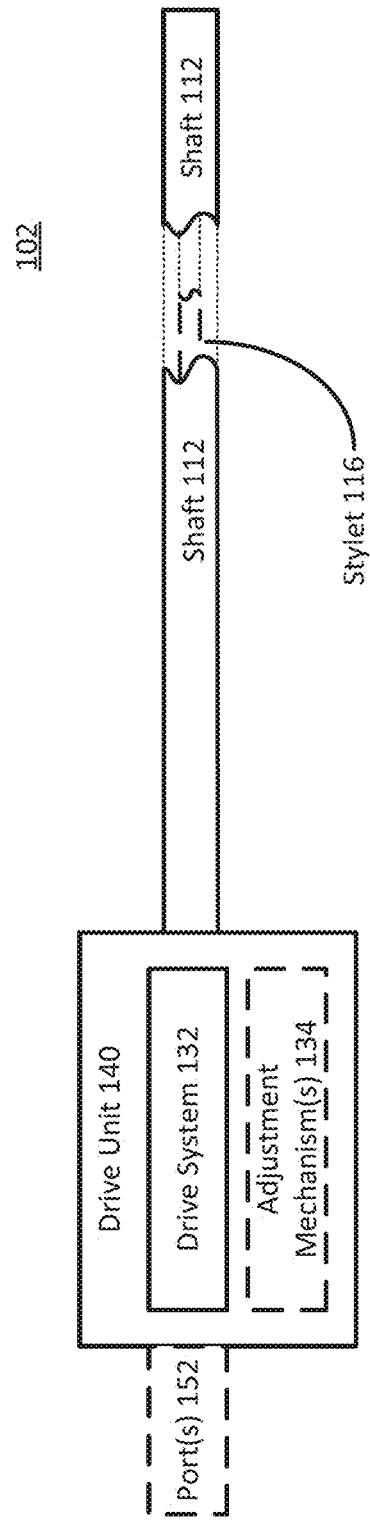
Figure 3:
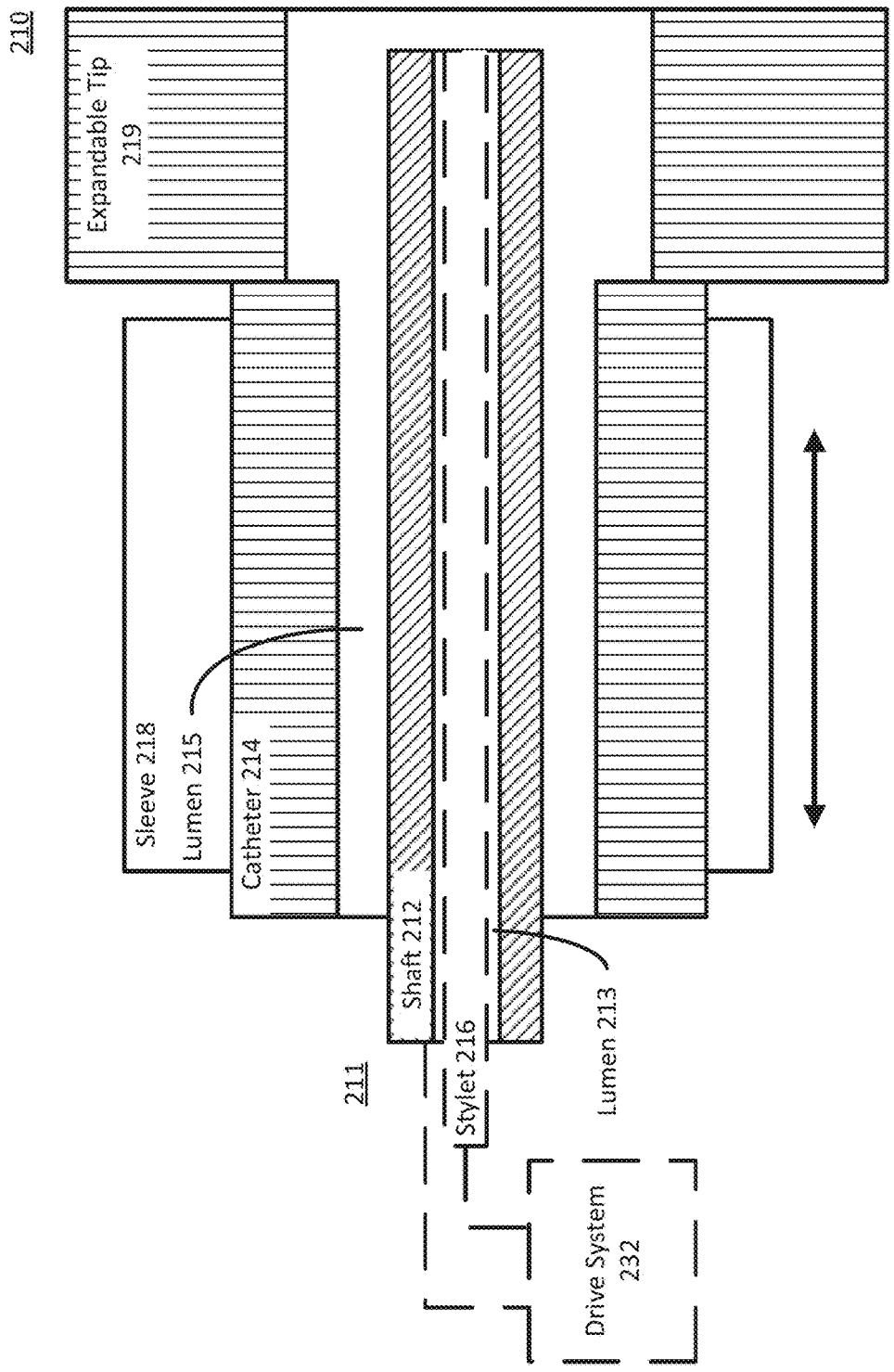
FIG. 3 is a schematic diagram of a shaft assembly of a thrombectomy system, according to embodiments.

Systems and devices described herein can be configured to remove occluding material from vasculature, including, for example, the pulmonary arteries. Systems and devices described herein can include a catheter assembly and a shaft assembly, as depicted in FIGS. 2A, 2B, and 3. FIG. 2A is a schematic block diagram of a catheter assembly 100 of a thrombectomy system or aspiration catheter system. The catheter assembly 100 can include a distal end that can be disposed in a body cavity or lumen (e.g., pulmonary artery). In some embodiments, the catheter assembly 100 can include a catheter 114 (e.g., an aspiration catheter) and a sleeve or sheath 118. The catheter 114 and sleeve 118 can be coupled at a proximal end to a handle assembly 160 including one or more catheter adjustment mechanisms 162 (also referred to as first adjustment mechanisms) configured to translate the sleeve 118 relative to the catheter 114 (or vice versa). The catheter adjustment mechanism(s) 162 can be configured to translate one or more elements of the catheter assembly 100, e.g., such as the catheter 114, sleeve 118, and/or a guidewire (not shown). In some embodiments, the catheter adjustment mechanism(s) 162 may be configured to advance and retract the catheter assembly 100 within one or more vessel lumens. In some embodiments, the catheter adjustment mechanism(s) 162 can include a component (e.g., a wheel, knob, and/or slider) that is configured to translate the sleeve 118 relative to the catheter 114, such that a distal end of the catheter 114 can be exposed distal to the sleeve 118 and be configured to expand within a body lumen. In some embodiments, the catheter adjustment mechanism(s) 162 can be configured to withdraw the sleeve 118 incrementally, e.g., to enable variable curvatures and/or expansion of the distal end of the catheter 114. In some embodiments, the catheter adjustment mechanism(s) 162 can be configured to rotate the catheter 114 and/or sleeve 118, e.g., for steering and/or seeking of a clot (e.g., sweeping of a body vessel to orient a distal opening of the catheter 114 in a direction of a clot or a portion thereof). In some embodiments, the catheter adjustment mechanism 162 can include one or more actuators (e.g., a wheel, knob, and/or slider) that may be configured to steer a distal portion of the catheter 114 (e.g., by retracting the sleeve 118 to adjust a curvature of the catheter 114 and/or rotating the catheter 114). This may be useful to direct a curved end of the catheter 114 along a length and/or circumference of a large diameter vessel as described in more detail with respect to FIGS. 14C and 15A-15E.

In some embodiments, a distal end of the catheter 114 (e.g., expandable tip 219) may have a larger diameter than other portions of the catheter 114. For example, the distal end of the catheter 114 may be expandable and may transition from a first diameter (e.g., first configuration, retracted configuration) within the sleeve 118 to a second diameter (e.g., second configuration, expanded configuration) once extended out of the sleeve 118 (e.g., translated relative to the sleeve 118). An expandable tip may facilitate ingestion of large clot burdens using a more easily navigable catheter. In some embodiments, the distal end of the catheter 114 can have a funnel-shaped structure, such as described with further detail in FIGS. 4-6. In some embodiments, a distal end of the catheter 114 may have an atraumatic tip in an expanded configuration. For example, the distal end of the catheter 114 may have a tip that is rounded or cylindrical, or have a soft structure (e.g., a pliant structure), that is designed to reduce risk of injury while the catheter 114 is being positioned within a patient's body lumen.

In some embodiments, the handle assembly 160 may be coupled to or include a connector 164 for coupling the handle assembly 160 to a shaft assembly 102 as described in more detail with respect to FIG. 2B. In some embodiments, the connector 164 may be in-line with a longitudinal axis of the catheter assembly 100, and in some embodiments, connector 164 may be angled away from the longitudinal axis of the catheter assembly 100. In some embodiments, the handle assembly 160 may be coupled to or include a vacuum port 120 configured to couple to a vacuum source VS. The vacuum source VS can be configured to generate negative pressure (e.g., suction) within a lumen of the catheter 114. For example, a thrombus from the thrombus site TS may be drawn into a distal opening of the catheter 114 by the suction generated by the vacuum source VS. The handle assembly 160 can be coupled to a proximal end of the aspiration catheter 114.

As noted above, in some embodiments, the catheter 114 can be an aspiration catheter. With larger aspiration catheters, it can be important to monitor and limit blood loss through the catheter 114, e.g., due to aspiration of blood and/or clot from within a body lumen (e.g., vessel). For example, it can be important to limit blood loss to, for example, 250 ml or less. In some embodiments, the handle assembly 160 can optionally include a vacuum interrupter or valve 163 configured to shut off or reduce vacuum or aspiration through catheter 114. For example, the vacuum interrupter 163 can be configured to close to shut off the vacuum such that further blood and/or clot is not withdrawn through the catheter 114. In some embodiments, the vacuum interrupter 163 can be manually controlled, e.g., include a switch, button, or other actuator configured for manual control by a user. The user can actuate the switch, button, etc. to turn on the vacuum and can release it to reduce or shut off vacuum within the catheter 114. The user can also use the switch, button, etc. to generate pulsed suction and/or metered flow. In some embodiments, the vacuum interrupter 163 can be electronically and/or mechanically controlled such that the vacuum interrupter 163 an automatically shut off (or reduce) the vacuum within the catheter 114, e.g., when a blood flow rate is above a predetermined threshold. In some embodiments, the vacuum interrupter 163 can be configured to turn off and/or off the vacuum, while in other embodiments, the vacuum interrupter 163 can be configured to adjust an amount of the vacuum pressure (e.g., among one or more values).

In some embodiments, the vacuum interrupter 163 can be configured to control activation of a drive system 132 of the shaft assembly 102, e.g., to control activation of the shaft 112 (e.g., to control when to activate rotation of the shaft 112). For example, the vacuum interrupter 163 can be configured to interface with a controller of the shaft assembly 102, and indicate to the controller when the vacuum or aspiration has been activated (e.g., via sending a signal to the controller). The controller, in response to receiving the indication from the vacuum interrupter 163, can be configured to cause the drive system 132 to activate rotation of the shaft 112. Alternatively, the vacuum interrupter 163 can be configured to directly control activation of the drive system 132 of the shaft assembly 102, e.g., by coupling a power source to the drive system 132 (e.g., a motor of the drive system 132). For example, the vacuum interrupter 163 can be configured to (1) activate the vacuum pressure in response to a first actuation or being actuated to a first position, and (2) activate the drive system 132 (e.g., by coupling the drive system 132 to a power source) in response to being a second actuation or being actuated to a second position. In the case of the vacuum interrupter 163 being a button, the button can be configured to (1) activate the vacuum pressure in response to being depressed a first amount, and (2) activate the drive system 132 in response to being depressed a second amount greater than the first amount. Further details of such an embodiment are described with reference to FIG. 19.

In some embodiments, the handle assembly 160 can optionally include a separate actuation element 161 configured to releasably couple to a drive unit 140 of a shaft assembly 102, as described in more detail with respect to FIG. 2B. The actuation element 161 may be configured to reversibly couple and decouple a power source to the drive unit 140, e.g., to control activation of the movement of the shaft 112 and/or stylet 116. In some embodiments, the handle assembly 160 can include a set of activation elements for independently rotating and translating the aspiration catheter 114. In some embodiments, vacuum pressure may be applied upon operator engagement with an activation element (e.g., the vacuum interrupter 163 or a separate activation element 161) and halted when the activation element has been released.

The sleeve 118 and the catheter 114 can be configured for navigation through a patient's vasculature to a target area within a lumen of the patient, e.g., a pulmonary artery of the patient. The sleeve 118 and the catheter 114 can be concentrically arranged, with an inner lumen of the catheter 114 being advanceable along a guidewire (not depicted). In use, a guidewire can be positioned within a patient's vasculature within a target vessel, and the sleeve 118 and the catheter 114 can be advanced over the guidewire and into the target vessel.

In some embodiments, the handle assembly 160 can optionally include one or more port(s) 122 including, for example, a fluid port. The fluid port can be used to flush an aspiration lumen and/or deliver one or more substances into a body lumen (e.g., one or more agents for breaking up a clot or thrombus). In some embodiments, the port(s) 122 can include a port for receiving a guidewire such that the catheter 114 and sleeve 118 can be advanced along a guidewire to a target location within a body lumen.

FIG. 2B is a schematic block diagram of a shaft assembly 102 of a thrombectomy system including a shaft 112 and an optional stylet 116 disposed within a lumen of the shaft 112. A proximal end of the shaft 112 and stylet 116 can be coupled to a drive unit 140 including a drive system 132 and one or more optional second adjustment mechanisms 134. The drive system 132 can be configured to rotate the shaft 112 and/or stylet 116 such that the distal end of the flexible shaft can rotate axially and/or about a longitudinal axis of the catheter 114 when negative pressure is being applied to the lumen of the catheter 114, e.g., to reshape or break the thrombus and cause it to be drawn proximally within the lumen of the catheter 114. The shaft assembly 102 can include a shaft adjustment mechanism 134 (also referred to as a second adjustment mechanism) that is configured to translate the shaft 112 and/or stylet 116, e.g., for fine adjustments of the position of the shaft 112 and/or stylet 116 relative to the catheter 114.

The drive system 132 can be configured to axially rotate the shaft 112 and/or stylet 116, e.g., to generate axial motion and orbital motion of the shaft 112, as described in more detail herein. In some embodiments, the drive system 132 can include a single motor that drives movement of the shaft 112 and/or stylet 116. In such embodiments, one or more gears with different gear ratios can be used to drive the shaft 112 and/or stylet 116 at different speeds. In some embodiments, the drive system 132 can include two drive motors that are configured to independently drive movement (e.g., translation and/or rotation) of the shaft 112 and/or stylet 116. In some embodiments, the shaft assembly 102 may not include a stylet 116, and in such cases, the drive system 132 can include a single motor that is configured to rotate the shaft 112.

In some embodiments, the drive unit 140 can optionally be coupled to one or more ports 152. For example, a port 152 of the shaft assembly 102 can be used to receive a guidewire, e.g., such that the catheter assembly 100 and shaft assembly 102 can be advanced along a guidewire.

In some embodiments, the catheter assembly 100 and shaft assembly 102 can be releasably coupleable to each other. For example, the drive unit 140 may be coupled to a port or connector of the handle assembly 160 (e.g., to the connector 164). In such configurations, the shaft 112 can be disposed within the lumen of the catheter 114 when the drive unit 140 is coupled to the port or connector.

In use, the catheter 114 can first be placed within a body lumen at a target location, and the shaft 112 can be inserted through an inner lumen (e.g., aspiration lumen) of the catheter 114 until a distal end of the shaft 112 is at a preset location relative to the distal end of the catheter 114. In some embodiments, one or more adjustment mechanisms (e.g., adjustment mechanism 134, 162) can be actuated to adjust a relative position of the shaft 112 and/or catheter 114 (or other components of the system, such as, for example, the stylet 116 and/or sleeve 118). Alternatively, in some embodiments, the shaft 112 can have a preset length that, after being inserted into a lumen of the catheter 114 and advanced to a point where the drive unit 140 of the shaft assembly 102 couples to the handle assembly 160 of the catheter assembly 100, is at a preset position (or within a preset range of positions) relative to a distal end of the catheter 114.

In some embodiments, one or more of the catheter 114, shaft 112, and/or stylet 116 may be structurally and/or functionally similar to those described in International Application Serial No. PCT/US2019/026737 and U.S. Application Ser. No. 63/155,191, incorporated above by reference. As described in more detail herein, the shaft 112 may be configured to rotate axially and orbitally within the lumen of the catheter 114 when the shaft assembly 102 is coupled to the catheter assembly 100.

In some embodiments, the catheter 114 can function as an aspiration catheter. A negative pressure can be applied (e.g., via vacuum source VS) to a lumen of the catheter 114, and the shaft 112 and optional stylet 116 can be rotated axially and orbitally within the catheter 114 to reshape and remove a thrombus from within a body lumen. In some embodiments, the catheter assembly 100 and shaft assembly 102 may include one more seals and/or valves (e.g., mechanical seal or valve) configured to facilitate sealing of different portions of the system for maintaining negative pressure within a lumen of the catheter 114 and/or preventing fluid leakage.

In some embodiments, one or more of the handle assembly 160 and drive unit 140 can include an onboard power source (e.g., a battery) for driving movement (e.g., translation, rotation) of the sleeve 118, catheter 114, shaft 112, and/or stylet 116. In some embodiments, handle assembly 160 and/or the drive unit 140 can be coupled to an external power source for driving movement of the sleeve 118, catheter 114, shaft 112, and/or stylet 116. In some embodiments, the handle assembly 160 may not include or be coupled to a power source, and movement of the catheter 114, sleeve 118, shaft 112, and/or stylet 116 can be actuated manually by a user, e.g., using adjustment mechanism(s) 162 and/or 134.

The optional stylet 116 can be configured to axially rotate within a shaft lumen to impart orbital motion on the shaft 112. The stylet 116 may be flexible while also having sufficient torsional stiffness to allow for axial rotation. In some embodiments, the stylet 116 may include characteristics such as a predetermined torsional stiffness (e.g., sufficiently high to withstand its rotational speeds, e.g., of about 30,000 RPM or less), a minimum bend radius (e.g., about a 4 inch or about a 10 cm bend radius or less), and sufficient flexibility (e.g., sufficiently high to enable navigation through delicate and tortuous vasculature). For example, the stylet 116 may be flexible enough to translate through a shaft lumen to a predetermined portion of the shaft or target site, as well as a tortuous path (e.g., through vasculature). In some embodiments, a stylet may be composed of, for example, Nitinol, which may be heat set to form a predetermined shape. The stylet 116 can be configured to have a non-linear shape such that, when the stylet 116 is inserted into the shaft 112, the stylet 16 can cause the shaft 112 to take on the non-linear shape. As such, the stylet 116 can have a strength that is greater than the shaft 112.

In some embodiments, the shaft 112 can be configured to have a bent, curved, or other non-linear portion. The shaft 112 can be pre-shaped to have its non-linear shape. For example, the shaft 112 can have a curved portion near its distal end such that the distal end of the shaft 112 is angled or curved away from a longitudinal axis of the linear proximal portion of the shaft 112. Further details of such a curved or non-linear shaft are described with reference to FIGS. 5-6. With a non-linear shaft, a stylet (e.g., stylet 116) may not be needed. As such, thrombectomy systems described herein may include an aspiration catheter (e.g., catheter 114) with a rotating shaft (e.g., shaft 112) without a stylet (e.g., stylet 116). In such embodiments, the non-linear shaft of the shaft can impart or induce orbital or off-axis motion of the shaft.

FIG. 3 is a schematic block diagram showing a more detailed view of a distal end of a catheter assembly 210 and shaft assembly 211 of a thrombectomy system. The catheter assembly 210 can include a catheter 214 defining a catheter lumen 215 and a sleeve 218 defining a sleeve lumen. The catheter 214 can be slidably disposed within the sleeve lumen. The shaft assembly 211 can include a shaft 212 slidably disposable within the catheter lumen 215. The catheter assembly 210 and shaft assembly 211 can include components that are structurally and/or functionally similar to the catheter assembly 100 and shaft assembly 102, respectively, as described above with reference to FIGS. 2A and 2B. In some embodiments, the catheter 214, sleeve 218, shaft 212, stylet 216, and/or drive system 232 can be structurally and/or functionally similar to the catheter 114, sleeve 118, shaft 112, stylet 116, and/or drive system 132, respectively, described with respect to FIGS. 2A and 2B. In some embodiments, the shaft 212 may define a shaft lumen 213. Optionally, a stylet 216 may be disposable within the shaft lumen 213. In some embodiments, the stylet 216 can be a second shaft (e.g., an inner shaft) and the shaft 212 can be a first shaft. In some embodiments, the stylet 216 can be movable (e.g., translatable) relative to the shaft 212. In some embodiments, the stylet 216 and the shaft 212 can be moveable (e.g., translatable) relative to the catheter 214.

In some embodiments, the distal end of the catheter 214 can include an expandable tip 219, which can be expandable once extended out of a lumen of the sleeve 218. While disposed within the sleeve 218, the expandable tip 219 can be constrained to a smaller profile configuration (e.g., a retracted configuration), but when the sleeve 218 is retracted relative to the catheter 214 (or the catheter 214 advanced relative to the sleeve 218), the expandable tip 219 can transition into its expanded configuration. The expandable tip 219 can have an atraumatic tip. In some embodiments, the expandable tip 219 include a frame or support structure, e.g., formed from a metallic material. In some embodiments, an outer and/or inner surface of the expandable tip 219 may include a membrane or flexible cover, e.g., covering one more portions of an inner frame of the expandable tip 219. For example, the membrane may have a soft structure (e.g., a pliant structure) that is designed to reduce risk of injury while the catheter 214 is being positioned within a patient's body lumen. Furthermore, the membrane or flexible cover may be configured to change shape with the expandable tip 219 of the catheter 214 (e.g., between a retracted configuration and an expanded configuration).

In some embodiments, a drive system 232 (e.g., functionally and/or structurally similar to drive system 132) may be mechanically and/or electrically coupled to the shaft 212 and, optionally, the stylet 216. The drive system 232 can be configured to drive (e.g., axially rotate) one or more of the shaft 212 and stylet 216. In some embodiments, the drive system 232 can include a first driving mechanism coupled to the shaft 212 and a second driving mechanism coupled to the stylet 216, and each driving mechanism can be configured to independently rotate the shaft 212 and the stylet 216, respectively. In some embodiments, a single drive mechanism can be used to drive both the shaft 212 and the stylet 216, but different coupling mechanisms (e.g., gears, cams, etc.) can be used to induce different speeds and/or direction of rotation in the shaft 212 and the stylet 216 and/or sleeve 218.

In some embodiments, the shaft 212 can be rotated in a first direction (e.g., clockwise, counter-clockwise) at a first speed (e.g., revolutions per minute (RPM)) while the stylet 216 can be rotated in a second direction or in the same direction and at a second speed. The shaft 212 can be shaped, as further described with reference to FIGS. 5-7B and 14C-14D. In some embodiments, the shaft 212 can have a pre-set non-linear shape, e.g., such as a bend or a curve. Rotation of the shaft 212 can cause a distal non-linear portion (e.g., bent or curved portion) of the shaft 212 to move orbitally about a longitudinal axis of a proximal linear portion of the shaft 212. Alternatively, the shaft 212 can generally be linear but can take on a non-linear shape when a shaped stylet 216 (e.g., a stylet 216 with a bend or curve) is disposed within a lumen of the shaft 212. In this latter case, the stylet 216 can be configured to impart a predefined shape on the shaft 212, depending on the relative positioning of the shaft 212 and the stylet 216. Rotation of the stylet 216 can induce orbital motion in the shaft 212, e.g., due to the shape that the stylet 216 imparts on the shaft 212. Aspiration and removal of a thrombus from a vessel lumen (e.g., patient vessel) and within the lumen 215 can depend at least on the speed and direction of both the orbital motion and rotational motion of the shaft 212. In some embodiments, the shaft 212 can be rotated at a speed below about 30,000 RPM, or below about 20,000 RPM, or below about 10,000 RPM. In some embodiments, the stylet 216 can be rotated at a speed below about 30,000 RPM, or below about 20,000 RPM, or below about 10,000 RPM. In embodiments with a stylet 216, the shaft 212 can be rotated at speeds that are greater than the stylet 216. For example, the shaft 212 can be rotated at speeds between about 10,000 RPM and about 20,000 RPM, while the stylet 216 can be rotated at speeds of about 10,000 RPM or less. In some embodiments, the shaft 212 can be rotated at a speed that is twice or greater than the speed of the stylet 216. In use, the distal end of the shaft 212 having the non-linear shape can be configured to rotate within the expandable tip 219 when the expandable tip 219 is expanded to engage and reshape portions of the thrombus captured within the expandable tip 219 (e.g., aspirated or suctioned into the expandable tip 219).

The motion of the shaft 212 is a combination of induced orbital motion and axial rotation. In some embodiments, orbital motion characteristics of a shaft 212 may depend on a shape of the stylet 216 and/or positioning of the stylet 216 relative to the shaft 212, as described in more detail in U.S. Application Ser. No. 63/155,191, incorporated above by reference.

In some embodiments, the catheter assembly 210 may be advanced into a vessel lumen towards a thrombus site (not shown). For example, a distal end of the catheter 214 may be disposed proximate to the thrombus site. Once positioned, the sleeve 218 can be withdrawn and the expandable tip 219 can expand within the vessel lumen (or the catheter 214 can be advanced out of the sleeve 218 and the expandable tip 219 can expand within the vessel lumen). The expandable tip 219 can be configured to transition from its compressed configuration within the sleeve 218 to its expanded configuration outside of the sleeve 218. When the expandable tip 219 transitions from the compressed configuration to the expanded configuration, a diameter of the lumen 215 at the expandable tip 219 can increase. This increased diameter of the lumen 215 can facilitate capture and removal of the thrombus, as further described below.

As shown in FIG. 3, a distal end of the shaft 212 and/or stylet 216 may be positioned proximal to a distal end of the catheter 214, e.g., within the expandable tip 219. As described above, the catheter 214 in its expanded state (e.g., with the expandable tip 219 in an expanded configuration) can have a larger diameter lumen at its distal end that allows a thrombus to be drawn into the catheter lumen 215 prior to mechanical interaction with one or more of the shaft 212 and stylet 216. The larger diameter lumen of the expandable tip 219 can allow the thrombus to be drawn into the lumen without or with reduced compacting or compression, which can, for example, allow the thrombus to be more easily broken or reshaped by the shaft 212 and/or stylet 216 as they rotate within the expandable tip 219. For example, a two times increase in tip diameter (e.g., from 12 F to 24 F) corresponds to about a four times increase in clot engagement force when vacuum pressure is applied. The expandable tip may further increase a depth of ingestion and facilitate acceleration of the clot towards the shaft 212 disposed within the catheter lumen such that the rotating shaft 212 need not be extended distal to the catheter and exposed within a body lumen.

Additionally or alternatively, one or more of the shaft 212 and stylet 216 may be aligned relative to a distal end of the catheter 214 or advanced distal to the distal end of the catheter 214. Additionally or alternatively, the stylet 216 may be aligned with a distal end of the catheter 214 or disposed proximal or distal to a distal end of the shaft 212. In operation, a distal end of the shaft 212 and/or stylet 216 can be disposed distal to the catheter 214 while navigating the catheter 214 and/or shaft 212 to the thrombus site. For thrombectomy, the distal end of the shaft 212 can be positioned proximal of the distal end of the catheter 214. In some embodiments, the distal end of the stylet 216 can be positioned proximal to the distal end of the shaft 212, while in other embodiments, the distal end of the stylet 216 can be positioned at the distal end of the shaft 212 and/or distal to the distal end of the shaft 212 but proximal to the distal end of the catheter 214. The shaft 212 and/or stylet 216 being positioned within the lumen 215 of the catheter 214 can then be rotated, e.g., to induce rotational and orbital motion of the shaft 212, while applying negative pressure (e.g., via a vacuum source VS), to reshape, break and/or draw the thrombus proximally within the lumen 215. For example, the distal end of the shaft 212 and/or stylet 216 can be configured to rotate within about 1 cm of a proximal end of the expandable tip 219 when the expandable tip 219 is in the expanded configuration to engage and reshape portions of a thrombus disposed within the expandable tip 219.

The shaft 212 can be structurally and/or functionally similar to shafts described in International Application Serial No. PCT/US2019/026737 and U.S. Application Ser. No. 63/155,191, incorporated above by reference. For example, the shaft 212 can be composed of multiple segments with different diameters, winding combinations, and/or braiding combinations. In some embodiments, the shaft 212 can be formed of one or multiple layers of coils, wires, or braids. For example, the shaft 212 can be a dual layer shaft with each layer constructed of coiled flat or round wires. In some embodiments, the wires of each layer can be wound in different directions. Alternatively, the shaft can be formed of a solid tube, with or without slots or cutouts. The shaft 212 can have different sections or portions with different torsional strength and/or flexibility. For example, the shaft 212 can have larger dimensions at a proximal end for greater torsional strength (e.g., an outer diameter between about 0.022 inches and about 0.065 inches, an inner diameter between about 0.012 inches and about 0.046 inches, and a bending stiffness of between about 50 N mm$^2$ and about 5000 N mm$^2$), and smaller dimensions at or near the distal end (e.g., an outer diameter between about 0.020 inches and about 0.055 inches, and an inner diameter between about 0.012 inches and about 0.046 inches, and a bending stiffness of between about 5 N mm$^2$ and about 500 N mm$^2$). In some embodiments, the shaft 212 can have at least three sections each having different diameters and/or torsional strengths, with decreasing torsional strength in more distal sections. For example, the shaft 212 can have a first section closest to the proximal end that has a first degree of stiffness, a second section closest to the distal end that has a second degree of stiffness that is less than the first degree of stiffness, and a third section between the first and second sections having a third degree of stiffness that is between the first and second degrees of stiffness. In some embodiments, the shaft 212 can have a stiffness that gradually decreases from a proximal end to a distal end, e.g., due to decreasing diameter, changing pitch and/or size of wound wires, etc. In some embodiments, the shaft 212 can have a bent, curved, or other non-linear portion, such that a distal end of the shaft 212 is angled relative to a longitudinal axis of the shaft 212 or toward a wall of the catheter 214. In such instances, rotation of the shaft 212 can cause orbital movement of the distal end of the shaft 212.

In some embodiments, the optional stylet 216 can be, for example, a second shaft that is disposed within the shaft 212. The stylet 216 can be structurally and/or functionally similar to stylets described in U.S. Application Ser. No. 63/155,191, incorporated above by reference. In some embodiments, the stylet 216 can include an inner lumen, e.g., for receiving a guidewire. In some embodiments, the stylet 216 can be a solid flexible rod. In some embodiments, the stylet 216 can be formed of one or more layers of coils, wires, or braids. For example, the stylet 212 can be a dual layer shaft with each layer constructed of flat or round wound wires. In some embodiments, the wires of each layer can be wound in different directions. In some embodiments, the stylet 216 can be a hypotube, with or without slits or cutouts. In some embodiments, the stylet 216 can include multiple sections each having different dimensions and/or stiffness. As described above, the stylet 216 can include a distal portion that has a shaped geometry. For example, the stylet 216 can include a bend near a distal end of the stylet 216, which causes a distal end of the stylet 216 to be directed toward a sidewall or inner surface of the catheter 214. In some embodiments, stylet 216 can be shaped into a plurality of curves or a continuous complex shape such as a helix.

The optional stylet 216 (or a portion of the stylet 216) can have a bending stiffness that is greater than a bending stiffness of at least a portion of the shaft 212 such that a shaped distal end of the stylet 216, when disposed within the lumen of the shaft 212, can impart a shape onto the shaft 212, the shaft 212 and the stylet 216 configured to be rotated such that the distal end of the shaft 212 can rotate axially about the longitudinal axis of the shaft 212 and orbitally about the longitudinal axis of the catheter 114.

In some embodiments, the bending stiffness may be between about 2 Nmm$^2$ and about 800 Nmm$^2$. The stylet 216, by having a greater stiffness, can impart its shape onto the shaft 212 when the stylet 216 is inserted into the shaft 212. Accordingly, when the stylet 216 is disposed within the shaft 212, the shaft 212 and the stylet 216 take on the geometry of the stylet 216. Therefore, by designing the stylet 216 to have specific geometries at various portions along the length of the stylet 216, the stylet 216 can induce the shaft 212 to have various shapes and to take on specific motion when the shaft 212 and/or stylet 216 is rotated. In some embodiments, the stylet 216 can be used to control an orbital motion of the shaft 212, e.g., by tailoring the stylet 216 to have a specific shape, by positioning the stylet 216 at different locations relative to the shaft 212, and/or by rotating the stylet 216 at different rotational speeds. For example, when the stylet 216 is disposed within the shaft 212 and rotated at a predetermined speed, the stylet 216 can cause the shaft 212 to engage in orbital motion at or based on that predetermined speed. As another example, the stylet 216, by having a specific shape at its distal end (e.g., a bend) can cause the shaft 212 to have that same or substantially similar shape when the shaft 212 moves within the catheter lumen 215.

Figure 4:
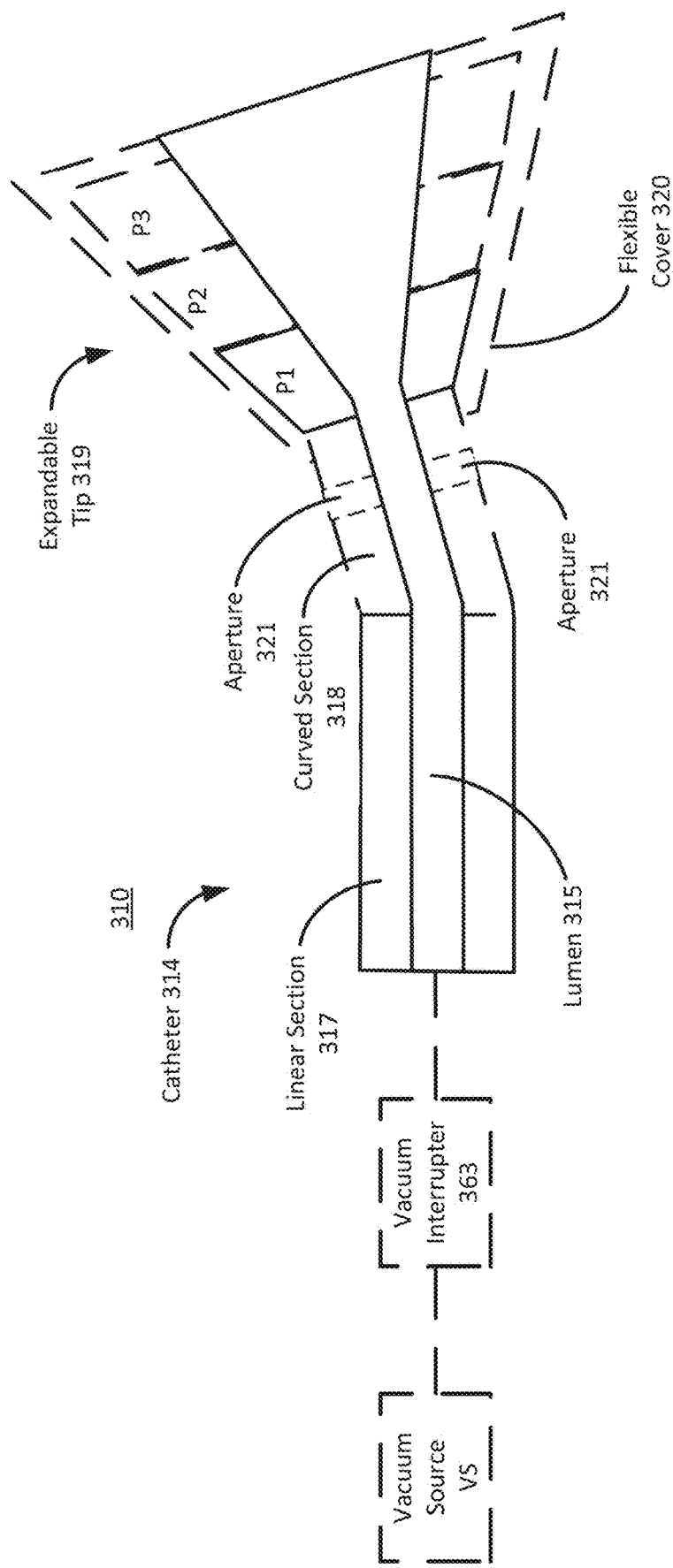
FIG. 4 is a schematic diagram of a distal end of a catheter assembly of a thrombectomy system, according to embodiments.

FIG. 4 is a schematic block diagram that provides a detailed view of a distal end of a catheter assembly 310 and of a thrombectomy system. The catheter assembly 310 can include a catheter 314 defining a catheter lumen 315. The catheter assembly 310 can include components that are structurally and/or functionally similar to the catheter assemblies 100, 210 respectively, as described above with reference to FIGS. 2A and 3. In some embodiments, the catheter 314, vacuum interrupter 363, and/or vacuum source VS can be similar to the catheter 114, 214, vacuum interrupter 163, and/or vacuum source VS of FIG. 2A, respectively, and certain details of these components are not repeated for the sake of brevity. In some embodiments, the catheter 314 may define a catheter lumen 315. A shaft and/or stylet (not shown) may be disposable within the catheter lumen 315, as described above with reference to catheter 214 and shaft 212 in FIG. 3. For example, a flexible shaft (e.g., shaft 112, 212) can have a distal end disposable within the expandable tip 319 of the aspiration catheter 314. The expandable tip 319 can include a frame (e.g., a metallic frame) and optionally, a flexible cover 320 that covers the frame.

In some embodiments, the catheter 314 may include a linear section 317, a curved section 318, and the expandable distal tip 319. The linear section 317 can include an elongate body that extends from a proximal end of the catheter 314 and may be generally linear (e.g. without any pre-formed bends, curves, or other non-linear shape). The linear section 317 may be sufficiently flexible to conform to the shape (e.g., curves, bends) of a vessel as the catheter 314 traverses through vasculature.

The curved distal portion of the catheter 314 may facilitate improved positioning of a distal end of the catheter 314 relative to a thrombus site and/or body lumen. The curved section 318 may be coupled to a distal end of the linear section 317 and a proximal end of the expandable tip 319. The lumen 315 may be defined continuously through each of the linear section 317, curved section 318, and expandable tip 319. The curved section 318 may include a pre-set curve or other non-linear shape, such that the curved section 318 offsets a distal end of the catheter 314 (e.g., the expandable tip 319) from a longitudinal axis of the linear section 317 of the catheter 314. In some embodiments, the curved section 318 can be formed of or include a memory-set metal or metal alloy. When positioned within a sleeve (e.g., sleeve 218), the curved section 318 may constrained to a straighter or more linear shape, but when extended from the sleeve (e.g., extended distally from the sleeve), the curved section 318 can be configured to transition from its constrained linear configuration to its pre-set curved configuration. The curved section 318 may be configured to set the expandable tip 319 of the catheter at a predetermined angle relative to the longitudinal axis of the linear section 317. In some embodiments, the curved section 318 may set the expandable tip 319 at an angle of between about 10 degrees and about 90 degrees relative to the linear section 317, including all sub-ranges and values in-between. In some embodiments, depending on the distance that the curved section 318 is extended out of the sleeve, the curved section 318 can be configured to set the expandable tip 319 at different angles relative to the longitudinal axis of the linear section 317. As such, the curved section 318, collectively with the sleeve, can be configured to provide variable bending or curving of the distal end of the catheter 314. Alternatively, in some embodiments, the curved section 318 can be coupled to pull wires or other elements for adjusting its degree of curvature or bending. The curved section 318 may function as a base or collar of the expandable tip 319. The curved section 318 can have a hoop strength sufficient to prevent collapse under negative pressure (e.g., generated by a vacuum source) and have strength sufficient to prevent being damaged by a shaft (e.g., shaft 212) when rotated within the catheter lumen 315.

The curved section 318 at least partially extended from the distal end of the sleeve can be configured to have a radius of curvature between about 10 mm and about 40 mm. The linear section or elongate body 317 can be coupled to an actuator configured to selectively control a degree of extension of the curved section 318 from the distal end of the sleeve, e.g., to change a degree of curvature of the memory-set curved section 318 and a position of the expandable tip 319 within a vessel (e.g., body vessel). With the curved section 318 extended, the linear section 317 can rotate within the sleeve lumen to change the position of the expandable tip 319 within a vessel. In some embodiments, the sleeve can also have a curved section that inter-operates with the curved section 318 of the catheter 314 to provide additional control to the positioning of the expandable tip 319. For example, the linear section 316 can be configured to rotate within the sleeve lumen to change a relative orientation of the curved section 318 with respect to the curved section of the sleeve (e.g., change a direction of curvature of the curved section 318 relative to the direction of curvature of the curved section of the sleeve), such that the curved sections of each can curve in the same or different directions to enhance or reduce, respectively, a total radius of curvature of the aspiration catheter 314. As such, in some embodiments, the interplay between the curved section 318 of the catheter 314 and the curved section of the sleeve can allow for a distal portion of the catheter (e.g., expandable tip 319 of the catheter) to be parallel to and/or aligned with a proximal portion of the catheter (e.g., linear section 317) or to be angled with respect to the proximal portion of the catheter. Alternatively, in some embodiments, the catheter 314 may not include a curved section but can be used with a sleeve with a curved section that controls the angling or curving of the distal end of the catheter 314.

In some embodiments, one or more apertures 321 may be disposed on the catheter 314. The aperture(s) 319 can be disposed near or on a proximal portion of the expandable tip 319, e.g., on the curved section 318 or at a proximal end of the expandable tip 319. For example, the expandable tip 319 can be formed of a metallic frame including a plurality of cells. The metallic frame can be covered by a membrane along a majority of its length, but one or more rows of the metallic frame including a set of cells may be uncovered such that those cells function as apertures 321. Alternatively or additionally, the curved section 318 proximal to the expandable tip 319 and/or a proximal portion of the expandable tip 319 may define a set of apertures 321 spaced around a circumference of the respective curved section 318 and expandable tip 319. The apertures 319 may be configured to increase fluid available to mix with the thrombus to improve flow of the thrombus proximally through the lumen 315 from the relatively larger inner diameter of the expandable tip 319 into the relatively smaller inner diameter of the lumen 315 of the linear section 317. In particular, when a large thrombus is captured within the expandable tip 319, the thrombus may become lodged and reduce or shut off blood flow through the lumen 315. Having one or more apertures 321 that are disposed within the curved section 318 and/or expandable tip 319 having the partially ingested thrombus can allow blood to still travel into the lumen 315, thereby mixing with the thrombus and encouraging proximal movement of the thrombus. In some embodiments, each aperture of the set of apertures 321 may have a diameter between about 0.3 mm and about 1 mm, including all subranges and values therebetween.

The expandable tip 319 can be configured to draw a clot or thrombus from a vessel lumen into the catheter 314 such that a shaft (e.g., shaft 212) can engage and reshape the clot to remove the clot from the vessel lumen. The expandable tip 319 can define a larger diameter portion of the lumen 315 (e.g., define a portion of the lumen 315 that has a larger diameter than a more proximal portion of the lumen 315, such as, for example, the portion of the lumen 315 defined by the linear section 317). The larger diameter portion of the lumen 315 can enable a thrombus to be drawn into the catheter 314 without significant compacting or compression, which can, for example, facilitate easier breakage or reshaping of the thrombus by a shaft assembly. In some embodiments, the expandable tip 319 coupled to the curved section 318 can transition between an unexpanded or retracted configuration (e.g., when disposed within a sleeve) and an expanded configuration (e.g., when disposed outside of the sleeve).

In some embodiments, the expandable tip 319 in the expanded configuration may have a generally funnel-shaped profile that gradually increases in diameter from a proximal end of the expandable tip 319 to a distal end of the expandable tip 319. In some embodiments, expandable tip 319 may include a first section P1, second section P2, and a third section P3, where each section P1, P2, P3 has a different structure and/or material property. For example, each section P1-P3 of the expandable tip 319 may have a different cut pattern. Each section P1-P3 can have a different strength such that a more distal section has a greater strength than a more proximal section. The cut pattern at a distal end of the expandable tip 319 (e.g., a distal end of section P3) can be selected to be of atraumatic design while withstanding shaft rotation, negative suction, and lumen collapse. While three sections P1, P2, P3 are described, it should be appreciated that the expandable tips as described in the present disclosure can include any number of sections with different structural and/or material properties.

In some embodiments, the sections P1, P2, P3 can include a metallic frame, with each section P1, P2, P3 of the metallic frame having a different mechanical structure. For example, section P1 of the metallic frame can include cells or openings that have a first set of geometric parameters (e.g., dimensions, shape, orientation, etc.), section P2 of the metallic frame can include cells or openings that have a second set of geometric parameters, and section P3 of the metallic frame can include cells or openings that have a third set of geometric parameters. Each of the first, second, and third sets of geometric parameters can be different. In an embodiment, the cells of section P1 can have a first longitudinal length, the cells of section P2 can have a second longitudinal length that is larger than the first longitudinal length, and the cells of section P3 can have a third longitudinal length that is larger than the first and second longitudinal lengths. In the same or other embodiments, the cells of sections P1, P2, and P3 can have different widths, shapes, etc.

In some embodiments, as described in more detail with respect to FIGS. 14A-14D, the expandable tip 319 may be formed of a plurality of cells having different patterns (e.g., cut patterns, laser cut patterns) along a longitudinal axis of the tip 319. For example, each section P1, P2, and P3 may have a different cell pattern configured to maintain its expanded shape under the negative suction applied through the lumen 315.

As depicted in FIG. 4, the diameter of the lumen 315 within the expandable tip 319 may increase towards the distal end of the catheter 314, such that, for example, the lumen diameter of the third section P3 is greater than the lumen diameter of the second section P2 and the lumen diameter of the second section P2 is greater than the lumen diameter of the first section P1. In some embodiments, the transition in lumen diameter from the first section P1 to the second section P2 to the third section P3 may be gradual. Additionally or alternatively, the expandable tip 319 in the expanded configuration may have a one or more stepped sections, each stepped section from the plurality having a different diameter in which a more distal stepped section has a larger diameter than a more proximal stepped section. In some embodiments, a maximum diameter of the catheter lumen 315 at the expandable tip 319 can be between about 1.5 to about 5 times a diameter of the catheter lumen 315 proximal to the expandable tip 319 (e.g., linear section 317, curved section 318), including all subranges and values in-between. The expandable tip 319 in the expanded configuration may have a maximum diameter greater than a diameter of a sleeve (e.g., sleeve 218) that is used to constrain the expandable tip 319 to a smaller diameter while the expandable tip 319 is being delivered to a target site within a vessel lumen.

In some embodiments, a vacuum source VS may be fluidically and/or mechanically coupled to the vacuum interrupter 363 and catheter lumen 315 and be configured to apply negative pressure to break and/or draw in a thrombus or clot proximally within the catheter lumen 315. For example, a proximal end of the catheter 314 may be coupleable to the vacuum source VS configured to apply a vacuum pressure (e.g., negative suction) within a lumen 315 of the catheter 314 to draw a thrombus into the lumen 315. In some embodiments, the vacuum interrupter 363 can be configured to control an amount of vacuum pressure through the catheter lumen 315 and out of the distal end of the catheter 314. In some embodiments, the vacuum interrupter 363 may be a valve and/or activation element configured for manual control of continuous and/or discrete levels of negative suction. For example, the vacuum interrupter 363 may be disposed within a handle assembly coupled to a proximal end of the catheter 314.

In operation, the expandable tip 319 can be navigated to a target location within a vessel and expanded (e.g., positioned outside of a sleeve). Vacuum pressure can be applied (e.g., via vacuum source VS) to the lumen 315 to aspirate a clot out of the vessel lumen. In some embodiments, a rotating shaft and/or stylet can be disposed within the lumen 315 with its distal end disposed within the expandable tip 319, and rotations of the shaft and/or stylet can be used to reshape and/or break the clot so that it can be drawn proximally by the vacuum pressure.

Figure 24:
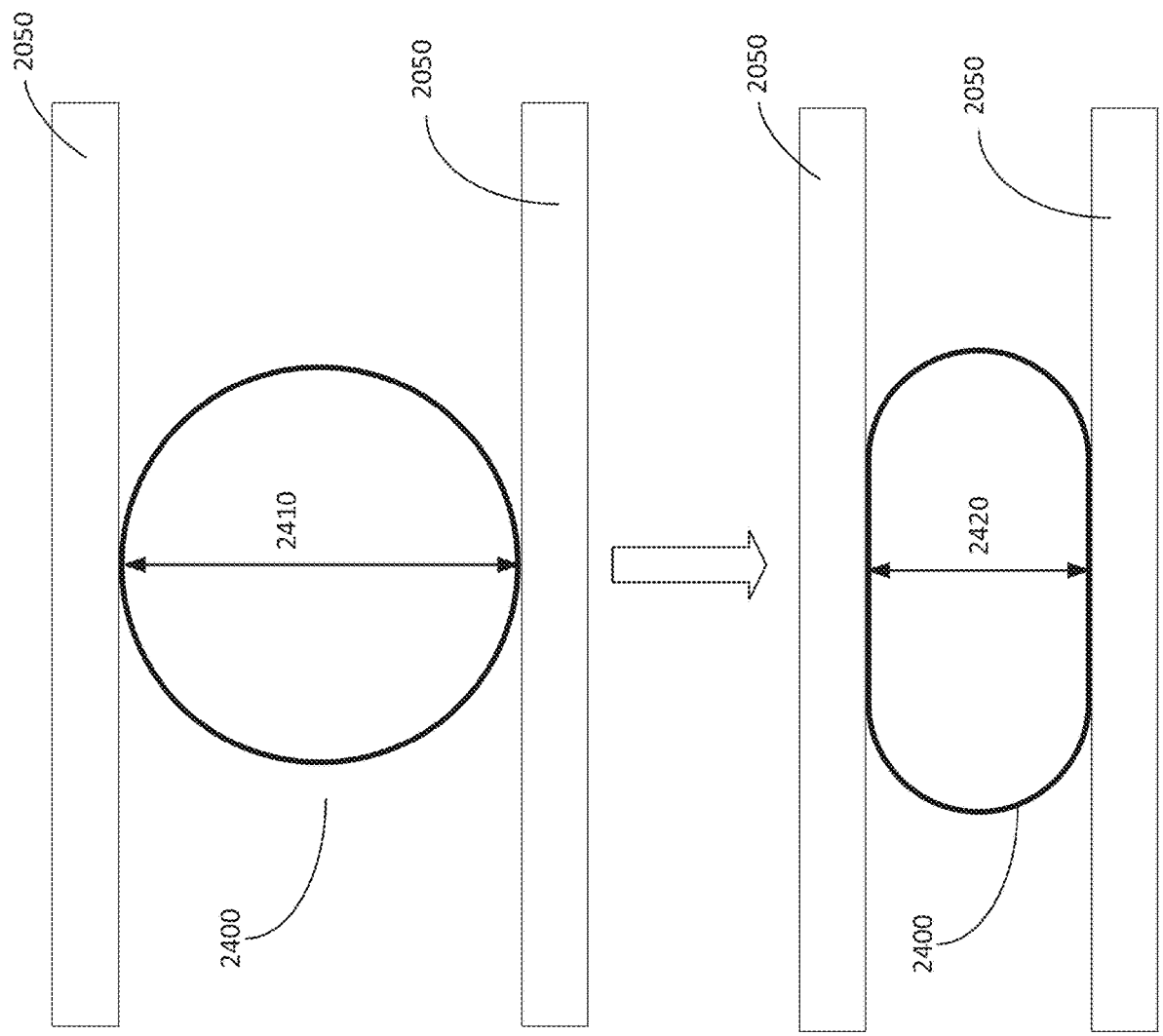
FIG. 24 schematically depicts a setup for determining a pinch strength of a distal end of a catheter assembly of a thrombectomy system, according to embodiments.

In use, when a clot is drawn into the expandable tip 319 as negative pressure is being applied, an expanded structure such as the expandable tip 319 may have a tendency to collapse shut in a pancake or flattening manner. If the expandable tip 319 were to collapse, then such would change the operation of the device. As such, in some embodiments, the expandable tip 319 may be configured to remain in the expanded configuration when negative pressure is being applied to the catheter lumen 315, e.g., to avoid flattening or collapsing. This allows the expandable tip 319 to remain open such that additional clot can be drawn into the expandable tip 319. The ability of the expandable tip 319 to resist collapse in a flattening manner can be measured or estimated by determining a pinch strength of the expandable tip 319. The pinch strength of the expandable tip 319 (or any expandable structure) can be determined by measuring a force required to compress the expandable tip 319 (or expanded structure) between two flat surfaces (e.g., plates) from its expanded diameter down to its unexpanded diameter. As schematically illustrated in FIG. 24, a pinch strength of an expandable tip 2400 may be determined by compressing the expandable tip 2400 having an expanded diameter 2410 down to an unexpanded diameter 2420 using a pair of opposing plates 2450. In some embodiments, the expandable tip 319 in the expanded configuration may have a pinch strength when disposed within a vessel (e.g., at or near a patient body temperature) of between about 0.4 lb and about 3 lb, including all ranges and sub-values in-between, e.g., such that the expandable tip 319 in the expanded configuration is configured to withstand collapse from pressure gradients being generated within the expandable tip 319 as the vacuum pressure acts on the clot within the expandable tip 319.

After the clot has been removed, the expandable tip 319 can be compressed back into its unexpanded configuration, e.g., by being retracted back into a sleeve or by the sleeve advanced over the expandable tip 319. The expandable tip 319 in the expanded configuration can be configured to be retractable into a sleeve in response to a retracting force of between about 0.5 lbs and about 4.0 lbs, including all ranges and sub-values in-between.

As described above, the expandable tip 319 can include a metallic frame and a flexible cover 320 (e.g., coating or membrane) that is disposed over the metallic frame, e.g., on an inside and/or an outside of the metallic frame. In some embodiments, a distal end of the expandable tip (e.g., third section P3) may be atraumatic to reduce damage to tissue.

As described above, the expandable tip 319 in some embodiments can have a metallic frame that defines a plurality of open cells. For example, each of the plurality of open cells has an area of at least about 0.5 mm$^2$. The plurality of open cells can increase in size from the proximal end (e.g., section P1) to the distal end (e.g., section P3) of the expandable tip 319. In some embodiments, the metallic frame further includes an atraumatic wave-shaped ring or structure at the distal end (e.g., P3) of the expandable tip 319. For example, the wave-shaped ring may have less features (e.g., connection points, crowns) than proximal cell rows. In some embodiments, the distal end of the expandable tip 319 (e.g., section P3) can have an atraumatic structure formed by one or more rows of cells with half as many or even less cells than the next most distal row of cells. As noted above, the expandable tip 319 can be configured to withstand collapse from pressure gradients being generated within the expandable tip 319 as vacuum pressure acts on a clot within the expandable tip 319. To have such strength, the expandable tip 319 can be designed with a specific cell pattern that provides greater strength at more proximal sections of the expandable tip 319 (e.g., sections of the expandable tip 319 that are proximal to where the clot is engaged with the walls of the expandable tip 319), where pressure gradients may be greater. In particular, in some embodiments, the open cells of the plurality of open cells disposed at the proximal end (e.g., section P1) of the expandable tip 319 can have a length of about 2 mm and the open cells of the plurality of open cells disposed at the distal end (e.g. section P3) of the expandable tip 319 can have a length of about 5 mm when the expandable tip is in the retracted configuration. In some embodiments, the open cells of the plurality of open cells disposed at the proximal end (e.g., P1) of the expandable tip 319 can have a proximal angle of down to about −10° and open cells of the plurality of open cells disposed at the distal end (e.g., P3) of the expandable tip 319 can have a proximal angle of up to about 40° when the expandable tip 319 is in the expanded configuration. The size and angles of the open cells are configured to resist collapse of the expandable tip 319 under vacuum while facilitating collapse of the expandable tip 319 when the aspiration catheter is drawn into a sleeve. The angles of the open cells are described in more detail with respect to FIG. 21D.

A flexible cover or coating 320 may be disposed over an outer surface and inner surface of one or more sections P1-P3 of the expandable tip 319 and/or curved section 318. For example, the coating can include an inner layer and an outer layer. In embodiments where the expandable tip 319 includes a plurality of cells, the inner and outer layers of the coating 320 can connect to one another at the plurality of open cells. That is, the area of the open cells enables inner and outer layers of the coating 320 to connect to one another at each open cell. In this manner, the expandable tip 319 may form a solid funnel to promote thrombus engagement and removal. The flexible cover 320 may have a soft structure (e.g., a pliant structure) that is designed to reduce risk of injury while the catheter 314 is being positioned within a patient's body lumen and to enable the expandable tip 319 to be captured within a sleeve.

In some embodiments, the flexible cover 320 may be constructed from an elastic or inelastic material to accommodate expansion or collapse. Substantially inelastic materials may include polytetrafluoroethylene (PTFE), expanded PTFE (ePTFE), fluorinated ethylene propylene (FEP), polyethylene terephthalate (PET), or similar materials. Elastic materials may include thermoplastics (e.g., Urethane, Pebax, Polyolefin, Nylon, etc.) and/or thermoset materials (e.g., Silicone, Santoprene, Urethane, etc.). Additionally, multiple materials may be used along the length or as layers to provide the desired mechanical properties. In an embodiment, a thin ePTFE coating can be used.

It should be appreciated that the flexible cover 320 enables collapse of the expandable tip 319 when captured (e.g., withdrawn) within a sleeve.

In some embodiments, the expandable tip 319 may have a symmetrical shape that is disposed symmetrically about a longitudinal axis of the catheter 314. Alternatively, the expandable tip 319 may have an asymmetrical shape 319 (e.g., have one side that extends more distally than another, or have one side that extends more radially than another). In some embodiments, the expandable tip 319 may have a pre-set curve, e.g., be curved relative to the curved section 318 and/or linear section 317.

Figure 5:
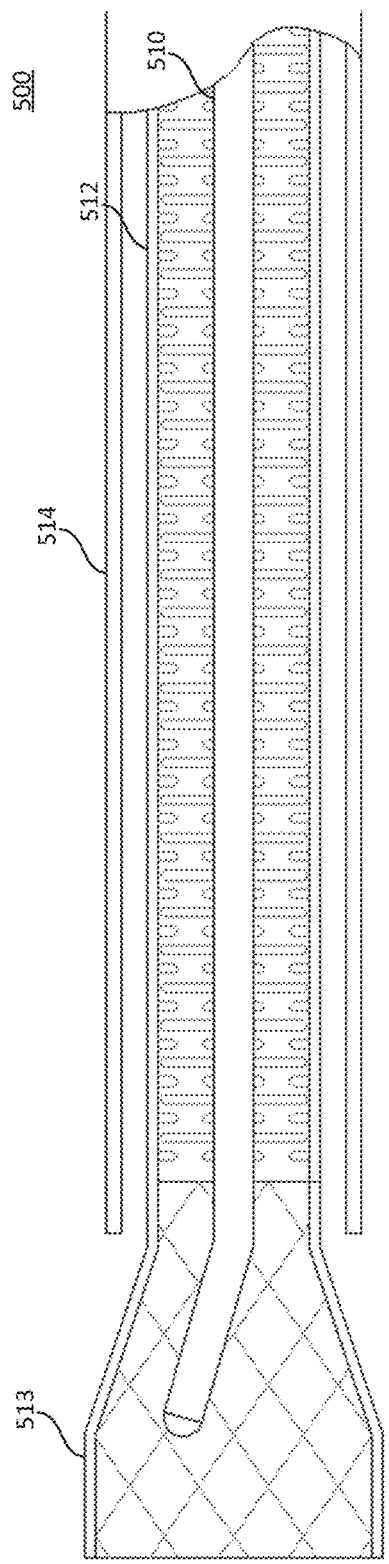
FIG. 5 is a cross-sectional side view of a thrombectomy system including a catheter and shaft assembly, according to embodiments.

FIG. 5 is a cross-sectional side view of a thrombectomy system 500 including a shaft 510, catheter 512 having an expandable tip 513, and a sleeve 514, according to embodiments. The shaft 510, catheter 512, and sleeve 514 can be structurally and/or functionally similar to other shafts, catheters, and sleeves described herein (e.g., shaft 112, 212, catheter 114, 214, 314, sleeve 218, etc.). The catheter 512 may be slidable within a lumen of the sleeve 514, and the shaft 510 may be slidable within a lumen of the catheter 512. In some embodiments, the expandable tip 513 may expand once advanced from or exposed outside of a distal end of the sleeve 514. For example, the expandable tip 513 may have a funnel shape.

In some embodiments, the catheter 512 can have a curved distal segment such that the expandable tip 513 can be angled relative to a longitudinal axis of the catheter 512, as further described with reference to FIGS. 14C-14D. The angling of the expandable tip 513 can enable the expandable tip 513 to be moved to different lateral locations within a larger body lumen, e.g., by rotating the catheter 512 about its longitudinal axis. In some embodiments, the curved distal end of the catheter 512 can direct the distal aspiration lumen of the catheter 512 to the target anatomy and clot location. In some embodiments, the curved distal segment of the catheter 512 can allow for increasing deflection (e.g., angling) with greater exposure from sleeve 514. In some embodiments, the expandable tip 513 and the shaped distal segment can be formed from one piece of Nitinol tubing with one or more different cut patterns (e.g., laser cut patterns) in different segments, thereby eliminating a joint between the two segments.

In some embodiments, a distal end of the shaft 510 may be shaped (e.g., bent, curved, or otherwise have a non-linear shape) to facilitate orbital motion of the shaft 510 within a lumen of the expandable tip 513. For example, the shaft 510 may have a bend or curve at a point near its distal end. In some embodiments, the shaft 510 may have a pre-formed shape (e.g., have a pre-formed bend or curve). Additionally or alternatively, a shape may be imparted on the shaft 510 using a stylet (e.g., stylet 216, as described above with reference to FIG. 4). Negative pressure (e.g., applied via a vacuum source) and/or axial and orbital rotation of the shaft 510 may draw a clot proximally within a lumen of the catheter 512. The orbital motion of the shaft 510 within the catheter 512 may promote hydrodynamic and direct mechanical interactions with a clot at predetermined speeds, thereby reshaping (e.g., elongating) and macerating the clot to improve aspiration and transport.

In some embodiments, the catheter 512 can have an expandable tip 513 that has a funnel shape with a larger diameter lumen. The larger diameter of the catheter lumen at the expandable tip 513 can enable thrombus to be drawn into the expandable tip 513 without significant compacting or compression, which can, for example, facilitate easier breakage or reshaping of the thrombus by the shaft 510. Additionally, the larger diameter of the catheter lumen can increase force of engagement with the thrombus and depth of ingestion of the thrombus (e.g., depth of movement of the thrombus proximally within the catheter lumen). In some embodiments, a maximum diameter of the catheter lumen at the expandable tip 513 can be at least about two times a diameter of the catheter lumen proximal to the expandable tip 513. In some embodiments, a maximum diameter of the catheter lumen at the expandable tip 513 can be between about 1.5 to about 5 times a diameter of the catheter lumen proximal to the expandable tip 513, including all subranges and values in-between. In some embodiments, an increase in the catheter diameter at the expandable tip 513 by about a factor of two (e.g., 12 French to 24 French) can increase an engagement force of the catheter 513 with the thrombus by about four times. In some embodiments, the expandable tip 513 can accelerate clot to the shaft 510 positioned safely within the catheter lumen. In particular, the shaft 510 can be positioned within the catheter lumen and rotated axially and orbitally to engage and break clot. The distal end of the shaft 510 can extend into the expandable tip 513 of the catheter 512, such that the shaft 510 can engage clot that is pulled into the expandable tip 513, e.g., via forces generated by the rotating shaft 510 and/or suction forces.

Figure 6:
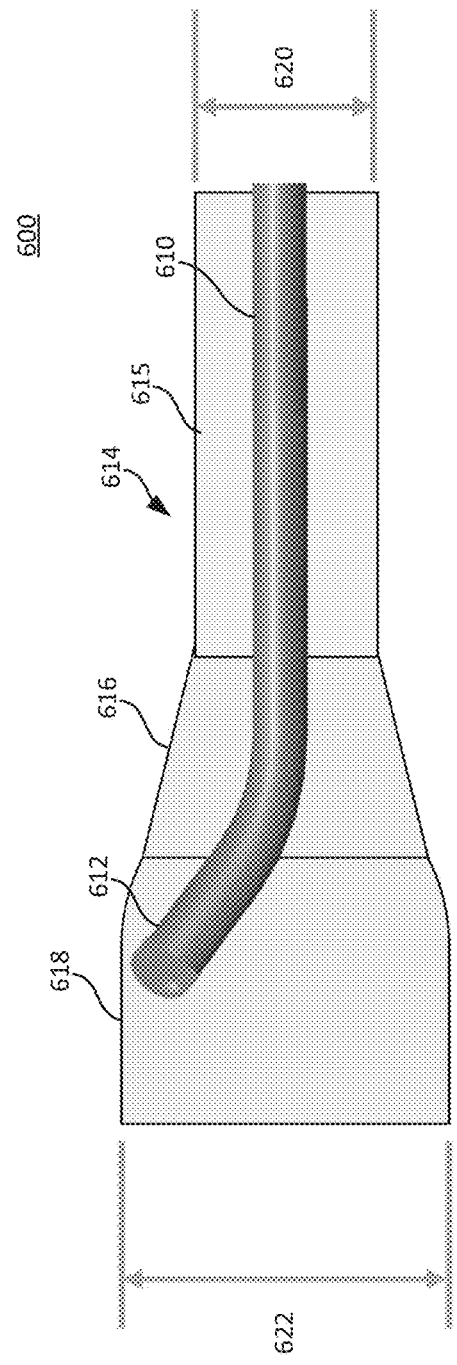
FIG. 6 is a cross-sectional side view of a thrombectomy system including a catheter and shaft assembly, according to embodiments.

FIG. 6 is a cross-sectional side view of a thrombectomy system 600 including a shaft 610 disposed within a lumen of a catheter 614. The shaft 610 and the catheter 614 can be structurally and/or functionally similar to other shafts and catheters described herein.

The catheter 614 can have an expandable tip with a first section 615 that couples to a main shaft (not depicted) of a catheter assembly and may be shaped to provide rotation directionality and/or steerability. For example, the first section 615 may have a bend or a curve that then places more distal sections of the expandable tip at an angle relative to a longitudinal axis of the catheter 614. The expandable tip can have a second section 616 that increases in diameter. The second section 616 can have a hoop strength sufficient to prevent collapse under negative pressure (e.g., generated by a vacuum source) and have strength sufficient to prevent damage from the shaft 612 when the shaft 612 is rotated within the catheter 614. The expandable tip can have a third section 618 that is an atraumatic region with flexibility sufficient to prevent vessel damage but strength sufficient to prevent collapse under negative pressure (e.g., generated by a vacuum source).

In an embodiment, the expandable tip can include an inner metallic structure (for example, similar to a stent structure) and an outer cover or membrane structure. In some embodiments, the expandable tip can be formed of a shape memory alloy or a polymer that expands upon being released or deployed from a sleeve (e.g., sleeve 218). The expandable tip can be formed using a laser cut tube, braid, coil, slit tube, or other suitable structure. In some embodiments, the expandable tip can have mechanical properties that vary along a length of the expandable tip. For example, the expandable tip can have different laser cut patterns in one or more of the sections 615, 616, 618. Such differing laser cut patterns can be selected to provide different mechanical properties that are better suited for different uses, e.g., for withstanding shaft engagement, preventing collapse, atraumatic design, etc.

In some embodiments, the expandable tip can be constructed from a braid, a coil, or multiple hoops, each capable of transitioning from a collapsed to an expanded state due to forces applied or containment forces released. A braid configuration can allow for an elongation force to be applied for the geometry to transition to a smaller diameter state along a length of the expandable tip. A coil construction may require a torsional load to be applied to allow for changes in diameter. In some embodiments, variation in density or pitch of the individual filar elements of the coil or braid may allow for various hoop/buckle strength along the length of the expandable tip.

In some embodiments, the cover or membrane around an inner metallic structure of the expandable tip can define a contiguous sealed lumen from distal opening to proximal attachment (e.g., to a proximal portion of the catheter 614. The cover or membrane may be constructed from an elastic or inelastic material to accommodate expansion or collapse. Substantially inelastic materials may include PTFE, expanded PTFE (ePTFE), FEP, PET, or similar materials. These materials can provide lower friction characteristics beneficial for allowing clot to traverse proximally and reduce wear associated with interactions with the rotating shaft 612. Elastic materials may include thermoplastics (e.g., Urethane, Pebax, Polyolefin, Nylon, etc.) and/or thermoset materials (e.g., Silicone, Santoprene, Urethane, etc.). Additionally, multiple materials may be used along the length or as layers to provide the desired mechanical properties. In an embodiment, a thin ePTFE coating can be used. The cover or membrane material may be positioned on top of the supporting metallic or stent-like structure. In this position, the material may act like a sock and not be fixedly adhered to the stent. The suction force applied to the catheter 614 and associated pressure delta from inner lumen to outside body lumen can seal the sock-like sheath and adhere the material to the inner stent-like structure. In some embodiments, the sheath can be fixed or coupled to the inner stent-like structure on the external surface, internal surface, and/or totally encase the stent-like structure. This may be accomplished with various processes.

As depicted in FIG. 6, the catheter 614 can have a first diameter 620 at a proximal end of the expandable tip and a second diameter 622 at a distal end of the expandable tip. The first diameter 620 can be less than the second diameter 622. In some embodiments, the second diameter 622 is at least two times the first diameter 620. In some embodiments, the second diameter 622 is about 1.5 to about 5 times the first diameter 620, including all subranges and values in-between. The catheter 614 can be designed to have a smaller profile during insertion and navigation to a target site (e.g., 12 French diameter when disposed within an outer sleeve such as, for example, sleeve 218) and a larger profile during thrombectomy (e.g., 24 French) such that the catheter 614 can engage and ingest clot into the distal portion as effectively as a larger catheter. The larger diameter of the expanding tip portion can allow the catheter 614 to have greater radial coverage within a body lumen. The larger diameter of the expandable tip, coupled with the diverging diameter of the second section 616 of the expandable tip, can facilitate clot engagement, acceleration, and ingestion toward the first section 615 and further toward a proximal end of the thrombectomy system 600. The larger diameter of the expandable tip can enable high clot engagement force at equivalent suction pressures (e.g., negative pressures). The high clot engagement force can cause the clot to be ingested further into a tip of the catheter 614. The high clot engagement force can also allow the clot to be captured within the second section 616 and the third section 618 more effectively than a catheter with a constant shaft diameter 620 that extends entirely to the distal end. This greater engagement force due to the expanded second diameter 622 can facilitate pulling of the entire device 614 proximally to remove a clot without disengagement from the distal end of the expandable tip.

Similar to the shaft 510, the shaft 612 can be configured to rotate axially and move orbitally within the lumen of the expandable tip of the catheter 614. The shaft 612 can be configured to engage clot that is drawn or ingested into the expandable tip portion of the catheter 614, e.g., via negative pressure, and break and/or reshape the clot for further ingestion toward a proximal end of the thrombectomy system 600. The shaft 612 can be positioned proximal of a distal end of the catheter 614 such that the shaft 612 is fully encased and prevented from engaging a wall of a body lumen, which may damage the native local anatomy, or freely spinning in the blood filled body lumen, which may cause hemolysis. Instead, the shaft 612 is configured to rotate axially and move orbitally within the third section 618 of the expandable tip to engage and draw in the clot. In some embodiments, the distal end of the shaft 612 can be positioned within the expandable tip portion at a point proximal of the distal end of the catheter 614 but at a point distal to where a clot would stop moving proximally due to suction alone.

FIGS. 7A and 7B are detailed cross-sectional side views of a thrombectomy system 700. Thrombectomy system 700 can be structurally and/or functionally similar to other thrombectomy systems described herein and can include components that are structurally and/or functionally similar to other like components described herein. For example, thrombectomy system 700 can include a catheter 710, a shaft 720, and optionally a stylet 730. Catheter 710 can be structurally and/or functionally similar to other catheters described herein, shaft 720 can be structurally and/or functionally similar to other shafts described herein, and stylet 730 can be structurally and/or functionally similar to other stylets described herein.

FIGS. 7A and 7B illustrate the different movements of the shaft 720. When used with a stylet 730, the rotational movement and orbital movement of the shaft 720 can be decoupled from one another. For example, a rotational direction of orbital motion of the shaft 720 can be controlled to be the same or different as a rotational direction of axial motion of the shaft 720. FIG. 7A depicts the system 700 where shaft 720 is rotated axially according to arrow 721 and is moved orbitally according to arrow 731, where the two arrows are in opposite directions. The rotational movement of the shaft 720 about its axis can be induced by rotating the shaft 720, and the orbital movement of the shaft 720 about a longitudinal axis of the catheter 710 can be induced by rotating the stylet 730. Accordingly, by rotating the shaft 720 and the stylet 730 in different directions, this can cause the shaft 720 to rotate axially (e.g., about its longitudinal axis) in a first direction and to move orbitally (e.g., move orbitally about a longitudinal axis of the catheter 710) in a second direction opposite the first direction. As described above, a drive system (e.g., drive system 132, 232) may be configured to independently rotate the shaft 720 and stylet 730 at predetermined rotational directions and speeds.

Alternatively, in some embodiments, the shaft 720 can rotate axially and move orbitally in the same direction, as depicted in FIG. 7B. For example, the shaft 720 can rotate axially (e.g., about its longitudinal axis) according to arrow 723 and the shaft can move orbitally (e.g., move orbitally about a longitudinal axis of the catheter 710) according to arrow 731. In such instances, the shaft 720 and the stylet 730 can be rotated in the same direction to induce axial and orbital movement in the same direction. The speed of rotation of the shaft 720 and the stylet 730 can be the same or varied to provide desirable rotational speeds of the axial and/or orbital movement.

As depicted in FIGS. 7A and 7B, the shaft 720 and/or optional stylet 730 can have a distal portion that is curved or bent. In some embodiments, the shaft 720 may be generally linear, but when a stylet 730 with a pre-set curve is inserted into the shaft 720, the shaft 720 can take on a curved shape, as defined by the stylet 730. Alternatively or additionally, the shaft 720 can be formed with a pre-set shape (e.g., a curve or a bend).

In some embodiments, the shaft 720 can be rotated without a stylet 730. When rotated at sufficient speeds, the shaft 720 can take on orbital motion. Additionally or alternately, the shaft 720 can have a pre-set shape (e.g., a curve or a bend) that can set the distal end of the shaft at an angle relative to a more proximal portion of the shaft. When the shaft 720 is rotated, the distal end of the shaft 720 then takes on orbital motion. In such cases, the orbital motion of the shaft 720 is coupled to the rotational motion of the shaft 720. In other words, the orbital and rotational motion of the shaft 720 can be in the same direction and at speeds that are directly proportional to one another.

In FIGS. 7A and 7B, the distal end of the shaft 720 can be disposed proximal of a distal end of the catheter 710 (and if an optional stylet 730 is present, the distal end of the stylet 730 can also be disposed proximal of a distal end of the catheter 710). In some embodiments, the shaft 720 and/or stylet 730 may be disposed within an expandable tip 711 of the catheter 710. In some embodiments, the distal end of the shaft 720 can rotate within the expandable tip 711 such that a diameter associated with an orbital path of the distal end of the shaft 720 can be greater than a diameter of a more proximal portion of the catheter 710. In some embodiments, the distal end of the shaft 720 can rotate within the expandable tip 711 such that the inner diameter of the expandable tip 711 can constrain the distal end of the shaft 720 such that the radius of orbital motion 731 is defined by the inner diameter of the expandable tip 711. Similar to the expandable distal portions or tips of catheters described above (e.g., catheter 512 and catheter 614), the larger diameter of the expandable tip 711 can facilitate clot engagement, acceleration, and ingestion toward a proximal end of the thrombectomy system 700.

Figure 8B:
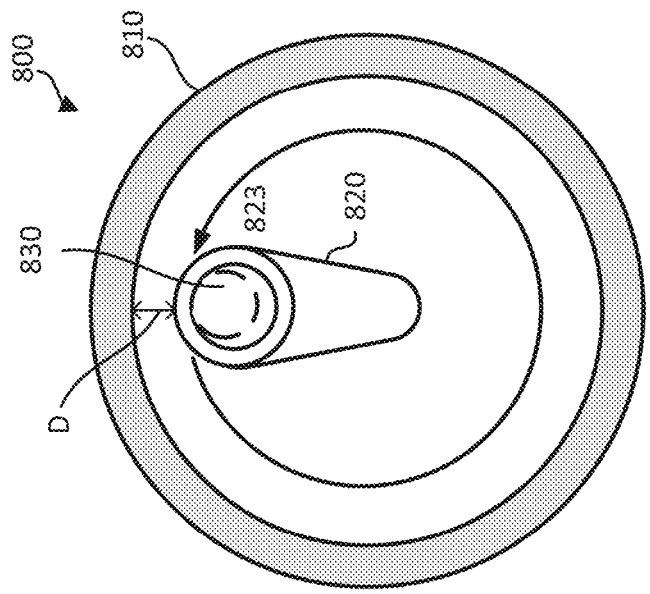
FIGS. 8A and 8B are front cross-sectional views of a catheter and shaft assembly of a thrombectomy system, according to embodiments.
Figure 8A:
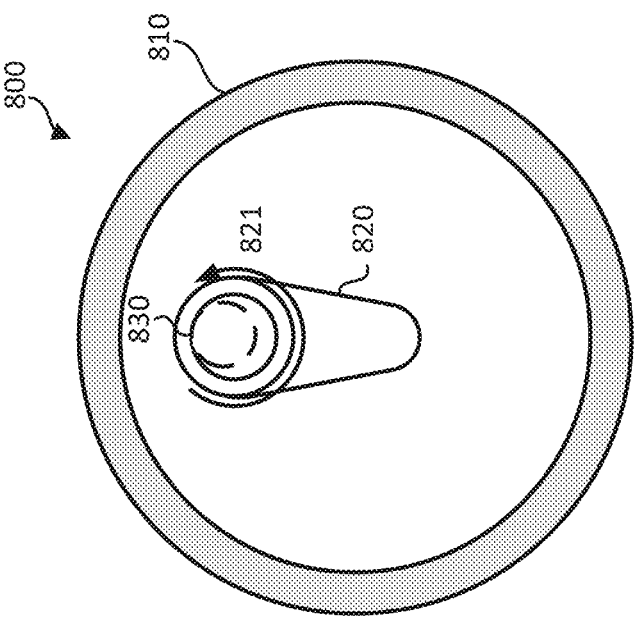

FIGS. 8A and 8B are front cross-sectional views of a thrombectomy system 800 depicting axial motion and orbital motion of a shaft. Thrombectomy system 800 can be structurally and/or functionally similar to other thrombectomy systems described herein and can include components that are structurally and/or functionally similar to other like components described herein. For example, thrombectomy system 800 can include a catheter 810, shaft 820 disposed within a lumen of the catheter 810, and optionally a stylet 830 disposed within a lumen of the shaft 820. Catheter 810 can be structurally and/or functionally similar to other catheters described herein, shaft 820 can be structurally and/or functionally similar to other shafts described herein and stylet 830 can be structurally and/or functionally similar to other stylets described herein.

FIG. 8A illustrates axial rotation 821 of the shaft 820 about a central longitudinal axis of the shaft 820. Axial rotation 821 of the shaft 820 may be generated by applying rotational force to shaft 820. FIG. 8B illustrates orbital motion 823 of the shaft 820 along an inner circumference of catheter 810. Orbital rotation 823 of the shaft 820 may be generated by applying rotational force to stylet 830. The shaft 820 can be rotating and moving orbitally within an expandable tip of the catheter 810. In some embodiments, the orbital path of the distal end of the shaft 820 can be spaced by a distance D from an inner surface of the expandable tip, while in other embodiments, the orbital path of the distal end of the shaft 820 can be adjacent to the inner surface of the expandable tip. In some embodiments, the shaft 820 may move in an orbital path that is not circular but can change or be irregular based on engagement between the shaft 820 and thrombus.

Figure 9:
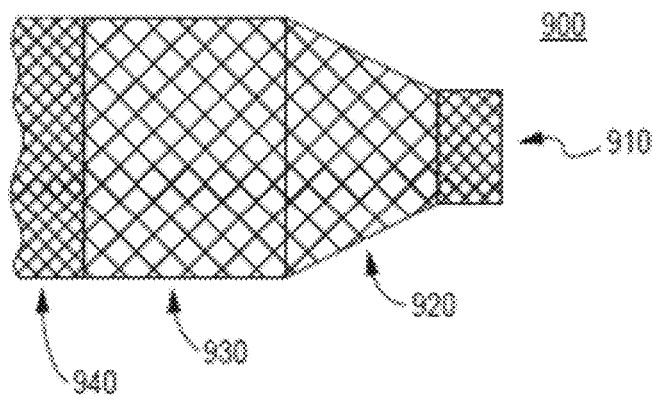
FIG. 9 is a side view of a distal end of a catheter assembly of a thrombectomy system, according to embodiments.

FIG. 9 is a side view of a distal end of a catheter 900 including a collar 910 having a high density or solid wall attachment portion, an expanding or funnel shaped portion 920, a cylindrical portion 930, and an atraumatic portion 940. The collar 910 can attach to the main body of the catheter 900. The cylindrical portion 930 can have larger struts or braids or coils to provide hoop strength, buckle strength, and basket toughness. The funnel shaped portion 920 may have similar variations in strut, braid, or coil dimensions as the cylindrical portion 930 relative to its diameter at various funnel cross-sections. The atraumatic portion 940 can be formed from a thinner wire or element and can provide a spring-like safe tip and substantially flat distal face. The strength of the expandable tip can be designed to resist collapse from a given negative pressure, and may vary in strength at different points along the length of the expandable tip to account for the different forces generated by the negative pressure at different diameters.

Figure 10:
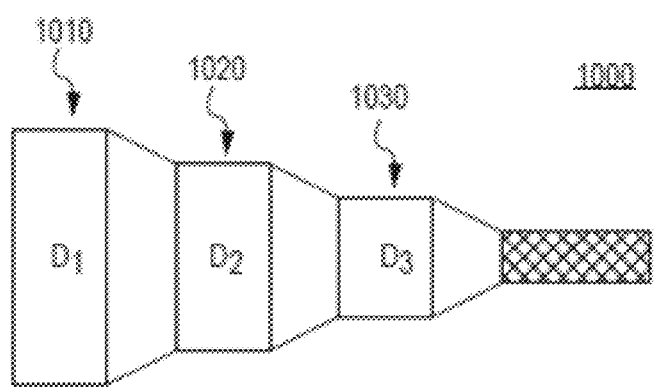
FIG. 10 is a side view of a distal end of a catheter assembly of a thrombectomy system, according to embodiments.

FIG. 10 is a side view of a distal end of a catheter 1000 including different sections 1010, 1020, 1030 with different diameters D1, D2, and D3, respectively. With increasing diameter, the collapsing forces exerted along the different sections 1010, 1020, 1030 by a vacuum pressure applied within the lumen of the expandable tip can increase proportionally. Accordingly, the expandable tip with increasing diameter can be designed to have greater strength to withstand greater forces exerted by the vacuum pressure. In some embodiments, the different sections 1010, 1020, 1030 can be designed with different structural patterns, similar to that described for expanding tip portions 920, 930, 940 that impart different strength to the different sections 1010, 1020, 1030 based on the increasing force with increasing diameter.

In some embodiments, the pattern of the expanded tip may be configured such that the pattern is substantially the same along its length when in the compressed configuration. This pattern can provide increasing resistance to collapse with greater radial expansion. In this design, the strut or wire angles can be more obtuse and circumferential in orientation in an expanded configuration (e.g., the maximally expanded state) and more acute or longitudinally oriented in a retracted configuration (e.g., the minimally expanded state). In another embodiment, the support structure pattern may be configured such that the layout and strut dimensions are different along the length of the expandable tip section in both the expanded configuration and retracted configuration.

Figure 11A:
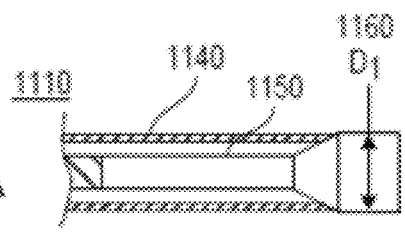
FIGS. 11A-11C are cross-sectional side views of a distal end of a catheter assembly of a thrombectomy system, according to embodiments.
Figure 11B:
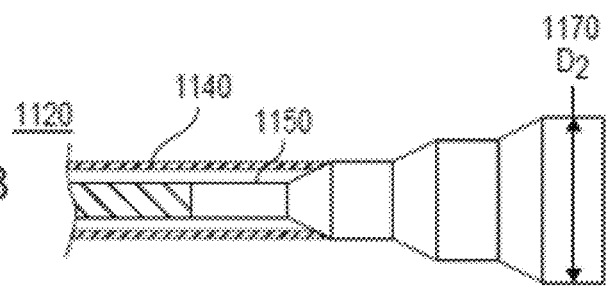
Figure 11C:
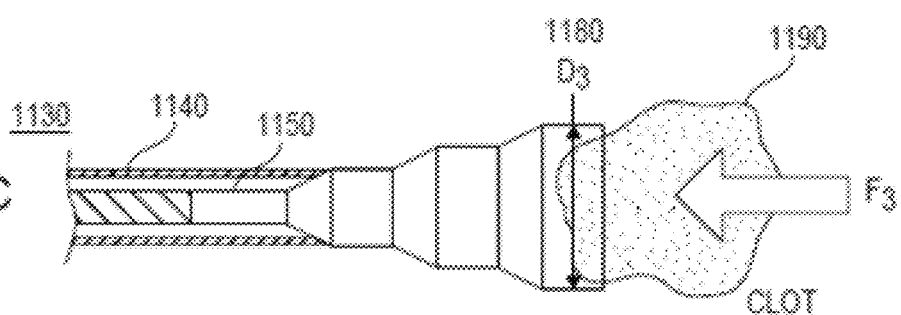

FIGS. 11A-11C are cross-sectional side views of a distal end of a thrombectomy system including a catheter 1150 disposed within a sleeve 1140. FIG. 11A depicts a distal end 1160 (e.g., expandable tip) of the catheter 1150 initially expanded to a first diameter $D_1$ when advanced out of (e.g., deployed from) the sleeve 1140, at 1110. FIG. 11B depicts the distal end 1170 of the catheter 1150 expanded to a second diameter $D_2$ when advanced out of (e.g., deployed from) the sleeve 1150, at 1120. For example, the distal end 1170 may increase in diameter in a stepped manner. FIG. 11C depicts the distal end 1180 of the catheter 1150 expanded to a third diameter $D_3$ when advanced out of (e.g., deployed from) the sleeve 1150, at 1130. A force F (e.g., suction force) may be applied to clot 1190 to draw the clot 1190 into the distal end 1180 having the expanded diameter $D_3$ to facilitate thrombus removal.

In some embodiments, an expandable tip portion of a catheter described herein may be configured in length and variable diameter to allow for varying diameter at different amounts of exposure from an inner lumen of an outer sleeve (e.g., sleeve 218). This may be accomplished by a stepped diameter configuration, or increasing exposure of the diverging angle of the funnel proximal section. This adjustment or dial in of the scale of expansion enables the catheter to be enlarged or reduced in scale to navigate larger or smaller vessel lumens, respectively. Various diameter expandable openings can also change the distal cross-sectional area and associated force of clot engagement. Such configuration can provide benefit where distal vessels have thinner walls and generally require more safety considerations. Smaller forces acting on the elements of distal anatomy can be desirable, and the smaller diameter of the expandable portion can assist in accomplishing this.

FIGS. 12A-12C are cross-sectional side views of a distal end of a catheter assembly 1200 including a set of nested catheters including first catheter 1210, second catheter 1220, and third catheter 1230. FIG. 12A depicts catheter assembly 1200 in an undeployed configuration where each of the distal ends of the catheters 1210, 1220, 1230 are substantially aligned. FIG. 12B depicts catheter assembly 1200 where second catheter 1220 is deployed into an expanded configuration where the distal end of the second catheter 1220 increases in diameter as it is advanced out of the first catheter 1210. Similarly, FIG. 12C depicts catheter assembly 1200 where third catheter 1230 is deployed into an expanded configuration where the distal end of the third catheter 1230 increases in diameter as it is advanced out of the first catheter 1210 and second catheter 1220. The nested catheter configuration can allow a user (e.g., a physician) to selectively deploy the catheter assembly 1200 at a plurality of different distal diameters. While not depicted, the catheter assembly 1200 depicted in FIGS. 12A-12C can be used with any of the shaft assemblies described herein, as well as components of such shaft assemblies. The proximal end of the catheter assembly 1200 (not depicted) can also include a handle assembly, adjustment element(s), and/or other components associated with catheter assemblies described herein (e.g., catheter assembly 100).

FIGS. 13A and 13B are cross-sectional side views of a distal end of a catheter assembly 1300 including a catheter 1330 disposed within a sleeve 1320. The catheter assembly 1300 can include components that are structurally and/or functionally similar to other catheter assemblies described herein, and can be used with any of shaft assemblies described herein. FIG. 13A depicts a distal end 1340 (e.g., expandable tip) of the catheter 1330 initially expanded to a first diameter $D_1$ when advanced out of (e.g., deployed from) or exposed outside of the sleeve 1320, at 1300. FIG. 13B depicts the distal end 1340 of the catheter 1330 expanded to a second diameter $D_2$ when advanced out of (e.g., deployed from) or exposed outside of the sleeve 1320, at 1310. The second diameter $D_2$ can be greater than the first diameter $D_1$. The distal end 1340 can have a shape that increases in diameter as a greater portion of the distal end 1340 is exposed. For example, the distal end 1340 may have a conical shape. This increasing diameter can allow a user (e.g., a physician) to selectively deploy the catheter assembly 1300 at a plurality of different distal diameters, e.g., based on a distance that the catheter 1330 is deployed outside of the sleeve 1320.

Figure 14B:
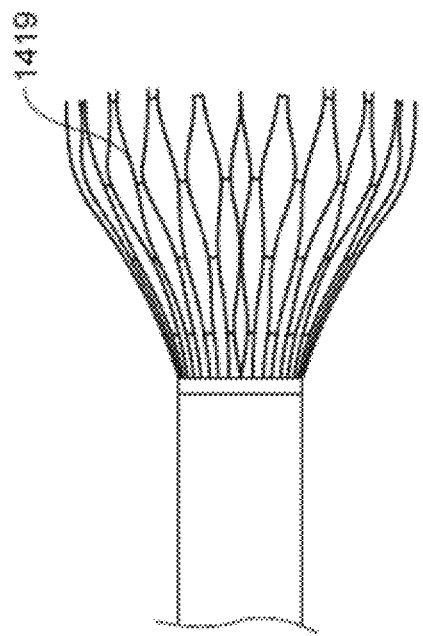
FIGS. 14A-14D are images of a distal end of a catheter assembly of a thrombectomy system, according to embodiments.
Figure 14D:
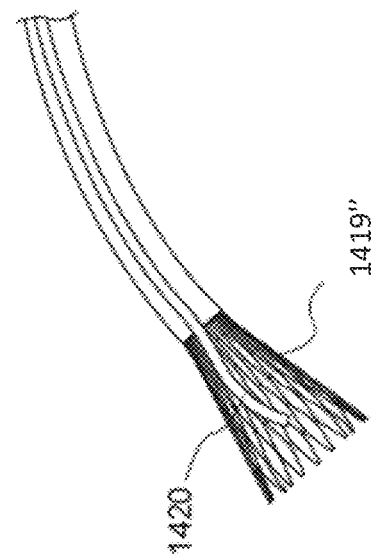
Figure 14A:
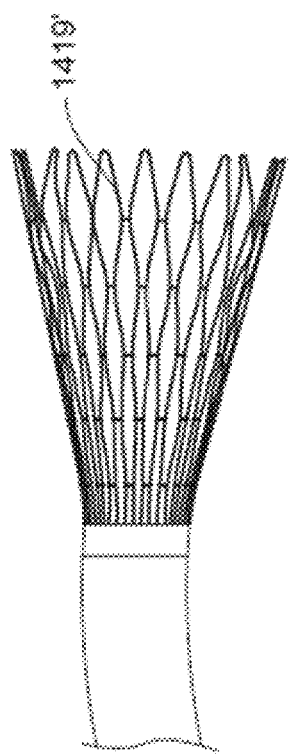

FIGS. 14A-14D are perspective views of catheter assemblies of thrombectomy systems each having a self-expanding funnel-like tip. The catheter assemblies can include components that are structurally and/or functionally similar to other catheter assemblies described herein, and can be used with any of shaft assemblies described herein. FIG. 14A depicts a catheter including an expandable distal tip 1419 that gradually increases in diameter throughout an entire length of the tip 1419. FIG. 14B depicts a catheter including an expandable distal tip 1419' having a proximal section with a first diameter, a distal section with a second diameter, and a central section that increases in diameter from the first diameter to the second diameter. Each of the tips 1419, 1419' may have a plurality of sections having a different cut pattern formed of cells. For example, proximal cells of the tip may be smaller and greater in number while the distal cells may be larger and smaller in number. In some embodiments, the most proximal cells of the tip can have a length of about 2 mm and most distal cells of the tip can have a length of about 5 mm when the expandable tip is in a compressed or non-expanded configuration. In some embodiments, the most proximal cells of the tip can have a proximal angle of about −10° and most distal cells of the tip can have a proximal angle of about 40° when the tip is in the expanded configuration. Cells between the most proximal and most distal cells can have lengths and/or angles in-between, with each row of cells gradually increasing in length and/or angle going from proximal to distal.

Figure 14C:
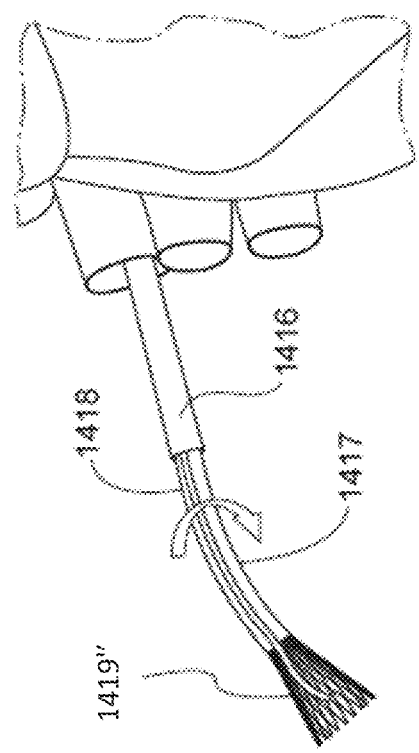

FIGS. 14C-14D depict a distal end of a catheter assembly including a catheter 1418 with an expandable distal tip 1419" having a proximal section that gradually increases in diameter to a distal section with a cylindrical (or substantially cylindrical) profile. Both expandable tips 1419' and 1419" have an atraumatic shape for facilitating movement of the catheter within a body lumen. The tip 1419" can be configured to self-expand when it is advanced outside of a sleeve or sheath 1416.

In FIGS. 14C-14D, a distal portion of the catheter 1418 may be shaped to direct the distal end or expandable tip 1419" to be at a predetermined angle relative to a more proximal section of the catheter 1418 (e.g., a section disposed within sleeve 1416). For example, the catheter 1418 can include a bend or curve 1417 that sets the expandable tip 1419" at an angle relative to a longitudinal axis of a proximal section of the catheter 1418. The angle can be between about 10 degrees and about 90 degrees, including all sub-ranges and values in-between. In some embodiments, the angle can be adjusted, e.g., by actuating a pull wire coupled to the distal end 1419 of the catheter 1418, and/or by deploying the catheter 1418 outside of the sleeve 1416 at selective distances (e.g., with further deployment creating a greater angle). In some embodiments, the angle can be fixed, e.g., by forming the catheter from a shape memory material that has a pre-set bend or curve. The stiffness of the pre-set bend or curve 1417 can be designed based on with the stiffness of the sleeve 1416 such that the sleeve 1416 is straight or in some embodiments takes on a portion of the curvature from curve 1417 when the catheter 1418 and expandable tip 1419" are fully retracted into the sleeve 1416. In some embodiments, the catheter 1418 can be rotated, e.g., via the arrow depicted in FIG. 14C, to position the distal end 1419" of the catheter 1418 at different locations within a body lumen. Stated differently, the catheter 1418 can be rotated to steer and/or sweep the distal end 1419" of the catheter 1418 within a body lumen, e.g., to target a thrombus.

Figure 21B:
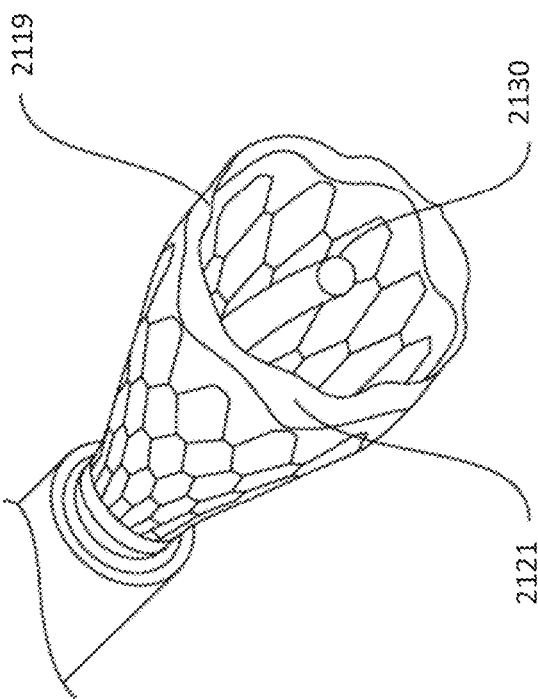
FIGS. 21A-21D are images of a distal end of a catheter assembly of a thrombectomy system in an expanded configuration, according to embodiments.
Figure 21A:
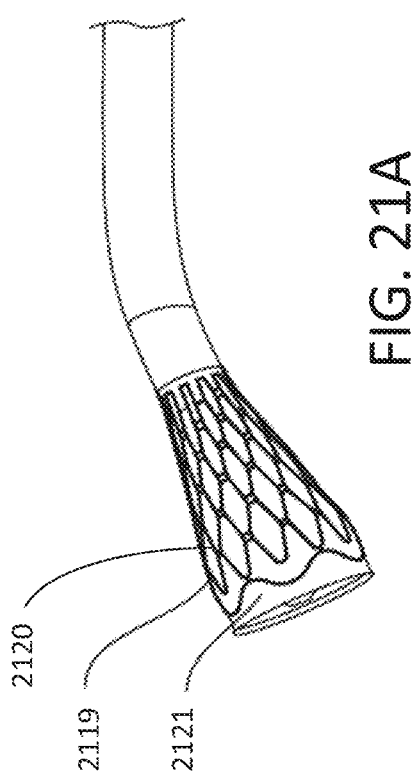
Figure 21C:
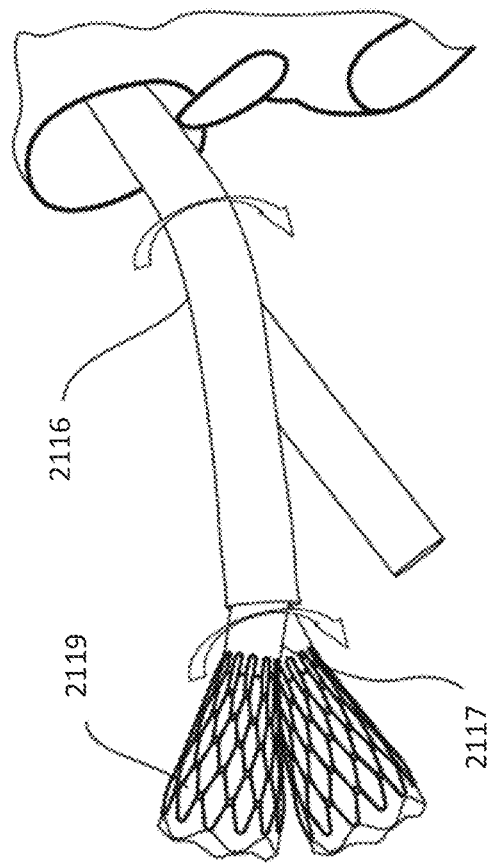

FIGS. 21A-21C are perspective views of additional embodiments of catheter assemblies of thrombectomy systems, each having a flexible cover over a self-expanding tip, according to embodiments. The catheter assemblies can include components that are structurally and/or functionally similar to other catheter assemblies described herein, and can be used with any of shaft assemblies described herein. FIG. 21A depicts a distal end of a catheter including an expandable distal section that transitions to a tip 2119 having a conical or funnel-like shape. The tip 2119 can have a metallic frame 2120 and a coating 2121 that is disposed over the metallic frame. The metallic frame 2120 defines a plurality of open cells. As depicted, the coating 2121 can have an inner layer and an outer layer that connect to one another via the open spaces (e.g., holes, apertures) of the open cells. The plurality of open cells in FIGS. 21A-21C increase in size from the proximal end to the distal end of the expandable tip 2119, similar to other expandable tips described herein. The metallic frame further includes an atraumatic wave-shaped structure at the distal end of the expandable tip 2119. As shown in FIG. 21A, the wave-shaped (e.g., undulating, U-shaped) structure can be formed from open cells that have half as many features (e.g., crowns) as an adjacent proximal row of open cells, such that the structure couples to the adjacent row of open cells at every other crown. The reduced number of features at the distal end provide the atraumatic shape.

The expandable tip 2119 can be configured to transition between a compressed or constrained configuration (e.g., when disposed within a sleeve 2116) and an expanded configuration (e.g., when extended outside of the sleeve 2116). The flexible cover 2121 may be disposed over an outer surface and inner surface of the tip 2119. The flexible cover 2121, by covering the open cells of the expandable tip 2119, can facilitate generation of negative suction within the expandable tip 2119 to draw a thrombus proximally within a lumen of the catheter. In some embodiments, the flexible over 2121 can be configured to extend distally from the distal end of the metallic frame, e.g., to further aid in providing an atraumatic structure at the distal end of the catheter.

FIG. 21B depicts a shaft 2130 within a lumen of the expandable tip 2119. The shaft 2130 can be structurally and/or functionally similar to other shafts described herein. The shaft 2130, for example, can be configured to rotate within the catheter, with its end being disposed within the expandable tip 2119 of the catheter. The shaft 2130, via its placement and rotation, can be configured to reshape a thrombus drawn into the expandable tip, e.g., to further facilitate its proximal movement and removal from a vessel lumen.

FIG. 21C depicts a distal end of a catheter assembly, according to embodiments. The distal end can be configured to be directed (e.g., steered) toward a predetermined target (e.g., a thrombus) in a body lumen by rotating a catheter and/or sleeve. Similar to FIG. 14C, FIG. 21C depicts a catheter having a bend or curve 2117 being rotated to steer the expandable tip 2119 of the catheter. Furthermore, a sleeve 2116 disposed over the catheter assembly may include a bend or curve. The curve of the sleeve 2116 can interoperate with the curved portion 2117 of the catheter, e.g., to provide additional control to the positioning of the expandable tip 2119. For example, the curve of the sleeve 2116 and the curved portion 2117 of the catheter can operate together to set the distal end of the catheter at an angle relative to a longitudinal axis of a more proximal linear section of the sleeve and catheter. The angle can be between about 10 degrees and about 90 degrees, including all subranges and values in-between. In some embodiments, the angle can be adjusted or varied, e.g., by actuating a pull wire coupled to the sleeve 2116, by varying the amount or distance that the curved portion of the catheter is extended out of the sleeve 2116, by changing a direction of curvature of the curved portion of the catheter relative to the curved portion of the sleeve, etc. In some embodiments, the angle can be fixed, e.g., by forming the sleeve 2116 with a pre-set bend or curve. In some embodiments, the curve of the sleeve 2116 may oppose a curve of the curved portion 2117 of the catheter such that, for example, a distal end of the catheter can generally follow the longitudinal axis of the catheter. The stiffness of the pre-set bend or curve can be designed based on the stiffness of the sleeve 2116. As shown in FIG. 21C, the sleeve 2116 can be rotated to position the distal end of the catheter at different locations within a body lumen. Accordingly, fine adjustment of the position and angle of the catheter may be provided by rotation of the catheter and/or sleeve. Such adjustments can facilitate navigation of the catheter assembly through a patient's vasculature and/or positioning of the distal end of the catheter assembly for optimal engagement and capture of a clot.

Figure 21D:
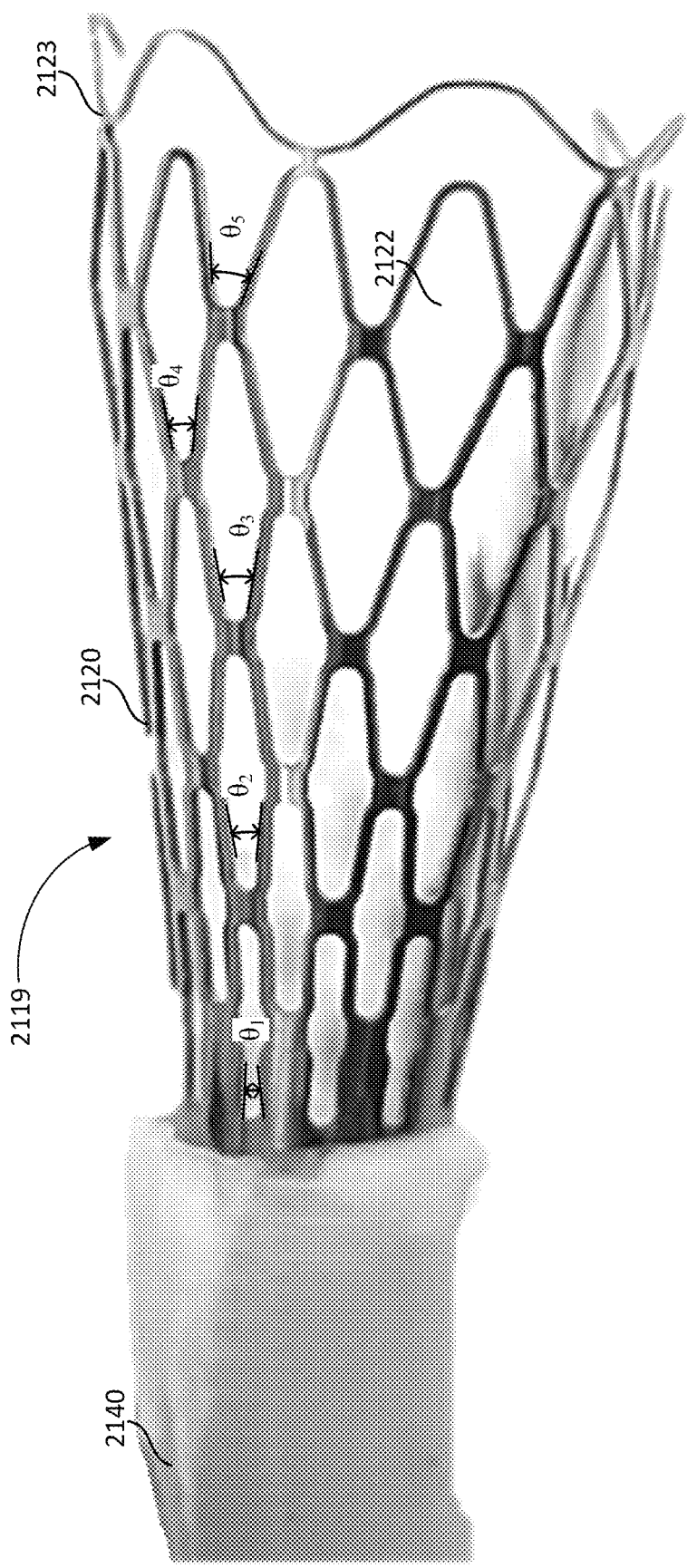

FIG. 21D depicts a distal end of a catheter assembly, according to embodiments. The expandable tip 2119 in the expanded configuration includes a metallic frame 2020 defining a plurality of open cells 2122. A coating over the metallic frame 2020 is not shown in FIG. 21D for the sake of clarity. In some embodiments, each of the plurality of open cells 2122 has an area of at least about 0.5 mm$^2$ to enable the inner and outer layers of the coating to connect to one another at each open cell. As shown in FIG. 21D, the plurality of open cells 2122 increase in size from the proximal end to the distal end of the expandable tip 2119. The metallic frame can further include an atraumatic wave-shaped ring 2123 at the distal end of the expandable tip 2119. In the compressed configuration of the expandable tip 2119 shown in FIG. 21E, the ring 2123 may have a generally repeating U-shape. The ring 2123 may generally be flexible and atraumatic to reduce and/or prevent damage to tissue.

In some embodiments, the open cells can be configured to have sizes (e.g., length, area) and angles that are configured to resist collapse of the expandable tip 2119 under vacuum while allowing for collapse of the expandable tip 2119 when the aspiration catheter is withdrawn into a sleeve. In some embodiments, open cells of the plurality of open cells disposed at the proximal end of the expandable tip 2119 may have a proximal angle of between about −10° and about 0°, including all subranges and values therebetween, and open cells of the plurality of open cells disposed at the distal end of the expandable tip may have a proximal angle of about 20° to about 40°, including all subranges and values therebetween, when the expandable tip is in the expanded configuration. In the context of this example, a negative angle represents an angle that decreasing from a proximal to a distal end of the expandable tip 2119. In some embodiments, each row of open cells have a different angle. For example, as depicted in FIG. 21D, a proximal most open cell may have a negative proximal angle $\theta_1$, such as, for example, between about −10° to about −0°, including about −5°. A more distal open cell may have a proximal angle $\theta_2$ that is larger than the proximal angle $\theta_1$, such as for example, between about 0° and about 20°, including about 15°. A still more distal open cell may have a proximal angle $\theta_3$ larger than the proximal angle $\theta_2$, such as, for example, between about 20° to about 40°, including about 30°. Similarly, additional distal open cells may have proximal angles $\theta_4$ and proximal angle $\theta_5$ that are different than proximal angles $\theta_1$, $\theta_2$, $\theta_3$. In some embodiments, rows of open cells that are more distal can have greater proximal angles than rows of open cells that are more proximal. In some embodiments, rows of open cells going from proximal to distal can increase in proximal angle for a predetermined number of rows (e.g., between about 2 and about 20, including all values and subranges therebetween) and then stay substantially the same in a distal section of the expandable tip 2119. For example, as depicted in FIG. 21D, proximal angles $\theta_1$, $\theta_2$, $\theta_3$ can increase in value, while proximal angles $\theta_3$, $\theta_4$, $\theta_5$ may stay substantially the same.

Figure 21E:
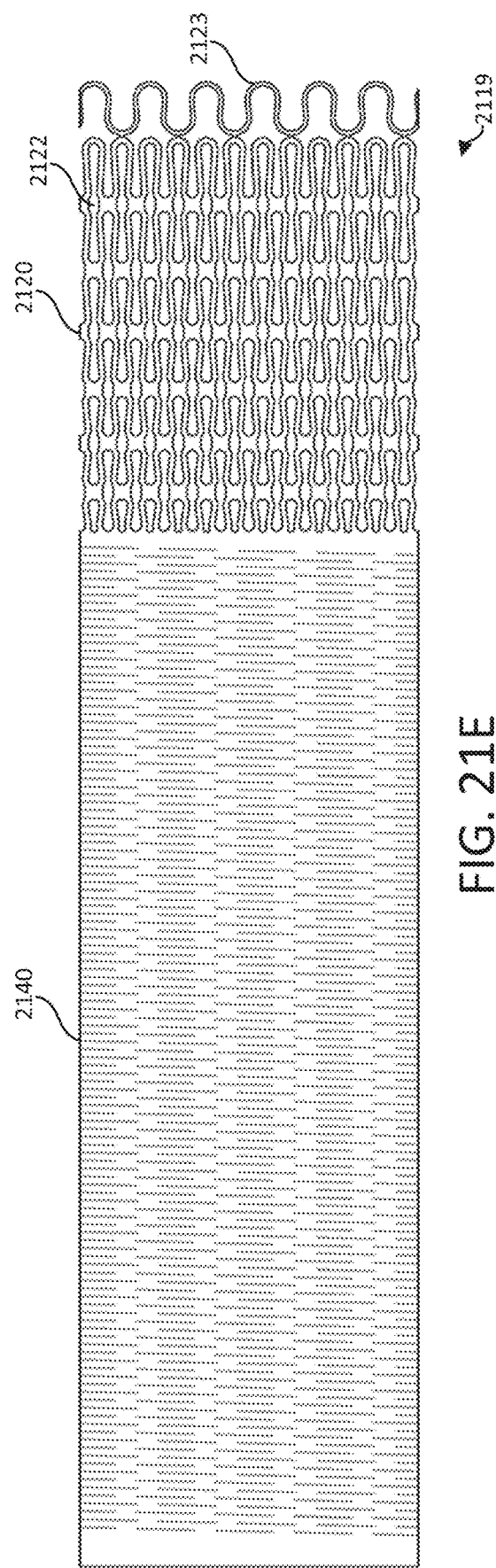
FIG. 21E shows a view of the distal end of the catheter assembly cut open and laid flat.

The expanded open cell structure with proximal angles as depicted in FIG. 21D can result from the rows of open cells having different longitudinal lengths when they are not expanded, i.e., in a undeployed or retracted configuration. FIG. 21E depicts a flat, cut open view of a distal end of the catheter assembly, according to embodiments. The flat, cut open view shows the geometry of the open cells of the expandable tip 2119 in their unexpanded state. In the unexpanded state, the open cells of the plurality of open cells 2122 disposed at the proximal end of the expandable tip 2119 may have a length of between about 0.5 mm and about 3 mm, including about 2 mm and other values or sub-ranges therebetween, and open cells of the plurality of open cells 2112 disposed at the distal end of the expandable tip 2119 may have a length of between about 3 mm and about 10 mm, including about 5 mm and other values or sub-ranges therebetween. For example, the open cells of the plurality of open cells disposed at the proximal end of the expandable tip 2119 can have a length of at least about 2 mm and the open cells of the plurality of open cells disposed at the distal end of the expandable tip 2119 can have a length of less than about 5 mm, when the expandable tip is in the retracted configuration. In some embodiments, the distal most row of open cells can have a longitudinal length that is between about 2 and about 10 times (including about 5 times) the longitudinal length of the proximal most row of open cells, including all values and sub-ranges therebetween. The plurality of open cells 2122 may be arranged in offset rows where each row may be offset by about 50% from its adjacent rows. The expandable tip 2119, by having its open cells 2122 arranged in offset rows, can expand such that the open cells 2122 are diamond-shaped (or substantially diamond-shaped) when expanded.

In some embodiments, the catheter shaft may include a first coating (e.g., Pebax) while the metallic frame of the expandable tip 2119 may include a second coating (e.g., PTFE or ePTFE) where the second coating is more flexible than the first coating. The first coating may be low friction to facilitate proximal thrombus movement through the catheter assembly while the second coating is relatively more flexible to facilitate reduced bending stiffness of the distal end. In some embodiments, the expandable tip 2119 may be joined to a first portion 2140 of the catheter shaft. The first portion 2140 of the catheter shaft may be or include a curved or bent section (e.g., curved section 318). In some embodiments, the first portion 2140 and the expandable tip 2119 can be formed from a single metallic tube, e.g., a nitinol tube. In some embodiments, the first portion 2140 of the catheter shaft can be coupled to a more proximal portion of the catheter shaft (e.g., a linear section 314) that is formed of a different material (e.g., stainless steel). As such, in some embodiments, the first portion 2140 of the catheter shaft can have different material properties than more proximal portions of the catheter shaft.

Figure 15C:
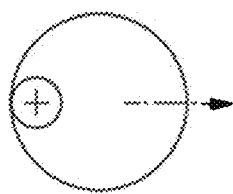
FIGS. 15A-15E are schematic views of a distal end of a catheter assembly of a thrombectomy system, according to embodiments.
Figure 15E:
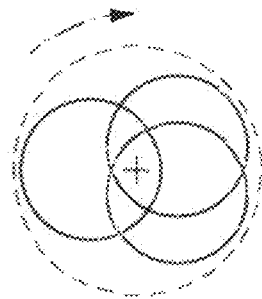
Figure 15B:
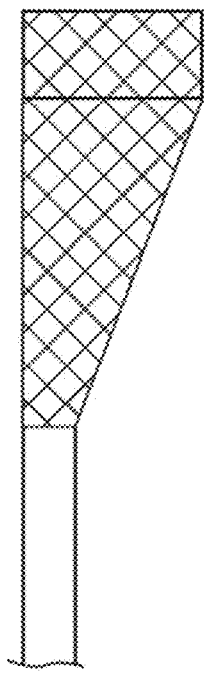
Figure 15D:
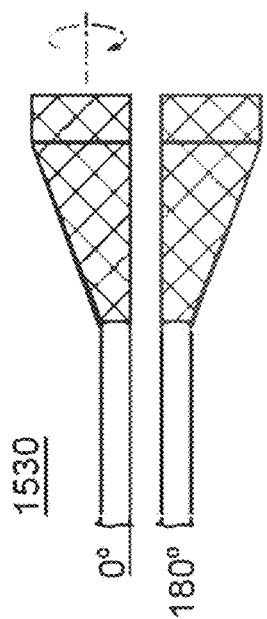
Figure 15A:
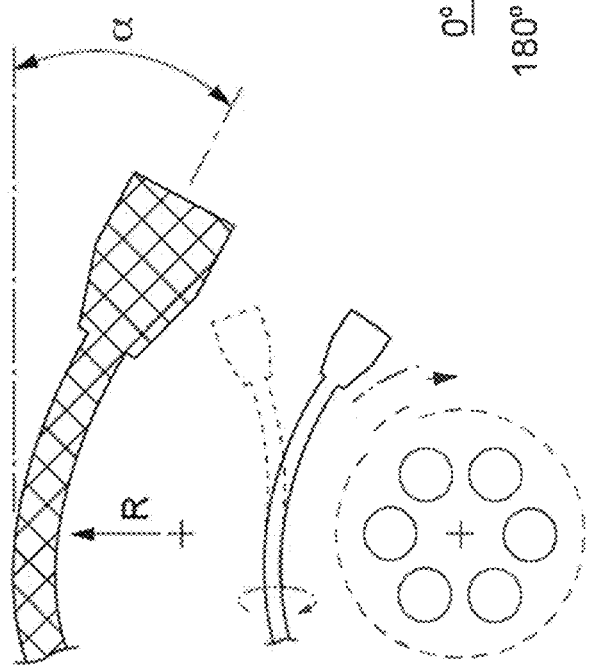

FIGS. 15A-15E are schematic views of a distal end of catheter assemblies of a thrombectomy system, according to embodiments. The catheter assemblies can include components that are structurally and/or functionally similar to other catheter assemblies described herein, and can be used with any of shaft assemblies described herein. FIG. 15A depicts a radius of curvature R of a distal portion of an aspiration catheter 1510 that enables a distal opening of the catheter to be directed (e.g., at an angle α) at target anatomy such as a clot. By rotating the aspiration catheter having a curved distal portion, the aspiration catheter 1510 may effectively sweep an inner circumference of a blood vessel, thereby facilitating complete or a greater range of clot engagement and removal. By rotating the curved aspiration catheter, the distal tip may be selectively directed or steered toward, for example, an ostia of a target vessel for advancement into that vessel.

FIG. 15B depicts a side view of aspiration catheter 1520 having an asymmetric distal end that provides a relatively large sweeping diameter when rotated about a longitudinal axis of the catheter 1520. FIG. 15C illustrates a front view of the aspiration catheter 1520 where the opening of the distal end (e.g., expandable tip) is offset with respect to the longitudinal axis of a proximal linear portion of the catheter 1520 (represented by the "+" symbol). FIG. 15D illustrates the orientation of an aspiration catheter 1530 (e.g., similar to catheter 1520) in two positions (i.e., 0°, 180°) while being rotated about its longitudinal axis, and FIG. 15E is a front view of a coverage area of the aspiration catheter with a body lumen of the rotated aspiration catheter 1530. As depicted, the rotation of the catheters 1510, 1520, 1530 can facilitate greater coverage within a larger body lumen, thereby allowing a user to sweep within the body lumen to target more areas for removal of thrombus and/or selectively direct the distal end at target thrombus or target vessels.

In some embodiments, the aspiration catheters 1510, 1520, 1530 may comprise one or more of a slit, stent pattern, shaped polymer, shape memory alloy, and the like. In some embodiments, one or more pull wires may be configured to deflect the distal end. For example, a longitudinal backbone without the ability to compress and a slotted flexible section positioned 180 degrees from the backbone on the cylindrical portion of distal pattern would allow a pull wire, attached to the distal tip of the catheter on the flexible side, to be forced backward, compress the flexible portion and impart a bend to the tip of the catheters 1510, 1520, 1530.

Figure 16A:
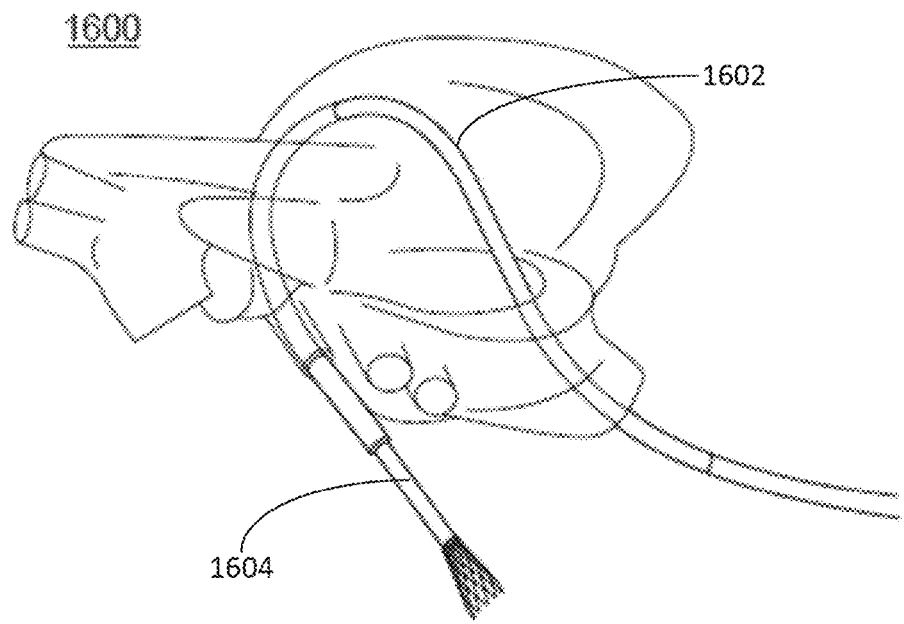
FIGS. 16A and 16B are images of a thrombectomy system navigated through simulated vasculature, according to embodiments.
Figure 16B:
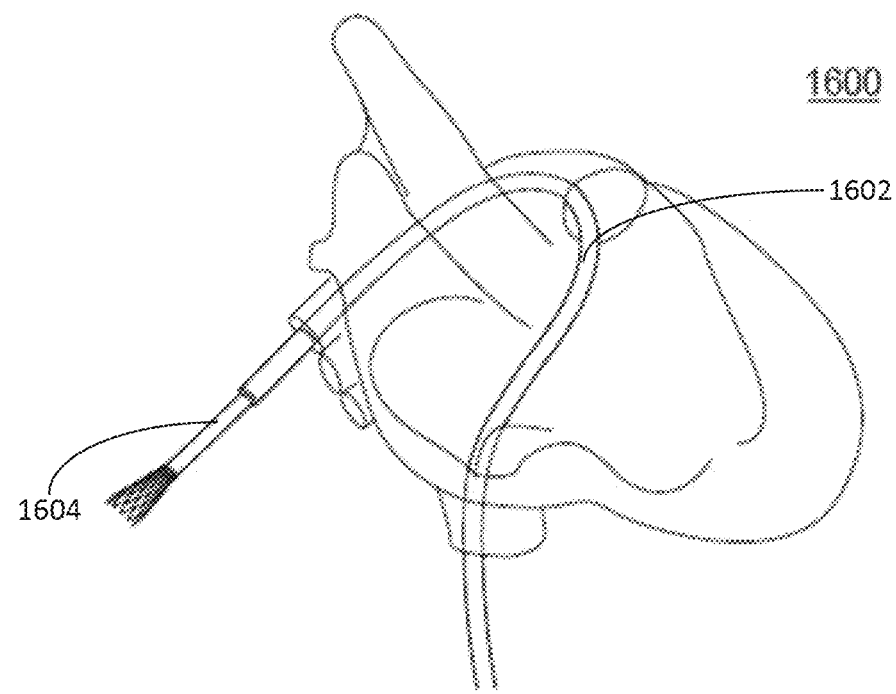
Figure 17C:
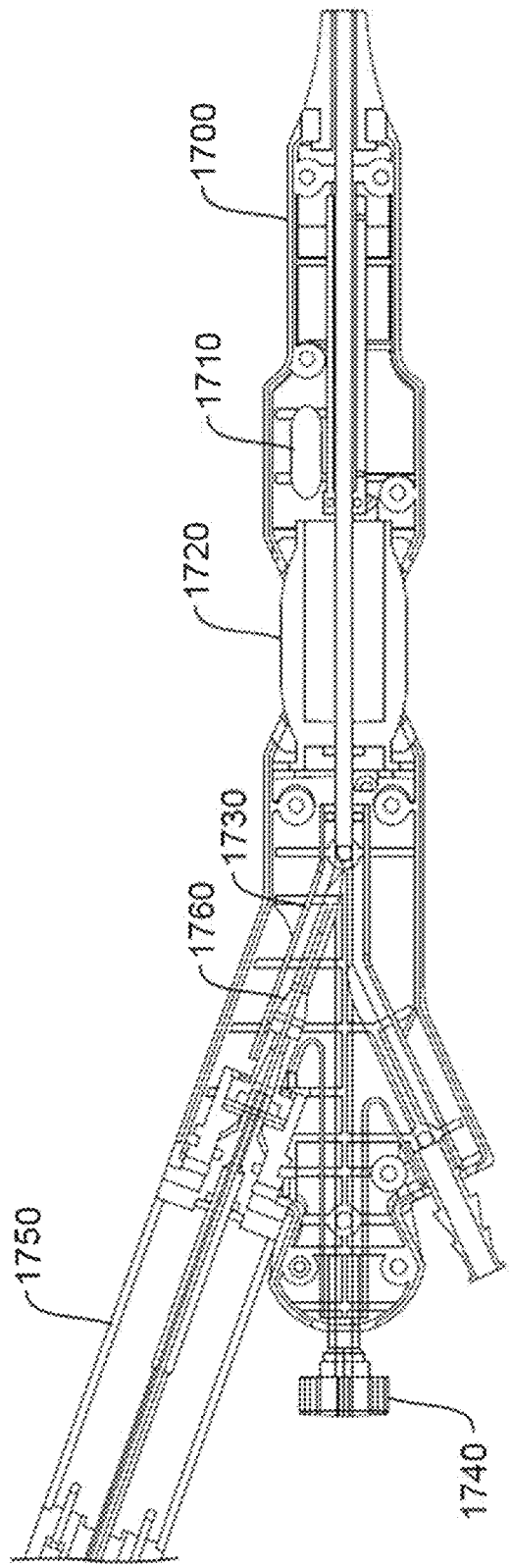
FIGS. 17C and 17D are additional cross-sectional side views of the handle of the thrombectomy system depicted in FIG. 17A.
Figure 17D:
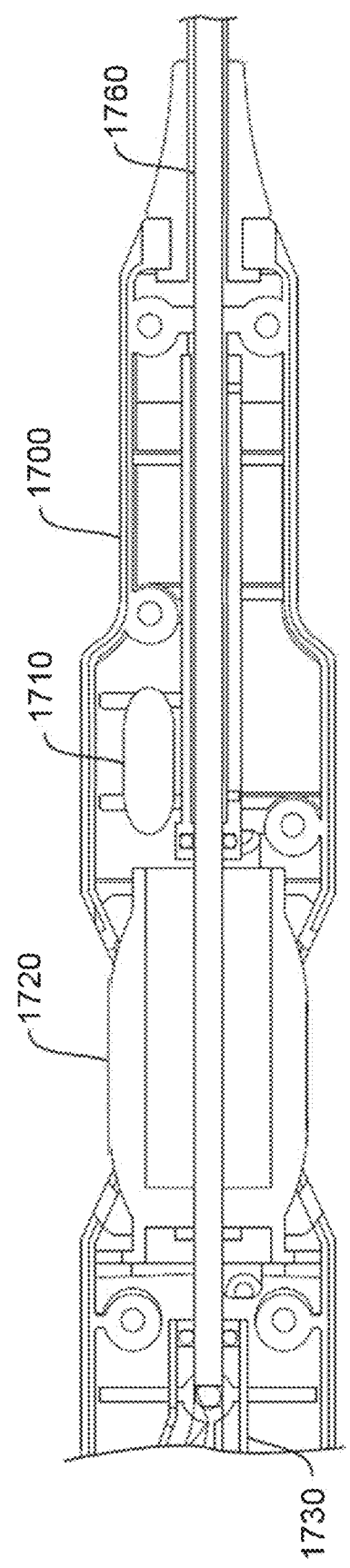

FIGS. 16A and 16B are images of a thrombectomy system 1600 navigated through a model vasculature, including through the inferior vena cava, right atrium, and right ventricle of a heart of a patient. The thrombectomy system depicted in FIGS. 16A and 16B can include components that are structurally and/or functionally similar to other thrombectomy systems described herein. For example, the thrombectomy system can include an outer sleeve 1602 and a catheter 1604. In FIGS. 16A and 16B, a distal end of the catheter may have been deployed (e.g., from within a sleeve) such that it has an expanded configuration to facilitate thrombus removal. In use, the catheter can be navigated to the site of a thrombus while being within an outer sleeve that constrains it to a smaller diameter, and then once at the thrombus site, can be deployed out of the sleeve (e.g., by retracting the sleeve relative to the catheter) to allow the distal end of the catheter to expand into the expanded configuration shown in FIGS. 16A and 16B.

Handle Assembly

FIGS. 17A-17D are cross-sectional views of a proximal end of a thrombectomy system, according to embodiments. The thrombectomy system can include components that are structurally and/or functionally similar to other thrombectomy systems described herein. The thrombectomy system can include a handle assembly 1700 including a first adjustment mechanism 1710 (e.g., first catheter adjustment mechanism), a second adjustment mechanism 1720 (e.g., second catheter adjustment mechanism), a connector 1730, and ports 1740, 1742. The handle assembly 1700 can be couplable to a drive unit 1750 including a shaft 1760. In some embodiments, the first adjustment mechanism 1710 may be configured to translate a sleeve 1718 and/or a catheter 1714 (e.g., an aspiration catheter) relative to the handle assembly 1700. In some embodiments, the second adjustment mechanism 1720 may be configured to rotate a catheter 1714 about a longitudinal axis of the catheter. The adjustment mechanisms 1710, 1720 can be implemented as a knob, wheel, slider, sliding carriage, combinations thereof, and the like. For example, the second adjustment mechanism 1720 can be implemented as a knob that can be rotated to enable rotation of the catheter 1714, and the first adjustment mechanism 1710 can be a thumb wheel configured to translate the sleeve 1718 the catheter 1714 relative to the other. In some embodiments, the adjustment mechanisms 1710, 1720 can be configured to hold the position between the aspiration catheter 1714 and the sleeve 1718 when not being adjusted.

The port 1740 can be configured to receive a guidewire (not shown), such that the catheter 1714 and the sleeve 1718 can be advanced to a target site over a guidewire. The port 1742 can be a vacuum port for coupling to a vacuum source, such that a negative pressure can be generated within a lumen of the catheter 1714.

In some embodiments, the drive unit 1750 can be configured to be coupled to the connector 1730. The drive unit 1750 can support a shaft 1760 (and optionally a stylet) that can be inserted and advanced through an inner lumen of the catheter 1714, e.g., after the catheter 1714 has been positioned within a body lumen. The drive unit 1750 may be configured to rotate one or more of the shaft 1760 and stylet (not shown) disposed within the shaft 1760. For example, the drive unit 1750 can include a concentric bearing assembly that allows for driving of the shaft 1760 and the stylet from parallel, offset motors via gears and/or belts.

While only some internal components of the handle assembly 1700 are depicted and described herein, it can be appreciated that handle assembly 1700 can include components that are structurally and/or functionally similar to the components of other handle assemblies described herein (e.g., handle assembly 160, drive unit 140, drive system 232). For example, handle assembly 1700 can include a power source (e.g., a battery), one or more seals, etc. The handle assembly 1700 may comprise one or more seals to inhibit suction leak.

The drive unit 1750 can include components that are structurally and/or functionally similar to the components of other drive units described herein (e.g., drive unit 140, drive system 232). In some embodiments, the drive unit 1750 can include two drive motors that each independently drive the rotation of one of the shaft 1760 or the stylet. In some embodiments, the drive unit 1750 can include a single motor that drives the rotation of the shaft 1760 and optionally the stylet. The drive unit 1750 can include an actuation mechanism (not shown) that can be pushed to control a drive system to drive the rotation of the shaft 1760 and/or the stylet. The shaft 1760 can be structurally and/or functionally similar to other shafts described herein, and the stylet can be structurally and/or functionally similar to other stylets described herein. For example, the shaft 1760 can include a lumen within which the stylet is disposed, and the stylet can include a shaped distal end that, when positioned within the shaft 1760, can cause the shaft 1760 to take on a shape corresponding to that of the shaped distal end of the stylet. In some embodiments, the shaft 1760 can be used without a stylet. In such embodiments, the shaft 1760 can include a pre-set shape (e.g., bend or curve), e.g., for enhancing orbital movement of a distal end of the shaft 1760. In some embodiments, the handle assembly 1700 and/or drive unit 1750 may be coupled to a fluid conduit configured to purge air from the aspiration catheter 1714, the shaft 1760, and/or the stylet (e.g., prior to use).

When the drive unit 1750 is coupled to the handle assembly 1700, the shaft 1760 (and optionally stylet) can be positioned within the catheter 1714 such that a distal end of the shaft 1760 (and optionally stylet) is positioned proximal of a distal end of the catheter 1714. In some embodiments, the distal end of the shaft 1760 (and optionally stylet) can be positioned within an expandable tip of the catheter 1714, as described in other embodiments herein. In use, the catheter 1714 can be navigated (e.g., with the sleeve 1718 over the catheter 1714) to a target site and deployed (e.g., by retracting the sleeve 1718 and/or extending the catheter 1714 outside of the sleeve 1718), and the shaft 1760 (and optionally stylet) can be advanced through a lumen of the catheter 1714 until the drive unit 1750 engages with the handle assembly 1700 (e.g., via connector 1730). The drive unit 1750 can then be coupled to the handle assembly (e.g., via connector 1730), e.g., by a twist lock or straight push lock interface. After the drive unit 1750 is fully coupled to the handle assembly 1700, then the shaft 1760 (and optionally stylet) is positioned for thrombectomy, e.g., for rotation within the catheter to remove thrombus, as described above. In some embodiments, finer adjustments of a position of the shaft 1760 and/or stylet can be effectuated by one or more actuation mechanisms coupled to the drive unit 1750 and/or adjusting the coupling between the drive unit 1750 and the handle assembly 1700 (e.g., by screwing or unscrewing the drive unit 1750 to change a relative position of the drive unit 1750 to the handle assembly 1700).

Figure 19:
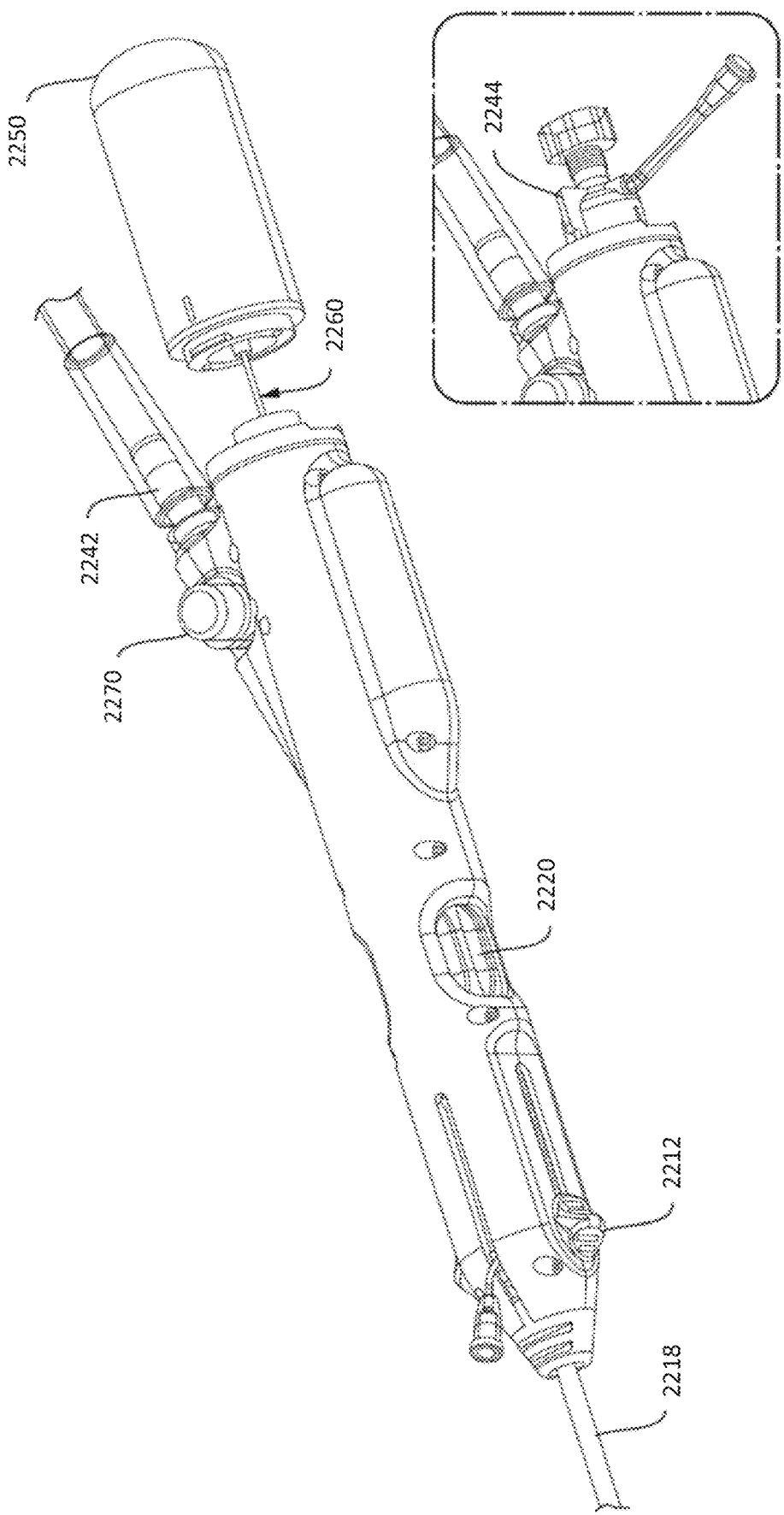
FIG. 19 is a perspective view of a handle of a thrombectomy system, according to embodiments.

FIG. 19 is a perspective view of a proximal end of a thrombectomy system, according to embodiments. The thrombectomy system can include components that are structurally and/or functionally similar to other thrombectomy systems described herein. The thrombectomy system can include a handle assembly 2200 including a first adjustment mechanism including a slider 2212 (e.g. a first handle adjustment mechanism), a second adjustment mechanism 2220 (e.g., a second handle adjustment mechanism), and a sleeve 2218. The first adjustment mechanism 2212, the second adjustment mechanism 2220, and the sleeve 2218 can be structurally and/or functionally similar to the first adjustment mechanism 1712, the second adjustment mechanism 1720, and the sleeve 1718 and therefore are not described in detail here again. The handle assembly 2200 can be couplable to a drive unit 2250 supporting a shaft 2260. Additionally, the handle assembly 2200 can be coupled to a vacuum source via a port 2242.

While the handle assembly 2200 and drive unit 2250 are similar to other handle assemblies and drive units described herein, and in particular to those depicted in FIGS. 17A-17D, the handle assembly 2200 and drive unit 2250 are configured to couple differently to one another that that shown in FIGS. 17A-17D. In particular, the drive unit 2250 is configured to couple to the handle assembly 2200 at a location that extends along a longitudinal axis of the catheter and sheath. As such, the shaft 2260 is configured to extend linearly (or substantially linearly) along a length of the handle assembly 2200 into a lumen of the catheter. In FIG. 19, the drive unit 2250 is shown decoupled from the handle assembly 2200 with the shaft 2260 being partially inserted into the handle assembly 2200. In operation, the shaft 2260 can be inserted into the handle assembly 2200 and advanced along a length of the catheter until the drive unit 2250 can be coupled to the handle assembly 2200.

When the drive unit 2250 is not coupled to the handle assembly 2200, a portion 2244 can be coupled to the handle assembly 2200. The port 2244 may be configured for one or more of a fluid flush and contrast injection. The port 2244 can also be used to receive a guidewire, e.g., to facilitate advancement of the catheter over the guidewire during navigation to a target site. In use, the handle assembly 2200 with the port 2244 as shown coupled to the handle assembly 2200 can be guided, e.g., along a guidewire, to a target site. The first adjustment mechanism 2212 can be retracted proximally to extend the catheter distal end (e.g., an expandable distal tip of the catheter) out of the sleeve 2218 such that the distal end is disposed within the vessel lumen. The second adjustment mechanism 2220 can also be rotated to adjust a positioning of the catheter distal end, e.g., as a result of adjusting the direction of a bend or curve in the catheter. Optionally, fluids can be delivered through the port 2244 at some point prior to, during, or after the catheter is navigated to the target site. The port 2244 can then be removed, and the shaft 2260 can be inserted into the handle assembly 2200 (e.g., where the port 2244 was previously coupled) until the drive unit 2250 can couple to the handle assembly 2200. Once the drive unit 2250 is coupled to the handle assembly 2200, the distal end of the shaft 2260 can be positioned within the catheter lumen near a distal end of the catheter (e.g., within the expandable tip of the catheter).

In some embodiments, the handle assembly 2200 may include a vacuum interrupter or vacuum valve 2270 configured to control application of negative suction through the catheter. For example, the vacuum interrupter 2270 can be a switch configured for selectively actuated suction, such as, for example, pulsed suction and/or metered flow. In some embodiments, negative suction may be applied upon operator engagement with the activation element and halted when the activation element has been released. In some embodiments, the vacuum interrupter 2270 may be further configured to control shaft rotation. For example, shaft rotation may be actuated after negative suction has been activated by the vacuum interrupter 2270. In an example implementation, the vacuum interrupter 2270 can be configured to (1) activate the vacuum pressure in response to being depressed a first amount, and (2) activate the drive system 2250 to rotate the shaft in response to being depressed a second amount greater than the first amount. By only triggering the shaft rotation after the vacuum is activated, the physician can avoid agitating the patient's blood (e.g., via the shaft rotation) when there is no vacuum to remove the agitated blood.

While a stylet is not described with reference to the system shown in FIG. 19, it can be appreciated that a stylet can be used with the system, e.g., by being included within the shaft assembly and being coupled to the drive unit 2250. The user can then selectively rotate the shaft 2260 and/or stylet.

FIGS. 18A and 18B are perspective views of a handle assembly 1800 and a drive unit 1810 including a shaft 1820, according to embodiments. FIG. 18A shows the handle assembly 1800 separated from the drive unit 1810, and FIG. 18B shows the drive unit 1810 coupled to the handle assembly 1800 with the shaft 1820 inserted into the handle assembly 1800. The handle assembly 1800 and drive unit 1810 can be structurally and/or functionally similar to other handle assemblies and drive units described herein, and in particular, to that depicted in FIGS. 17A-17D. As such, certain details of such components are not provided herein again. As shown in FIGS. 18A-18B, then handle assembly 1800 can be designed ergonomically, e.g., to enable single handle operation. For example, the handle assembly 1800 with its adjustment mechanisms (e.g., first and second adjustment mechanisms, such as that described with reference to FIGS. 17A-17D) can be designed to be operated using a single hand with control of both distal tip advancement, configuration, and orientation.

FIGS. 20A and 20B depict another example of a proximal end of a thrombectomy system, according to embodiments. FIG. 20A is a side view of a handle assembly 2300 coupled to a drive unit 2310 and a vacuum source 2330. FIG. 20B is a side view of the handle assembly 2300 coupled to the vacuum source 2330 and not yet coupled to the drive unit 2310 such that the shaft 2320 can be partially viewed. The handle assembly 2300 and drive unit 2310 can be structurally and/or functionally similar to other handle assemblies and drive units described herein, and in particular, to that depicted in FIG. 19. As such, certain details of such components are not provided herein again.

Visualization Features

In some variations, an aspiration catheter may comprise a metal-based radiopaque marker comprising one or more of a ring, band, coating, plating, and ink (e.g. platinum, platinum-iridium, gold, nitinol, palladium) configured to permit fluoroscopic visualization.

The aspiration catheters described herein may comprise any radiopaque metal, such as tungsten, platinum iridium, stainless steel, titanium, as well as a tungsten filled polymer, zirconia ceramic, or any suitable radiopaque material. A visualization feature may be located at any suitable position on or within the catheter (e.g., one or more exterior surfaces of the device, inside of the catheter, or the like). In some variations, one or more portions of the aspiration catheter may be made from a radiopaque material, or visualization feature may be attached to the device by any suitable method, for example, by mechanical attachment (e.g., embedded in a portion of the catheter, circumferential circumscription, or the like), adhesive bonding, welding, soldering, combinations thereof or the like. In some embodiments, the Nitinol tubing used to form the distal expandable tip and adjacent curved section may be gold plated for enhanced fluoroscopic visualization.

II. Methods

Also described here are methods for removing occluding material within vasculature (e.g., a thrombus) using the systems and devices described herein. In particular, the systems and devices described herein can be configured to navigate vasculature and remove a thrombus. Methods of using such systems and devices can include, for example, advancing an aspiration catheter to a target site in a subject, activating a drive system configured to rotate one or more of a shaft and stylet, activating a vacuum source to aspirate through the aspiration catheter, drawing a thrombus at the target site into the aspiration catheter, and removing the aspiration catheter and thrombus from the subject.

Figure 22A:
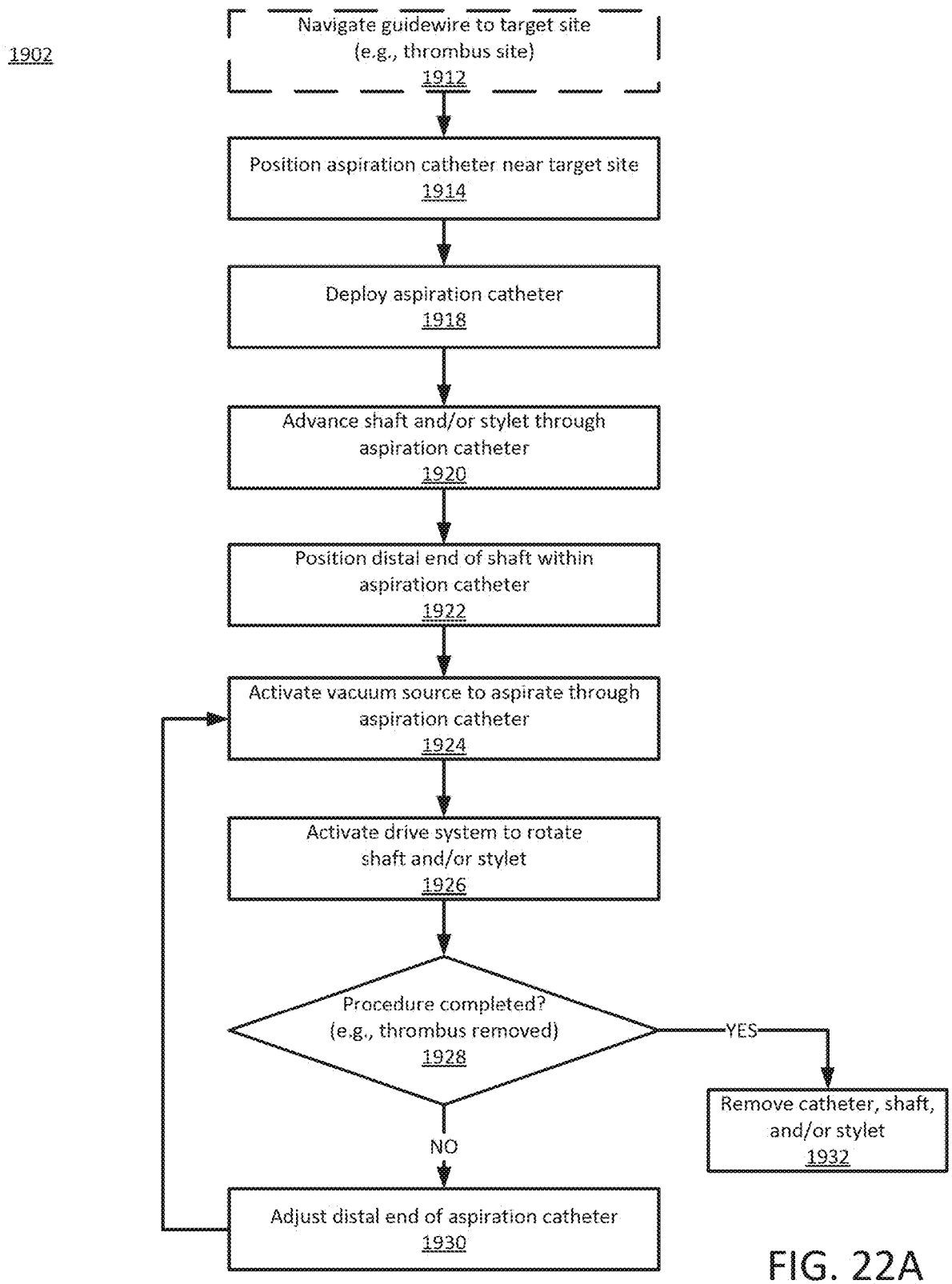
FIGS. 22A and 22B are flow diagrams of methods of performing a thrombectomy procedure, according to embodiments.

FIG. 22A is a flow chart of a method 1902 for performing a thrombectomy, e.g., using an aspiration catheter that is separate from a handle assembly and shaft assembly of a thrombectomy system. The method 1902 may optionally include navigating a guidewire (and/or microcatheter) to a target site (e.g., thrombus site), at 1912. In some embodiments, the target site may be disposed within pulmonary vasculature.

At 1914, the aspiration catheter (e.g., catheter 114, 214, etc.) can be advanced toward the target site over the guidewire (and/or microcatheter). In some embodiments, the aspiration catheter disposed within a sleeve can be advanced over the guidewire, without advancing a shaft, toward the target site. In some embodiments, the sleeve, catheter, and shaft can be advanced together into the vasculature toward the target site. In some embodiments, a distal end of the aspiration catheter may be positioned relative to the target site by rotating the sleeve as described herein where the sleeve has, for example, a bend or curve. Advancement of the aspiration catheter may be controlled at the handle assembly.

At 1918, if the aspiration catheter is at the target site (e.g., the distal end of the catheter is near the occluding material or thrombus), the aspiration catheter may be deployed. For example, a distal end (e.g., expandable tip) of the aspiration catheter may be advanced out of a distal end of the sleeve such that the distal end of the aspiration catheter transitions from a retracted configuration to an expanded configuration. Additionally or alternatively, the sleeve may be withdrawn relative to the aspiration catheter such that the distal end of the aspiration catheter is distal to a distal end of the sleeve. In some embodiments, the guidewire (and/or microcatheter) may be withdrawn from the body. In some embodiments, a distal end of the aspiration catheter may be positioned relative to the target site by rotating the aspiration catheter as described herein where a distal portion of the aspiration catheter has, for example, a bend or curve. Deployment of the aspiration catheter may be controlled at the handle assembly.

A shaft (e.g., shaft 112, 212, etc.) and/or optionally a stylet (e.g., stylet 216, etc.), as described herein, may be advanced toward the target site through the aspiration catheter, at 1920. In some embodiments, a proximal end of the shaft and optionally stylet may be coupled to a drive unit, as described herein. As the shaft and optionally stylet advances towards a distal end of the aspiration catheter, the shaft and optionally stylet may be advanced via rotation (e.g., slow rotation) so as to facilitate passage towards the distal end of the aspiration catheter. For example, the shaft and optionally stylet may be slowly rotated from a distance of about 20 cm or less (or about 10 cm or less) from the distal end of the aspiration catheter.

The shaft and optionally stylet can be advanced until it is positioned a preset distance proximal of a distal end of the aspiration catheter, at 1922, e.g., about 1 mm, about 5 mm, about 1 cm, about 2 cm, including all values and ranges in-between. The drive unit can be locked to the aspiration catheter. One or more adjustment mechanisms (e.g., adjustment mechanism 134) can be used to fine or micro-adjust the shaft and/or stylet to a preset position proximal of the distal end of the aspiration catheter (e.g., within an expandable tip). Advancement and positioning of the shaft and optionally stylet may be controlled at the handle assembly and/or drive unit.

In some embodiments, the catheter assembly may be configured to be tracked over a guidewire or stylet. In some embodiments, the shaft and optionally stylet may define a lumen (not shown). For example, a guidewire may be slidably disposed within a shaft lumen or a stylet lumen. In some embodiments, the shaft and optionally stylet can be advanced over a guidewire toward the thrombus site together, while in other embodiments, one of the shaft and optionally stylet can be advanced first toward the thrombus site (e.g., the shaft 212) and the other of the shaft and optionally stylet (e.g., the stylet 216) can be subsequently advanced into position. Optionally, at any point during or after the shaft and optionally stylet insertion, drive system and shaft with optional stylet can be removed from the aspiration catheter to be cleaned and subsequently reinserted to continue the thrombectomy process. Further optionally, a length of the shaft and optionally stylet may be substantially equal to the aspiration catheter such that the drive system coupled to the shaft and optionally stylet rotates the shaft and optionally stylet within the aspiration catheter (e.g., expandable tip) at a same longitudinal position of the aspiration catheter.

The vacuum source can be activated to aspirate the thrombus through the aspiration catheter, at 1924. For example, the vacuum source can generate sufficient negative pressure to draw in one or more of a thrombus and/or fluid into a distal end of the catheter, and combined with the movement of the shaft and stylet, at 1926 can cause the thrombus to move proximally within the lumen of the aspiration catheter. Activation of negative suction may be controlled at the handle assembly as described herein. An amount of negative suction may be controlled. In some embodiments, the suction (e.g., vacuum pressure) may be delivered in dynamic fashion by changing pressures at different frequencies between about 0.5 Hz and about 1000 Hz with a magnitude between about −100 kPa and about −5 kPa on a gauge pressure scale. In some embodiments, the vacuum pressure may be constant.

A drive system may be activated to independently rotate one or more of the shaft and stylet, at 1926. For example, simultaneous with (or shortly before or after) activating the vacuum source, the rotation of the shaft and stylet may be activated (e.g., via a switch on the handle). One or more of a speed and direction of axial rotation of the shaft and stylet may be controlled. The axial rotation of the stylet may induce orbital motion of the shaft within the catheter, as described above. The rotation of the shaft and stylet can cause the shaft to have axial rotation and orbital motion, which can lead to desirable interactions with a thrombus to remove it from the vasculature (e.g., by compressing the thrombus, wiping the thrombus off of an inner diameter of the aspiration catheter, or twisting the thrombus to reshape/elongate the thrombus), at 1926. In some embodiments, rotation of one or more of the shaft and stylet may depend on activation of negative suction. For example, rotation of one or more of the shaft and stylet may occur only when negative suction is applied through the aspiration catheter.

In some embodiments, the thrombus may be suctioned into a lumen of the aspiration catheter and mechanically interact with the shaft disposed within the lumen of the catheter. For example, orbital motion of the shaft may separate the clot from an inner circumference of the catheter, thereby reducing static friction and aiding proximal translation of the thrombus through the aspiration catheter via negative pressure. A physician can monitor the patent flow in the aspiration catheter and/or wait for a predefined period of time after activating the rotation of the shaft and/or stylet to determine whether the thrombectomy is completed. Once the thrombectomy is completed, the shaft assembly and/or the aspiration catheter may be removed (e.g., withdrawn) from the patient. In some embodiments, the physician can manually pulse one or more of the negative pressure and rotation using a handle assembly as described herein. Manual control of vacuum pressure facilitates precise control of suction and may reduce periprocedural blood loss relative to constant negative pressure applied in the lumen of the aspiration catheter.

At 1928, a determination of whether the procedure is completed can be performed. For example, if the thrombus is removed, the physician may determine that the procedure is completed. The catheter, shaft, and/or stylet can be removed, at 1932. Negative suction may also be deactivated. If the procedure is not complete (e.g., thrombus removal is not satisfactory), then at least a distal end of the aspiration catheter and/or sleeve may be adjusted, at 1930. For example, the distal end may of the catheter can be rotated around a circumference of a blood vessel to reorient the expandable tip of the catheter to ensure thrombus removal (e.g., via catheter adjustment mechanism(s)). Then the process may return to activating the vacuum source, at 1924, and/or activating the drive system, at 1926.

In some embodiments, the aspiration catheter and/or the target site may be indirectly visualized to determine if further repositioning of the aspiration catheter is needed. Such visualization can be done using one or more visualization techniques and visualization features incorporated within the aspiration catheter. For example, visualization features and techniques may facilitate one or more of imaging, positioning, alignment, and operation of the aspiration catheter in a vessel. For example, indirect visualization techniques may include, but are not limited to ultrasound, fluoroscopy, and X-ray. A contrast agent may be used to visualize the aspiration catheter relative to tissue such as a thrombosis. For example, a contrast agent (e.g., contrast medium) may be output by the aspiration catheter. The aspiration catheter may be indirectly visualized as desired throughout a thrombectomy procedure.

Figure 22B:
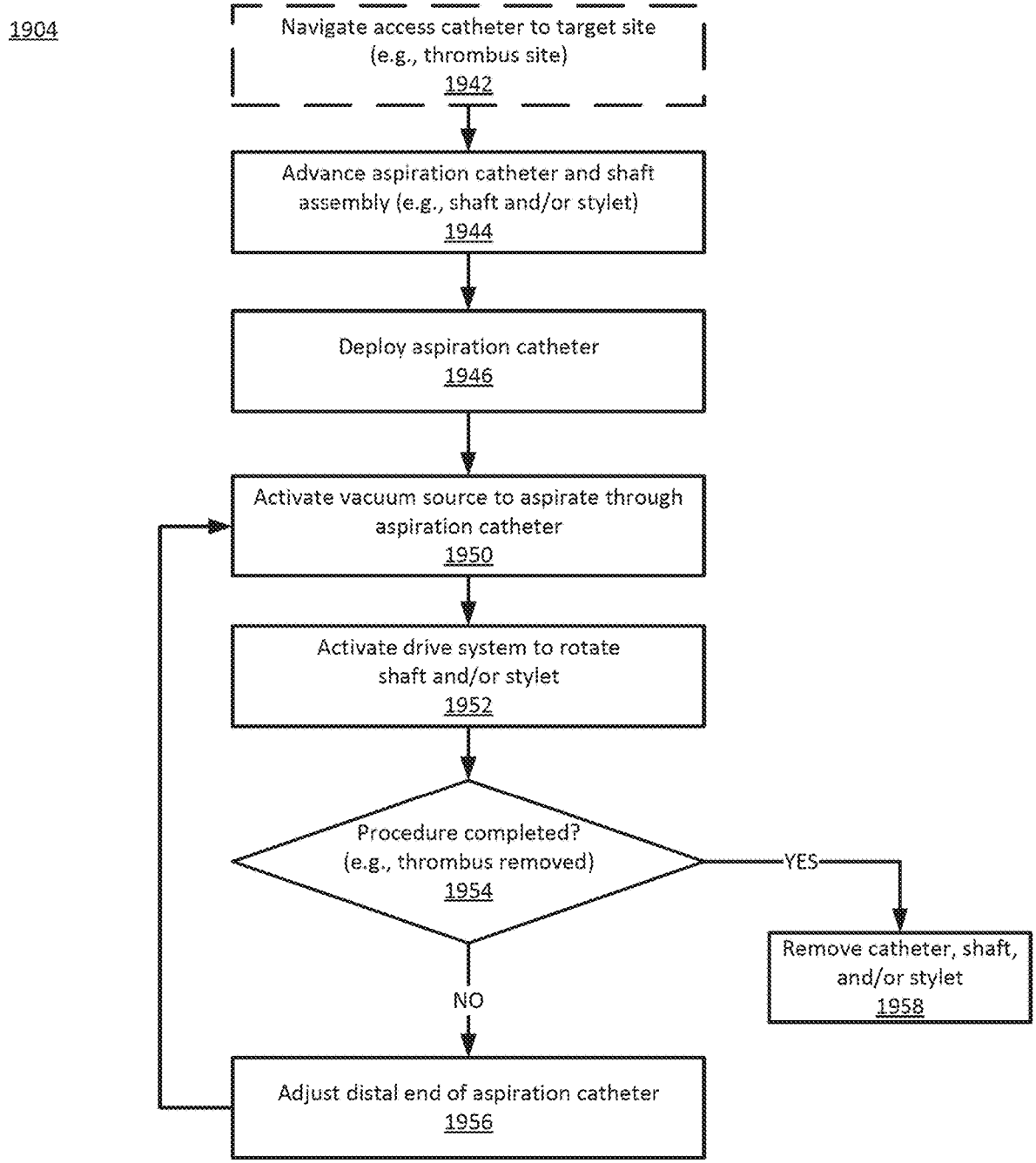

FIG. 22B is a flow chart of another method 1904 for performing a thrombectomy using a thrombectomy system where an aspiration catheter and handle assembly is integrated with a drive unit for controlling a shaft assembly. The method 1904 may optionally include navigating a guidewire (and/or microcatheter) and/or access sheath (or access catheter) to a target site (e.g., thrombus site), at 1942.

At 1944, the aspiration catheter (e.g., catheter 114, 214, etc.) and shaft assembly (e.g., including shaft and/or stylet) can be advanced toward the target site over the guidewire or within the access sheath. For example, the catheter assembly and the shaft assembly can be advanced together into the vasculature over the guidewire (e.g., as a "buddy wire") toward the target site. That is, the shaft and guidewire (and/or microcatheter) may be side-by-side in the aspiration catheter during advancement. The guidewire (and/or microcatheter) may then be withdrawn from the body. Alternatively, the catheter assembly and the shaft assembly can be advanced together into the vasculature within an access catheter (e.g., sleeve) that has been positioned with its distal end near or sufficiently near the thrombus site. In some embodiments, a distal end of the aspiration catheter may be positioned relative to the target site by rotating the sleeve as described herein where the sleeve has, for example, a bend or curve. Advancement of the aspiration catheter may be controlled at the handle assembly.

At 1946, if the aspiration catheter is at the target site (e.g., the distal end of the catheter is near the occluding material or thrombus), the aspiration catheter may be deployed. For example, a distal end (e.g., expandable tip) of the aspiration catheter may be advanced out of a distal end of the sleeve such that the distal end transitions from a retracted configuration to an expanded configuration. In some embodiments, a distal end of the aspiration catheter may be positioned relative to the target site by rotating the aspiration catheter as described herein where a distal portion of the aspiration catheter has, for example, a bend or curve. Deployment of the aspiration catheter may be controlled at the handle assembly. In some embodiments, the sleeve may be at least partially withdrawn while the thrombosis is being removed.

A vacuum source can be activated to aspirate the thrombus through the aspiration catheter, at 1950. For example, the vacuum source can generate sufficient negative pressure to draw in one or more of a thrombus and/or fluid into a distal end of the catheter, and combined with the movement of the shaft and stylet, at 1952 can cause the thrombus to move proximally within the lumen of the aspiration catheter. Activation of negative suction may be controlled at the handle assembly as described herein. An amount of negative suction may be controlled. In some embodiments, the suction (e.g., vacuum pressure) may be delivered in dynamic fashion by changing pressures at different frequencies between about 0.5 Hz and about 1000 Hz with a magnitude between about −100 kPa and about −5 kPa on a gauge pressure scale. In some embodiments, the vacuum pressure may be constant.

A drive system may be activated to independently rotate one or more of the shaft and stylet, at 1952. For example, simultaneous with (or shortly before or after) activating the vacuum source, the rotation of the shaft and stylet may be activated (e.g., via a switch on the handle). One or more of a speed and direction of axial rotation of the shaft and stylet may be controlled. The axial rotation of the stylet may induce orbital motion of the shaft within the catheter, as described above. The rotation of the shaft and stylet can cause the shaft to have axial rotation and orbital motion, which can lead to desirable interactions with a thrombus to remove it from the vasculature (e.g., by compressing the thrombus, wiping the thrombus off of an inner diameter of the aspiration catheter, or twisting the thrombus to reshape/elongate the thrombus).

In some embodiments, the thrombus may be suctioned into a lumen of the aspiration catheter and mechanically interact with the shaft disposed within the lumen of the catheter. For example, orbital motion of the shaft may separate the clot from an inner circumference of the catheter, thereby reducing static friction and aiding proximal translation of the thrombus through the aspiration catheter via negative pressure. In some embodiments, rotation of one or more of the shaft and stylet may depend on activation of negative suction. For example, rotation of one or more of the shaft and stylet may occur only when negative suction is applied through the aspiration catheter.

At 1954, a determination of whether the procedure is completed can be performed. For example, if the thrombus is removed, the physician may determine that the procedure is completed. The catheter, shaft, and/or stylet can be removed (e.g., withdrawn) from the patient, at 1958. Negative suction may also be deactivated. If the procedure is not complete (e.g., thrombus removal is not satisfactory), then at least a distal end of the aspiration catheter may be adjusted, at 1956. For example, the distal end of the aspiration catheter can be rotated around a circumference of a blood vessel to reorient the expandable tip of the catheter to ensure thrombus removal (e.g., via catheter adjustment mechanism(s)). Then the process may return to activating the vacuum source, at 1950.

Figure 23A:
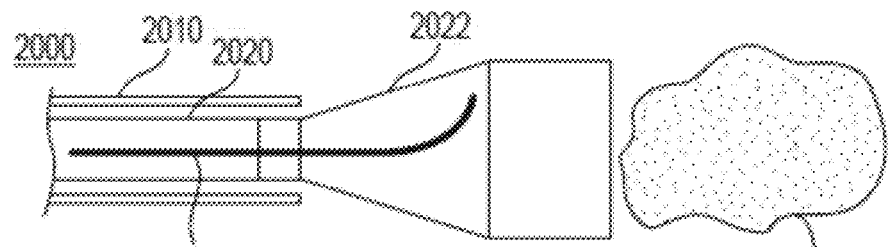
FIGS. 23A-23E are cross-sectional side views of methods of performing a thrombectomy procedure, according to embodiments.

FIGS. 23A-23E are cross-sectional side views of methods of performing a thrombectomy procedure depicting clot engagement, ingestion, maceration, and transport. FIG. 23A depicts a distal end 2022 (e.g., expandable tip) of a catheter 2020 deployed from a sleeve 2010, at 2000. A shaft 2030 may be disposed within a lumen of the distal end 2022. The shaft 2030 may have a curved distal end. The distal end 2022 of the catheter 2020 may be positioned adjacent a clot 2050 for removal.

Figure 23B:
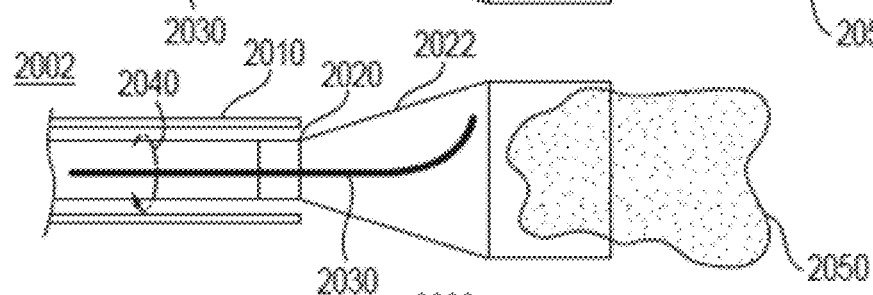

FIG. 23B depicts the shaft 2030 rotating to draw the clot 2050 into the distal end 2022 of the catheter 2020. In some embodiments, the shaft 2030 may rotate such as to remain in contact with or at a predetermined distance to an inner wall of the distal end 2022. Negative pressure may also be applied concurrently through the lumen to further draw the clot 2050 into the catheter 2020.

Figure 23C:
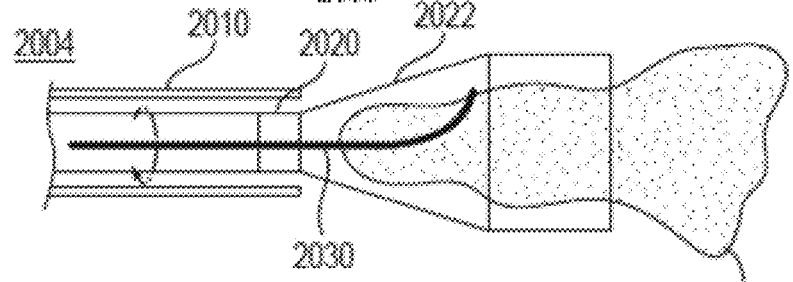

FIG. 23C depicts the clot 2050 being drawn in and reshaped by both the distal end 2022 of the catheter 2020 and the shaft 2030. For example, the clot 2050 may be elongated as it is drawn further into the catheter 2020. The larger diameter of the distal end 2022 relative to the catheter 2020 can enable a greater force of clot engagement at standard vacuum pressures, thereby providing greater assurance that clot will be well engaged and less likely to dislodge.

Figure 23D:
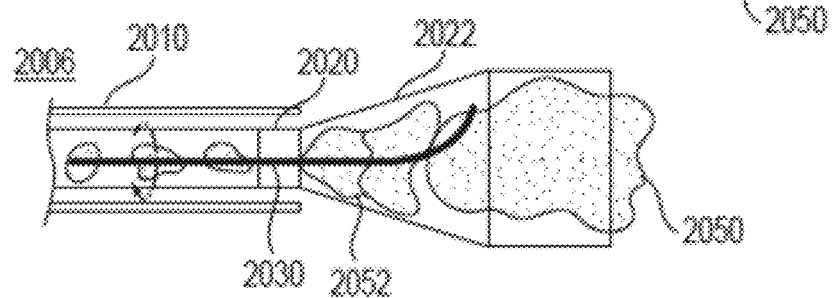

FIG. 23D depicts maceration of the clot 2050 by the axial and orbital rotational forces applied by the shaft 2030. For example, the clot 2050 may break up into separate portions 2052 sized to be withdrawn from the body through the catheter 2020. Clot interaction with orbital shaft at least at the point where the reduction in inner lumen diameter would otherwise prevent clot translation using vacuum alone. Clot maceration (e.g., separation) by the shaft 2030 facilitates fragmented or minimized clot portions 2052 to advance through the catheter 2020 without clogging or forming blockages. Conventional aspiration catheters frequently lose suction when large clots clog a catheter lumen.

In some embodiments, the catheter 2020 containing the macerated clot 2052 may be withdrawn into the sleeve 2010, which may transition the distal end 2022 from an expanded configuration to a retracted configuration. As the distal end 2020 is withdrawn and collapsed into the sleeve 2010, the distal end 2020 can compress around the clot 2050 and further ensure clot removal withdrawn from the patient.

Figure 23E:
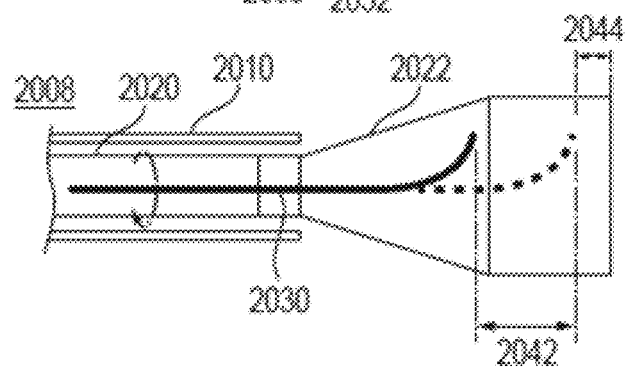

FIG. 23E is depicts translation of the shaft 2030 through the distal end 2022 of the catheter 2020 by a first distance 2042. In some embodiments, a distal end of the shaft 2030 may be positioned at a second distance 2044 away from a distal end of the catheter 2020.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Any and all references to publications or other documents, including but not limited to, patents, patent applications, articles, webpages, books, etc., presented anywhere in the present application, are herein incorporated by reference in their entirety. Moreover, all definitions, as defined and used herein, should be understood to control over dictionary definitions, definitions in documents incorporated by reference, and/or ordinary meanings of the defined terms.

The specific examples and descriptions herein are exemplary in nature and embodiments may be developed by those skilled in the art based on the material taught herein without departing from the scope of the present invention.

We claim:

1. A thrombectomy device for removing a thrombus from a vessel,
the thrombectomy device comprising:
a handle assembly;
a vacuum source configured to generate vacuum pressure;
a catheter coupled to the handle assembly, the catheter including:
a tubular body defining a lumen; and
an expandable distal portion configured to transition from a collapsed configuration having a first diameter that is substantially similar to a diameter of the tubular body to an expanded configuration having a funnel-like shape that progressively increases to a second diameter that is greater than the diameter of the tubular body,
wherein the expandable distal portion includes a metallic frame that defines a plurality of rows of open cells and an atraumatic wave-shaped ring having a plurality of troughs disposed at a distal end of the expandable distal portion, and every other open cell of a distalmost row of open cells is connected to a respective trough of the atraumatic wave-shaped ring;
a flexible shaft;
a rotational drive assembly configured to rotate the flexible shaft axially and orbitally such that a distal end of the flexible shaft is disposed within about 1 cm from an end of the expandable distal portion and a diameter of an orbital path of the rotating distal end of the flexible shaft is greater than the diameter of the tubular body; and
an actuator disposed on the handle assembly, the actuator configured to be actuated to cause the vacuum source to generate the vacuum pressure within the lumen of the tubular body and to cause the rotational drive assembly to rotate the flexible shaft.

2. The thrombectomy device of claim 1, wherein the catheter defines at least one opening disposed near a proximal end of the expandable distal portion, the at least one opening configured to increase fluid available to mix with the thrombus to improve flow of the thrombus proximally into and through the lumen.

3. The thrombectomy device of claim 1, wherein the distal end of the flexible shaft is configured to break or reshape portions of the thrombus disposed within the expandable distal portion.

4. The thrombectomy device of claim 1, wherein
when the expandable distal portion is in the collapsed configuration, the open cells of each row of the plurality of rows of open cells having a longitudinal length that is larger than a longitudinal length of the open cells of a row of the plurality of rows of open cells that is immediately proximal of that row.

5. The thrombectomy device of claim 4, wherein the atraumatic wave-shaped ring is at a distal end of the expandable distal portion.

6. The thrombectomy device of claim 4, wherein, when the expandable distal portion is in the collapsed configuration, the longitudinal length of the open cells of the plurality of rows of open cells disposed at a proximal end of the expandable distal portion is at least about 2 mm and the longitudinal length of the open cells of the plurality of rows of open cells disposed at a distal end of the expandable tip is less than about 5 mm.

7. The thrombectomy device of claim 4, wherein, when the expandable distal portion is in the expanded configuration, the open cells of the plurality of rows of open cells disposed at a proximal end of the expandable distal portion have a proximal angle of at least about −10° and the open cells of the plurality of rows of open cells disposed at a distal end of the expandable distal portion have a proximal angle of less than about 40°.

8. The thrombectomy device of claim 1, wherein the diameter of the orbital path of the rotating distal end of the flexible shaft corresponds to an inner diameter of the expandable distal portion of the catheter in the expanded configuration.

9. The thrombectomy device of claim 8, wherein the orbital path of the rotating distal end of the flexible shaft may be spaced by a predetermined distance from an inner surface of the expandable distal portion of the catheter in the expanded configuration.

10. The thrombectomy device of claim 1, wherein the expandable distal portion includes a coating that is disposed over the metallic frame.

11. The thrombectomy device of claim 10, wherein the coating has an inner layer and an outer layer that connect to one another at the plurality of open cells.

12. The thrombectomy device of claim 11, wherein each of the plurality of open cells has an area of at least about 0.5 mm$^2$ to enable the inner and outer layers of the coating to connect to one another at each open cell.

13. The thrombectomy device of claim 1, wherein the actuator is a first actuator, and the thrombectomy device further comprises:
   an outer sheath disposed around the catheter, the outer sheath and the catheter being movable relative to one another; and
   a second actuator disposed on the handle assembly, the second actuator configured to be actuated to cause at least one of the outer sheath and the catheter to translate relative to the other of the outer sheath and the catheter to allow the expandable distal portion to transition from the collapsed configuration to the expanded configuration.

14. The thrombectomy device of claim 13, wherein:
   the expandable distal portion in the expanded configuration has a pinch strength of between about 0.4 lbs. and about 3 lbs. such that the expandable distal portion in the expanded configuration is configured to withstand collapse from pressure gradients being generated within the expandable distal portion as the vacuum pressure acts on the thrombus within the expandable distal portion, and
   the expandable distal portion in the expanded configuration is configured to be retractable into the outer sheath in response to a retracting force of between about 0.5 lbs. and about 4.0 lbs.

15. The thrombectomy device of claim 13, wherein:
   the tubular body has a linear proximal section and a memory-set curved section disposed near the expandable distal portion, and
   the second actuator is further configured to be actuated to cause the at least one of the tubular body and the outer sheath to translate relative to the other of the tubular body and the outer sheath to selectively control a degree of exposure of the memory-set curved section outside of the outer sheath to change a degree of curvature of the memory-set curved section and a position of the expandable distal portion within the vessel.

16. The thrombectomy device of claim 15, wherein the tubular body is further configured to rotate to change the position of the expandable distal portion within the vessel.

17. The thrombectomy device of claim 15, wherein the memory-set curved section, when at least partially extended from the outer sheath, is configured to have a radius of curvature between about 10 mm and about 40 mm.

18. A thrombectomy device for removing a thrombus from a vessel, the thrombectomy device comprising:
   a handle assembly;
   a vacuum source configured to generate vacuum pressure;
   a catheter coupled to the handle assembly, the catheter including:
      a tubular body defining a lumen; and
      an expandable distal portion configured to transition from a collapsed configuration having a first diameter that is substantially similar to a diameter of the tubular body to an expanded configuration having a funnel-like shape that progressively increases to a second diameter that is greater than the diameter of the tubular body, wherein the expandable distal portion includes a metallic frame that defines a plurality of rows of open cells and an atraumatic wave-shaped ring having a plurality of troughs disposed at a distal end of the expandable distal portion, and every other open cell of a distalmost row of open cells is connected to a respective trough of the atraumatic wave-shaped ring;
   a flexible shaft having a distal end that is configured to be disposed within the expandable distal portion of the catheter;
   a rotational drive assembly configured to rotate the flexible shaft; and
   an actuator disposed on the handle assembly, the actuator configured to be actuated to cause the vacuum source to generate the vacuum pressure within the lumen of the tubular body and to cause the rotational drive assembly to rotate the flexible shaft.

19. The thrombectomy device of claim 18, wherein the actuator is a first actuator, and the thrombectomy device further comprises:
   an outer sheath disposed around the catheter, the outer sheath and the catheter being movable relative to one another; and
   a second actuator disposed on the handle assembly, the second actuator configured to be actuated to cause at least one of the outer sheath and the catheter to translate relative to the other of the outer sheath and the catheter to allow the expandable distal portion to transition from the collapsed configuration to the expanded configuration.

20. The thrombectomy device of claim 19, wherein:
   the expandable distal portion in the expanded configuration has a pinch strength of between about 0.4 lbs. and about 3 lbs. such that the expandable distal portion in the expanded configuration is configured to withstand collapse from pressure gradients being generated within the expandable distal portion as the vacuum pressure acts on the thrombus within the expandable distal portion, and
   the expandable distal portion in the expanded configuration is configured to be retractable into the outer sheath in response to a retracting force of between about 0.5 lbs. and about 4.0 lbs.

\* \* \* \* \*